(12) United States Patent
Pimenta

(10) Patent No.: US 10,687,957 B2
(45) Date of Patent: Jun. 23, 2020

(54) SPINAL IMPLANTS FOR ROTATIONALLY ADJUSTING VERTEBRAE

(71) Applicant: NuVasive, Inc., San Diego, CA (US)

(72) Inventor: Luiz Pimenta, Sao Paulo (BR)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 15/783,487

(22) Filed: Oct. 13, 2017

(65) Prior Publication Data

US 2018/0133023 A1     May 17, 2018

Related U.S. Application Data

(63) Continuation of application No. 13/950,277, filed on Jul. 24, 2013, now abandoned, which is a
(Continued)

(51) Int. Cl.
*A61F 2/44*     (2006.01)
*A61F 2/30*     (2006.01)
(Continued)

(52) U.S. Cl.
CPC ............ *A61F 2/4425* (2013.01); *A61F 2/447* (2013.01); *A61B 17/86* (2013.01); *A61F 2/4611* (2013.01); *A61F 2002/2835* (2013.01); *A61F 2002/305* (2013.01); *A61F 2002/30006* (2013.01); *A61F 2002/3038* (2013.01);
(Continued)

(58) Field of Classification Search
CPC ...... A61F 2/4425; A61F 2/447; A61F 2/4611; A61F 2/4455; A61F 2/442
See application file for complete search history.

(56) References Cited

U.S. PATENT DOCUMENTS

| 5,258,031 | A | 11/1993 | Salib et al. |
| 6,019,792 | A | 2/2000 | Cauthen |

(Continued)

FOREIGN PATENT DOCUMENTS

EP     2116211     11/2009

OTHER PUBLICATIONS

International Search Report and Written Opinion in corresponding International Application No. PCT/US2012/022600 dated Jul. 24, 2012 (20 pages).

*Primary Examiner* — Tessa M Matthews

(57) ABSTRACT

A spinal implant adapted to be positioned within a disc space between adjacent vertebrae includes a first intradiscal element, a second intradiscal element, and a coupling mechanism. The first and second intradiscal elements include respective first and second outer surfaces adapted to be positioned adjacent an endplate of respective first and second adjacent vertebrae. The first and second intradiscal elements further include respective first and second medial surfaces that are opposite the respective first and second outer surfaces, where the second medial surface is adapted to generally face the first medial surface upon assembly of the first intradiscal element with the second intradiscal element. The coupling mechanism is associated with the first and second medial surfaces and is adapted to provide relative rotational movement between the first and second intradiscal elements in a plane generally parallel with the first and second medial surfaces.

14 Claims, 30 Drawing Sheets

Related U.S. Application Data continuation of application No. PCT/US2012/022600, filed on Jan. 25, 2012.

(60) Provisional application No. 61/436,172, filed on Jan. 25, 2011.

(51) Int. Cl.
  *A61F 2/46*    (2006.01)
  *A61B 17/86*   (2006.01)
  *A61F 2/28*    (2006.01)

(52) U.S. Cl.
  CPC ............... *A61F 2002/3039* (2013.01); *A61F 2002/3052* (2013.01); *A61F 2002/30054* (2013.01); *A61F 2002/3054* (2013.01); *A61F 2002/30079* (2013.01); *A61F 2002/30364* (2013.01); *A61F 2002/30365* (2013.01); *A61F 2002/30367* (2013.01); *A61F 2002/30382* (2013.01); *A61F 2002/30387* (2013.01); *A61F 2002/30426* (2013.01); *A61F 2002/30428* (2013.01); *A61F 2002/30444* (2013.01); *A61F 2002/30464* (2013.01); *A61F 2002/30469* (2013.01); *A61F 2002/30504* (2013.01); *A61F 2002/30505* (2013.01); *A61F 2002/30522* (2013.01); *A61F 2002/30542* (2013.01); *A61F 2002/30543* (2013.01); *A61F 2002/30578* (2013.01); *A61F 2002/30616* (2013.01); *A61F 2002/30785* (2013.01); *A61F 2002/30823* (2013.01); *A61F 2002/30825* (2013.01); *A61F 2002/30841* (2013.01); *A61F 2002/30894* (2013.01); *A61F 2002/30904* (2013.01); *A61F 2310/00011* (2013.01); *A61F 2310/00017* (2013.01); *A61F 2310/00023* (2013.01); *A61F 2310/00179* (2013.01)

(56) References Cited

U.S. PATENT DOCUMENTS

| | | | |
|---|---|---|---|
| 9,351,852 B2 * | 5/2016 | Boa | A61F 2/442 |
| 2003/0040802 A1 | 2/2003 | Errico et al. | |
| 2003/0204260 A1 | 10/2003 | Ferree | |
| 2003/0233146 A1 | 12/2003 | Grinberg et al. | |
| 2004/0054421 A1 * | 3/2004 | McLean | A61F 2/4684 |
| | | | 623/23.11 |
| 2004/0102848 A1 * | 5/2004 | Michelson | A61F 2/446 |
| | | | 623/17.11 |
| 2004/0220668 A1 * | 11/2004 | Eisermann | A61B 17/1642 |
| | | | 623/17.11 |
| 2005/0154459 A1 | 7/2005 | Wolek et al. | |
| 2005/0203626 A1 | 9/2005 | Sears et al. | |
| 2005/0216081 A1 * | 9/2005 | Taylor | A61F 2/44 |
| | | | 623/17.11 |
| 2006/0089714 A1 | 4/2006 | Liu et al. | |
| 2006/0122703 A1 * | 6/2006 | Aebi | A61F 2/4425 |
| | | | 623/17.15 |
| 2006/0235529 A1 | 10/2006 | Ralph et al. | |
| 2007/0066289 A1 | 3/2007 | Silverbrook et al. | |
| 2007/0072475 A1 | 3/2007 | Justin et al. | |
| 2007/0255413 A1 | 11/2007 | Edie et al. | |
| 2008/0103601 A1 | 5/2008 | Biro et al. | |
| 2009/0138090 A1 | 5/2009 | Hurlbert et al. | |
| 2009/0281629 A1 | 11/2009 | Roebling et al. | |
| 2010/0004746 A1 * | 1/2010 | Arramon | A61F 2/4425 |
| | | | 623/17.15 |
| 2010/0016968 A1 * | 1/2010 | Moore | A61B 17/15 |
| | | | 623/17.11 |
| 2010/0016970 A1 | 1/2010 | Kapitan et al. | |
| 2010/0106251 A1 | 4/2010 | Kast | |
| 2011/0118845 A1 | 5/2011 | Overes et al. | |
| 2011/0319999 A1 * | 12/2011 | O'Neil | A61B 17/1671 |
| | | | 623/17.16 |
| 2012/0277865 A1 * | 11/2012 | Trieu | A61F 2/442 |
| | | | 623/17.16 |

\* cited by examiner

SPINAL IMPLANTS FOR ROTATIONALLY ADJUSTING VERTEBRAE

CROSS-REFERENCE TO RELATED APPLICATIONS

This application is a continuation of U.S. patent application Ser. No. 13/950,277, filed Jul. 24, 2013, now pending, which is a continuation of PCT/US2012/022600, filed Jan. 25, 2012, which claims priority to U.S. Provisional Application Ser. No. 61/436,172, filed on Jan. 25, 2011, the disclosures of which are incorporated herein by reference.

TECHNICAL FIELD

This document describes systems, devices and methods that relate generally to spinal surgery and, more particularly, to disc replacement systems and related methods for correction of spinal deformities, such as scoliosis, kyphosis, and lordosis.

BACKGROUND

Scoliosis is characterized by abnormal curvature of the spine. Scoliosis can result in abnormal curvature in the coronal plane to cause lateral curvature, abnormal curvature in the coronal plane associated with incorrect lordosis and/or kyphosis, and abnormal axial alignment of the spine to cause incorrect rotation. Scoliosis may therefore present as a tridimensional deformity of the spine.

The spine is made up of vertebrae connected by discs. Scoliosis can be associated with abnormally shaped vertebrae and abnormal intradiscal spacing. For example, the vertebrae and/or the discs may make have an abnormal wedge-shape associated with spinal curvature. Scoliosis can also be associated with abnormal relative alignment of the vertebrae, or vertebral axial rotation.

While minor scoliosis can sometimes be corrected with external braces, surgical correction involving fusion of vertebra is often required in more major cases. Such surgical procedures generally seek to restore vertebrae to a more normal alignment while providing for fusion of adjacent vertebrae. Fusion of vertebrae is typically encouraged by removal of the disc material.

Intervertebral spinal inserts can be used to provide support and maintain distance between adjacent vertebrae in cases where a patient's vertebral disc has been surgically removed. Intervertebral inserts can be used in this manner to establish or approximate normal alignment of vertebrae.

Traditional manual methods for estimating of the vertebral axial rotation in scoliosis based on X-ray images were relative imprecise. For example, the traditionally measured Cobb angle only evaluates spinal curvature in the sagittal and coronal planes. The degree of axial rotation is estimated by the positions of the spinous process or pedical shadow. The availability of high quality radiographs and specifically tailored software now enables more precise measurements of vertebral position, even in upper thoracic spine where image contrast is typically poor. Rajnics, P., et al. (2001) Computer Assisted Assessment of Spinal Sagittal Plane Radiographs. *J. Spinal Disorders*, 14 (2), pp. 135-42. Recently, computer-processed rotation measurements obtained from digital radiographs have enabled researchers to precisely measure the vertebral axial of rotation in scoliosis patents. Piheiro, A. P., et al. (2010) Validity and reliability of a computer method to estimate vertebral axial rotation from digital radiographs, *Eur. Spine J.*, 19 (3), pp. 415-20; Tanure, M. C. (2010) Reliability assessment of Cobb angle measurements using manual and digital methods. *Spine J.*, 10 (9), pp. 769-74.

SUMMARY

In one general embodiment, a spinal implant is adapted to be positioned within a disc space between adjacent vertebrae and includes a first intradiscal element, a second intradiscal element, and a coupling mechanism. The first intradiscal element includes a first outer surface adapted to be positioned adjacent an endplate of a first one of the adjacent vertebrae and includes a first medial surface that is opposite the outer surface. The second intradiscal element includes a second outer surface adapted to be positioned adjacent an endplate of a second one of the adjacent vertebrae and includes a second medial surface that is opposite the outer surface and adapted to generally face the first medial surface upon assembly of the first intradiscal element with the second intradiscal element. The coupling mechanism is associated with the first and second medial surfaces and is adapted to provide relative rotational movement between the first and second intradiscal elements in a plane generally parallel with the first and second medial surfaces.

In another general embodiment, a method of providing rotational adjustment of a spine includes implanting in a disc space between adjacent vertebrae, a spinal implant including a first intradiscal element having a first outer surface positioned adjacent an endplate of a first one of the adjacent vertebrae, and a first medial surface that is opposite the outer surface, a second intradiscal element having a second outer surface positioned adjacent an endplate of a second one of the adjacent vertebrae, and a second medial surface that is opposite the outer surface and positioned to generally face the first medial surface, and a coupling mechanism that is associated with the first and second medial surfaces and that is adapted to provide relative rotational movement between the first and second intradiscal elements in a plane generally parallel with the first and second medial surfaces. The method further includes separately engaging each of first and second intradiscal elements and applying forces in opposite directions to provide the relative rotational movement to a selected rotational orientation of the first intradiscal element in relation to the second intradiscal element.

Embodiments can include one or more of the following features.

In some embodiments, the coupling mechanism provides for the relative rotational movement about an axis at a center portion of the first and second medial surfaces.

In certain embodiments, the coupling mechanism includes a post element extending from a center portion of one of the first and second medial surfaces and an aperture provided in a center portion of the other of the first and second medial surfaces, the post element and aperture adapted to be coupled together.

In some embodiments, the post element includes a bulbous distal end, and the aperture includes an enlarged lower portion that receives the bulbous distal end of the post element.

In certain embodiments, the coupling mechanism further includes a snap ring adapted to be positioned about a neck of the post element proximal of the bulbous distal end, and the aperture further includes a circumferential chamber into which the snap ring is able to be engaged.

In some embodiments, the coupling mechanism includes an interconnecting rail and channel assembly including at least one rail and at least one cooperating channel for receiving one of the at least one rail, wherein at least one rail is provided on one of the first and second intradiscal elements and at least one channel is provided on the other of the first and second intradiscal elements, wherein the at least one rail is adapted to become interconnected with the at least one channel within a limited rotational range by bringing the first and second intradiscal elements together with their first and second medial surfaces facing each other with a rotational offset that is outside of the limited rotational range, and rotating the two intradiscal elements relative to one another to be within the limited rotational range and thereby engaging the rail within the channel.

In certain embodiments, the interconnecting rail and channel assembly are provided on the first and second medial surfaces at a location that is away from the axis of rotation that is located in the center portion of the first and second medial surfaces.

In some embodiments, the interconnecting rail and channel assembly include at least two semi-circular rails and two complementary semi-circular channels.

In certain embodiments, a first one of the at least two semi-circular rails and a first one of the at least two semi-circular channels are positioned on respective ones of the first and second medial surfaces at a location that is generally at a mid-point between the center portion of the first and second medial surfaces and a proximal end of the first and second medial surfaces, and a second one of the at least two semi-circular rails and a second one of the at least two semi-circular channels are positioned on respective ones of the first and second medial surfaces at a location that is generally at a mid-point between the center portion of the first and second medial surfaces and a distal end of the first and second medial surfaces.

In some embodiments, a first one of the at least two semi-circular rails and a first one of the at least two semi-circular channels are positioned on respective ones of the first and second medial surfaces at a location that is generally at a proximal end of the first and second medial surfaces, and a second one of the at least two semi-circular rails and a second one of the at least two semi-circular channels are positioned on respective ones of the first and second medial surfaces at a location that is generally at a distal end of the first and second medial surfaces.

In certain embodiments, a first rail of the at least one rail is L-shaped and a corresponding first channel of the at least one channel is L-shaped in a complementary fashion to allow the coupling of the first rail with the first channel.

In some embodiments, a first rail of the at least one rail is T-shaped and a corresponding first channel of the at least one channel is T-shaped in a complementary fashion to provide for the coupling of the first rail with the first channel.

In certain embodiments, a first rail of the at least one rail is provided at an acute angle with respect to the medial surface upon which the first rail is provided and a corresponding first channel of the at least one channel is provided at the same acute angle with respect to the medial surface in which the first channel is provided, to provide for the coupling of the first rail with the first channel.

In some embodiments, the at least one rail includes a first array of ridges on a first surface of the rail, and the at least one channel includes a second array of ridges on a second surface of the channel, wherein when the first intradiscal member is assembled with the second intradiscal member, wherein the first and second arrays are configured such that ridges of the first array fall within corresponding ridge valleys of the second array to resist the relative rotational movement of the first intradiscal element in relation to the second intradiscal element.

In certain embodiments, the spinal implant further includes a rotational movement resistance mechanism adapted to resist rotational movement from several incremented relative rotational positions of the first intradiscal element in relation to the second intradiscal element.

In some embodiments, the rotational movement resistance mechanism includes a first array of ridges provided on one of the first and second medial surfaces, and a second array of ridges provided on the other of the first and second medial surfaces, wherein the first and second arrays are configured such that ridges of the first array fall within corresponding ridge valleys of the second array to resist the relative rotational movement of the first intradiscal element in relation to the second intradiscal element.

In certain embodiments, the first and second arrays are provided on their respective medial surfaces at a location that at least in part encircles an axis of rotation of the relative rotational movement between the first and second intradiscal elements.

In some embodiments, the first and second arrays are provided in a circular pattern, with each of the individual ridge peaks of the first and second arrays being aligned with lines that emanate from the axis of rotation.

In certain embodiments, the first and second arrays are provided on substantially the entire surface area of the first and second medial surfaces, with each of the individual ridge peaks of the first and second arrays being aligned with lines that emanate from the axis of rotation.

In some embodiments, the first array is provided along a proximal portion of the first medial surface, and the second array is provided along a proximal portion of the second medial surface, which each of the individual ridge peaks of the first and second arrays being generally aligned with a longitudinal axis of the implant.

In certain embodiments, the first array is attached to a flexible member that enables the first array to be displaced away from the second array in response to the application of a force that causes the relative rotational movement between the first and second implants to occur and the ridges of the first array to be moved from the ridge valleys of the second array.

In some embodiments, the first and second arrays each includes two semi-circular portions that partially encircle the axis of rotation and that are on opposite sides of the axis of rotation, with each of the individual ridge peaks of the first and second arrays being aligned with lines that emanate from the axis of rotation.

In certain embodiments, the first array is provided on a post element extending from a center portion of one of the first and second medial surfaces, and the second array is provided in an aperture provided on the other of the first and second medial surfaces, the post element and the aperture adapted to be coupled together.

In some embodiments, each of the ridge peaks of the first array extend on the post element from a location near a proximal portion of the post element to a location near a distal portion of the post element, and each of the ridge peaks of the second array extend on an inner surface of the aperture from a location near the medial surface to a location deeper within the aperture.

In certain embodiments, the spinal implant further includes a rotational movement resistance mechanism adapted to resist rotational movement from a selected relative rotational position of the first intradiscal element in relation to the second intradiscal element.

In some embodiments, the rotational movement resistance mechanism includes a first borehole extending from a proximal surface of, to the medial surface of, one of the first and second intradiscal elements, and a second borehole extending from the medial surface of, and into, the other of the first and second intradiscal elements, the first and second boreholes being configured and aligned to receive an elongate member that extends from at least a portion of the first borehole and into at least a portion of the second borehole to affix the first intradiscal element in relation to the second intradiscal element in a first rotational orientation.

In certain embodiments, the rotational movement resistance mechanism further includes a third borehole extending from the medial surface of, and into, the other of the first and second intradiscal elements, the first and third boreholes being configured and aligned to receive an elongate member that extends from at least a portion of the first borehole and into at least a portion of the second borehole to affix the first intradiscal element in relation to the second intradiscal element in a second rotational orientation that is different from the first rotational orientation.

In some embodiments, the rotational movement resistance mechanism further includes a third borehole extending from a proximal surface of, to the medial surface of, the one of the first and second intradiscal elements, the third and second boreholes being configured and aligned to receive an elongate member that extends from at least a portion of the third borehole and into at least a portion of the second borehole to affix the first intradiscal element in relation to the second intradiscal element in a second rotational orientation that is different from the first rotational orientation.

In certain embodiments, the first borehole has a widened cross-section and is configured to engage the elongate element at different selected positions across a width of the borehole for select different rotational orientations between the first intradiscal element and the second intradiscal element.

In some embodiments, the second borehole further extends entirely through, and to the outer surface of, the other of the first and second intradiscal elements, thus providing for the elongate element to also extend into a vertebra.

In certain embodiments, the elongate member is a screw.

In some embodiments, each of the first and second intradiscal elements has formed therein at least one borehole adapted to receive a bone screw for affixing the intradiscal implant to an adjacent vertebra.

In certain embodiments, the first intradiscal element includes a first proximal flange portion that extends generally perpendicularly to a longitudinal axis of the first intradiscal element, and a first borehole extending through the flange portion from a proximal face to a medial side, wherein the first proximal flange portion is configured to be positioned against a side aspect of a first vertebra for receipt of a bone screw through the first borehole in a trajectory that is generally parallel with to the longitudinal axis of the first intradiscal element.

In some embodiments, the first intradiscal element includes a first borehole that extends from a first entry location provided in a first proximal surface portion located medial of a plane in which the first outer surface lies, the first borehole extending from the first entry location in a direction angled away from the first medial surface and to a first exit location provided on the first outer surface, and the second intradiscal element includes a second borehole that extends from a second entry location provided in a second proximal surface portion located medial of a plane in which the second outer surface lies, the second borehole extending from the second entry location in a direction angled away from the second medial surface and to a second exit location provided on the second outer surface.

In certain embodiments, the spinal implant and associate bones screws are adapted to not substantially protrude from the disc space when implanted in the disc space.

In some embodiments, the spinal implant further includes at least one anti-backout mechanism that is adapted to prevent a bone screw from backing out of the at least one borehole after installation of the bone screw.

In certain embodiments, the anti-backout mechanism is a circular canted coil spring, and the at least one borehole is a circumferential chamber in which the canted coil spring is housed.

In some embodiments, the first and second outer surfaces are ridged for secure engagement with the endplates of the adjacent vertebrae.

In certain embodiments, the first and second outer surfaces include spike elements for secure engagement with the endplates of the adjacent vertebrae.

In some embodiments, the first intradiscal element includes a first engagement mechanism adapted to be engaged by a distal tip of a first hand-held instrument, and the second intradiscal element includes a second engagement mechanism adapted to be engaged by a distal tip of a second hand-held instrument, the first and second engagement mechanisms being configured to provide the relative rotational movement when acted upon by the first and second hand-held instrument in opposite directions.

In certain embodiments, the at least one of the first and second engagement mechanisms is a threaded hole and elongate slot extending to each side of the threaded hole.

In some embodiments, at least one of the first and second intradiscal elements is tapered from a proximal end to a distal end.

In certain embodiments, at least one of the first and second intradiscal elements is tapered from a first side to a second side.

In some embodiments, the spinal implant further includes a cap configured to be placed on the first flange portion, the cap including holes formed in each side of the cap that align with the first borehole when the cap is placed on the first flange portion, the cap having a thickness in a medial portion selected to provide rotational pressure on a side of the vertebra to which the first flange portion is affixed.

In certain embodiments, the first and second intradiscal elements each have formed therein at least one fusion aperture extending from their respective outer surfaces to their respective medial surfaces, the at least one aperture in each of the first and second implants adapted to permit bone growth through the implant for spinal fusion.

In some embodiments, at least one of the first and second intradiscal elements has at least one viewing aperture extending from a side surface of the intradiscal element to one of the at least one fusion aperture, the at least one viewing aperture being configured to provide a view of bone growth through the fusion aperture through use of an imaging machine.

In certain embodiments, the spinal implant is generally rectangular.

In some embodiments, the spinal implant is sized and configured to extend laterally across a disc space, from one lateral aspect of the disc space to the opposite lateral aspect of the disc space.

In certain embodiments, the spinal implant has a cross-sectional shape in an axial plane that generally corresponds to the shape of the disc space.

In some embodiments, the spinal implant is sized and configured to be inserted into the disc space using an anterior approach.

In certain embodiments, the coupling mechanism of the spinal implant provides for the relative rotational movement about an axis at a center portion of the first and second medial surfaces.

In some embodiments, before implantation, the first intradiscal element is assembled with the second intradiscal implant.

In certain embodiments, the method further includes affixing each of the first and second intradiscal elements to respective adjacent vertebrae before the relative rotational movement is provided.

In some embodiments, the spinal implant further includes a rotational movement resistance mechanism adapted to resist rotational movement from a plurality of incremented relative rotational positions of the first intradiscal element in relation to the second intradiscal element.

In certain embodiments, the spinal implant further includes a rotational movement resistance mechanism adapted to resist rotational movement from the selected rotational orientation.

In some embodiments, the spinal implant is implanted in the disc space using a lateral approach to the spine.

In certain embodiments, the first and second intradiscal elements are engaged using at least one insertion instrument accessed to the spine using the lateral approach.

Embodiments can include one or more of the following advantages.

In some embodiments, the spinal implant is designed such that, after having been positioned as a unit within a disc space or during positioning in the disc space, the implant may be used to rotate the adjacent upper and lower vertebrae relative to one another, in one or more of an axial or transverse plane, a sagittal plane, or a coronal plane. In some examples, such relative rotation of adjacent vertebrae may be used to achieve de-rotation of a scoliosis patient's spine.

In certain embodiments, the first and second intradiscal elements are substantially bilaterally symmetric, such that either of the first and second intradiscal elements may serve as an upper or a lower intradiscal element.

In some embodiments, anti-backout mechanisms included within the spinal implant can prevent bone screws from backing out of the implant once the screws have been installed to secure the implant to adjacent vertebrae. Example anti-backout mechanisms include canted coil ring members adapted to seat within recesses of implant bores.

In certain embodiments, anti-migration features included within the spinal implant can increase the friction between the spinal implant and adjacent contact surfaces of the vertebral bodies, thereby minimizing movement or slippage of the implant with respect to the adjacent vertebrae after insertion between the adjacent vertebrae. Example anti-migration mechanisms include ridges disposed across the outer vertebrae-contacting surfaces of the implant and spike elements disposed at various positions across the outer vertebrae-contacting surfaces of the implant.

In some embodiments, visualization apertures included within the spinal implant allow a clinician to observe an extent of boney fusion within the fusion apertures via fluoroscopy or another medical imaging technology, unobscured by anterior and posterior sides of the intradiscal elements.

In some examples, the spinal implant may be provided in a number of appropriate sizes for different sized patients by varying one or more of an implant height, width, or length (that is, the combined height, width and length of both intradiscal elements in combination). In some instances, the implant may be sized for a particular patient. In some examples, the implant may be sized for implantation into any of the lumbar spine, the thoracic spine, or the cervical spine.

In certain embodiments, the intradiscal elements may be made of a magnetic material, which can generate an attractive force between the elements, such that conformity between complimentary features on inner mating surfaces of the elements is energetically favorable, and/or such that a displacement of the inner mating surfaces relative to one another requires a greater separation force than would otherwise be required if the material was non-magnetic.

Other features, aspects, and advantages will be apparent from the description, the drawings, and the claims.

DESCRIPTION OF DRAWINGS

Like reference symbols in the various drawings indicate like elements.

DETAILED DESCRIPTION

Figure 1:
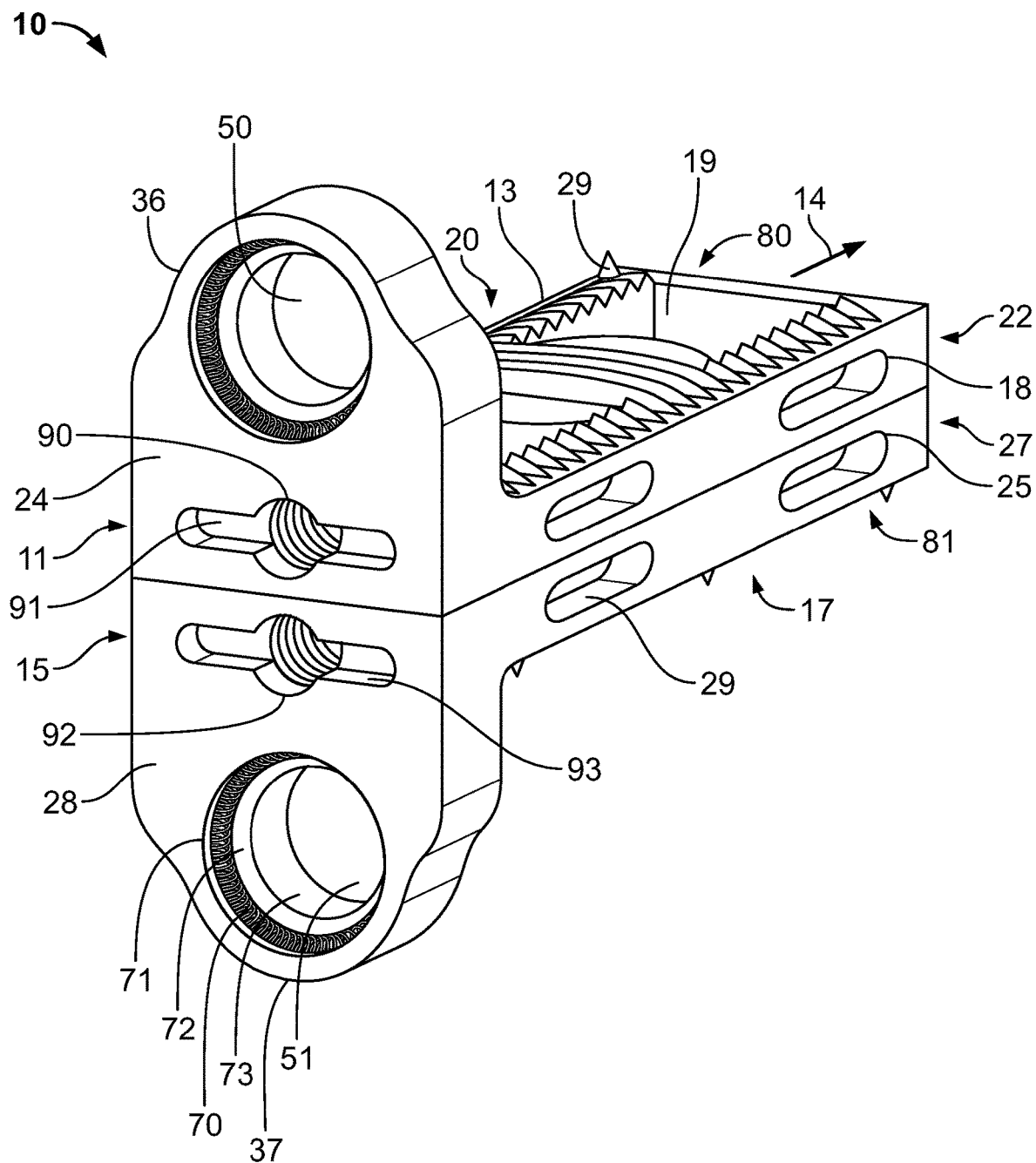
FIGS. 1-5 are various views that illustrate an embodiment of a spinal implant to achieve rotational adjustment of vertebrae.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary sill in the art having the benefit of this disclosure. The disc replacement system and related methods disclosed herein boasts a variety of inventive features and components that warrant patent protection, both individually and in combination.

In general, the spinal implants described in this document include a pair of rotatably-coupled intradiscal elements designed to be positioned as a unit within a disc space, between two adjacent vertebrae, and in a generally vertically stacked configuration. One of the intradiscal elements may engage or be affixed to an upper adjacent vertebra, while the other may engage or be affixed to a lower adjacent vertebra. The implant is designed such that, after having been positioned as a unit within a disc space or during positioning in the disc space, the implant may be used to rotate the adjacent upper and lower vertebrae relative to one another, in an axial or transverse plane, a sagittal plane, or a coronal plane. For example, one or both of the intradiscal elements may be rotated relative to one another in an axial or transverse plane, which in turn rotates, in the axial or transverse plane, affixed or engaged upper and lower vertebrae relative to one another. One reason such relative rotation of adjacent vertebrae may be desired is to accomplish de-rotation in a scoliosis patient's spine. De-rotation may be done in a patient at several levels of the spine.

FIGS. 1-5 illustrate such a spinal implant 10 according to a first embodiment. In this embodiment, the spinal implant 10 is a fusion type implant that facilitates fusion occurring between adjacent vertebrae following implantation of the implant 10 within a patient. In addition, the spinal implant 10 in this example will be described in the context of the implant 10 being designed to be inserted into the disc space using a lateral approach to the spine (that is, from the side of the patient). The implant 10 includes a first (upper) intradiscal element 11 and a second (lower) intradiscal element 15, with the two elements 11, 15 being designed to be rotatably coupled to one another and being designed to be positioned within a disc space as a unit and in a generally vertically stacked configuration. Although for clarity, one of the intradiscal elements is described as upper and the other is described as lower, it will be appreciated that in some embodiments each element 11, 15 may serve as the upper or lower intradiscal element.

The first intradiscal element 11 includes, firstly, a generally rectangular shaped intradiscal portion 80 that may be sized to extend laterally across a selected disc space. The intradiscal portion 80 includes a leading or distal end 22, which is the end of the element 11 that is intended to be inserted into a disc space first. The intradiscal element 11 also includes, at a proximal end 24 of the intradiscal portion 80, a trailing-end flange portion 36 that extends perpendicularly from the proximal end 24 of the rectangular shaped intradiscal portion 80. This flange portion 36, in general, enables both the fixation of the intradiscal element 11 to an adjacent vertebra and the rotational actuation of the intradiscal element 11 after the element 11 has been positioned within a disc space. The upper intradiscal portion 80 also includes a first (upper) surface 13 for engaging a first (upper) vertebra, a second (lower) surface 12 (see FIG. 2) that is opposite the upper surface 13 and adapted to be rotatably coupled to the second intradiscal element 15, an anterior side 18, and a posterior side 20 that is opposite the anterior side 18 (the anterior and posterior sides being named assuming a lateral approach to the spine from the right side of the patient).

Similar to the first intradiscal element 11, the second, or lower, intradiscal element 15 includes a generally rectangular shaped intradiscal portion 81, which in this embodiment is generally the same size and shape as the intradiscal portion 80 of the first intradiscal element 11. The second intradiscal element 15 also includes a trailing-end flange portion 37 disposed at a proximal end 28 of the generally rectangular intradiscal portion 81 and extending generally perpendicularly from the proximal end 28 of the generally rectangular shaped intradiscal portion 81. The flange portion 37 of the lower intradiscal element 15 extends perpendicularly in a direction oppose the flange portion 36 of the upper intradiscal element 11.

In the example of FIGS. 1-5, the intradiscal elements 11, 15 define oppositely facing vertebrae engaging surfaces 13, 17, respectively, that are generally planar and generally parallel to each other in this embodiment. In some embodiments, however, the vertebrae engaging surfaces 13, 17 may be non-parallel or tapered, such that inserting the implant 10 into an intradiscal space between adjacent vertebrae may modify the relative alignment of the vertebrae in one or both of the coronal plane and the sagittal plane of the spine. Furthermore, the surfaces 13, 17 may generally include one or more of a planar region, a concave region, and a convex region. Generally, the surfaces 13, 17 are symmetric to one another, such that the implant 10 can be inserted in a manner that allows either of the surfaces 13, 17 to engage either of the first (upper) and second (lower) vertebrae while providing the same effect. Similarly, anterior sides 18, 25 and posterior sides 20, 26 of the intradiscal elements 11, 15 are generally symmetric to each other such that the spinal fusion implant 10 can be inserted from either of a left or right side of the patient.

The flange portions 36, 37 enable the implant 10 to be secured to adjacent first and second vertebrae. In some embodiments, the implant 10 may include multiple flange portions extending from the surfaces 13, 17, where the multiple flange portions are substantially similar in function to the flange portions 36, 37. Furthermore, a spinal fusion implant may include flange portions of various sizes and/or shapes to facilitate implantation or fixation of the implant. In the example of FIGS. 1-5, the flange portions 36, 37 include rounded corners (i.e., the flange portions 36, 37 are generally D-shaped); however, the flange portions 36, 37 may generally take on any number of suitable shapes, such as, a square, a triangle, a semi-circle, or a partial oval. Surfaces of the flange portions 36, 37 may be, in various embodiments, one or more of generally concave, generally convex, and generally planar.

Figure 2:
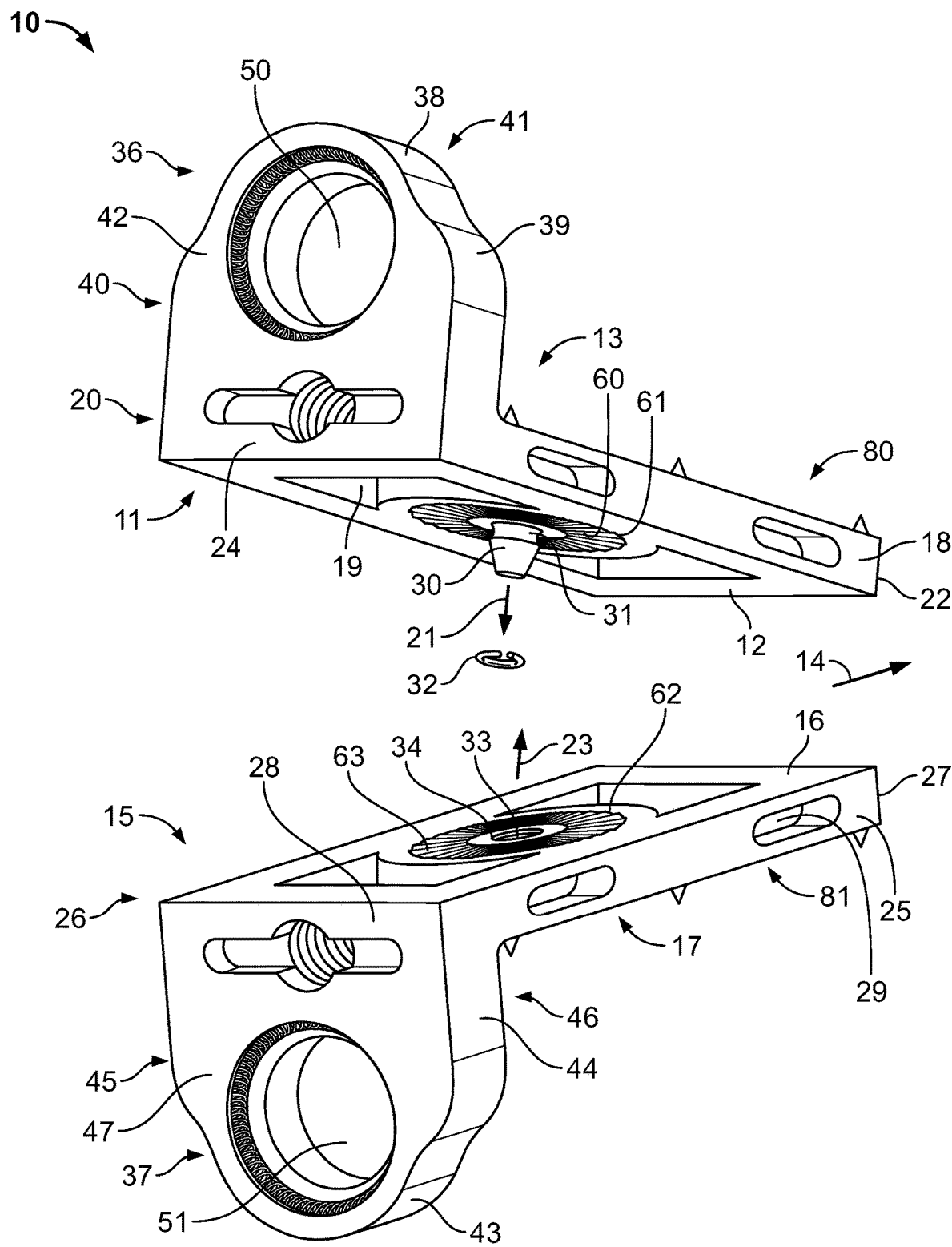

Referring particularly to FIG. 2, the flange portion 36 of the upper element 11 is defined by a generally rounded upper perimeter surface 38, an anterior side 39 (right side in FIG. 2), a posterior side 40 (left side in FIG. 2), a medial or back side 41 that faces a vertebra when implanted, and a lateral or front side 42 that is opposite the medial side 41. The flange portion 37 of the lower element 15 is defined by a similar generally rounded lower perimeter surface 43, an anterior side 44 (right side), a posterior side 45 (left side), a medial side 46 (back side), and a laterally facing side 47 (front side). The front side 47 is referred to as a laterally facing side, assuming the implant is inserted using a lateral approach, and the front side 47 would therefore face laterally (the patient's side) from the spine. The anterior sides 39, 44 and posterior sides 40, 45 are generally symmetric to each other, respectively, such that the implant 10 can be inserted from either of the left or right side of the patient. Generally, the medial or back sides 41, 46 of the flanges 36, 37 are configured to engage lateral aspects of the first and second vertebrae, respectively. As shown in FIGS. 1 and 2, the medial sides 41, 46 of the flange portions 36, 37 are generally planar and perpendicular to a longitudinal axis 14 of the spinal fusion implant 10. Alternatively, the medial or back sides 41, 46 may be generally concave or generally convex, and may form acute or obtuse angles with the longitudinal axis 14 of the implant 10. The laterally facing or front sides 42, 47 of the flange portions 36, 37 are generally planar and perpendicular to the longitudinal axis 14 of the implant 10. Alternatively, the laterally facing or front sides 42, 47 may be generally concave, generally convex, or any combination of concave, convex, and planar.

In the example embodiment of FIG. 2, the flange portions 36, 37 are configured such that laterally facing sides 42, 47 are the proximal ends 24, 28 of the intradiscal elements 11, 15. Alternatively, the laterally facing sides 42, 47 may be positioned medial to the proximal ends 24, 28. In the example embodiment of FIG. 2, a width of the flange portion 36 (as measured from the anterior side 39 to the posterior side 40) is substantially equal to a width of the first intradiscal element 11 (as measured from the anterior side 18 to the posterior side 20). Similarly, a width of the flange portion 37 (as measured from the anterior side 44 to the posterior side 45) is substantially equal to a width of the second intradiscal element 15 (as measured from the anterior side 25 to the posterior side 26). Alternatively, the widths of the flange portions 36, 37 may be unequal to the widths of the intradiscal elements 11, 15, respectively.

Figure 3:
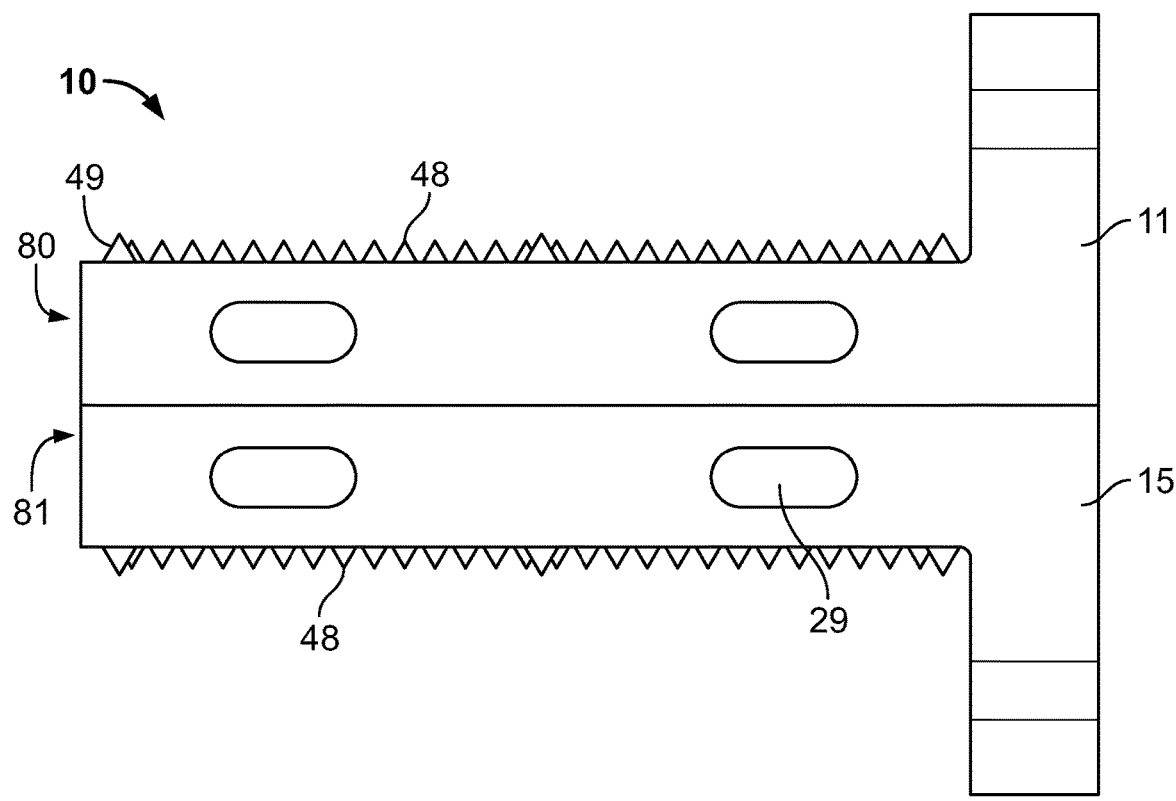
Figure 4:
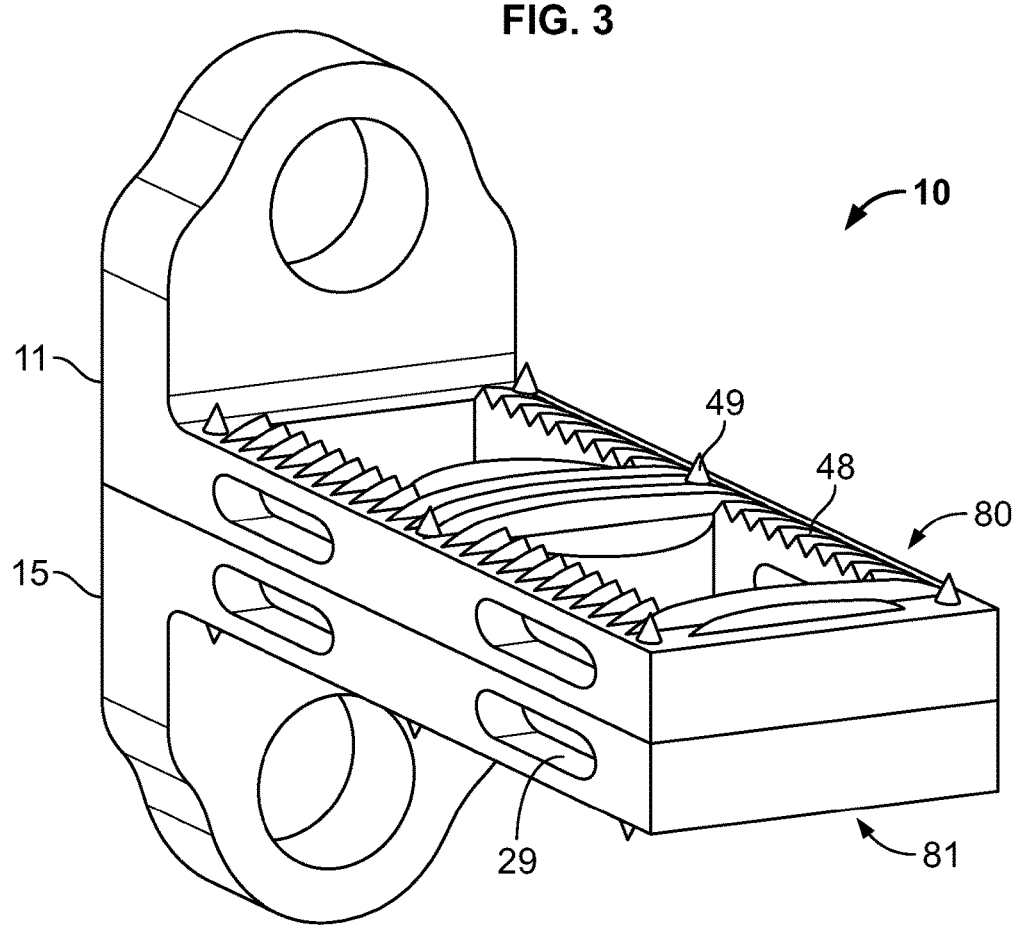
Figure 5:
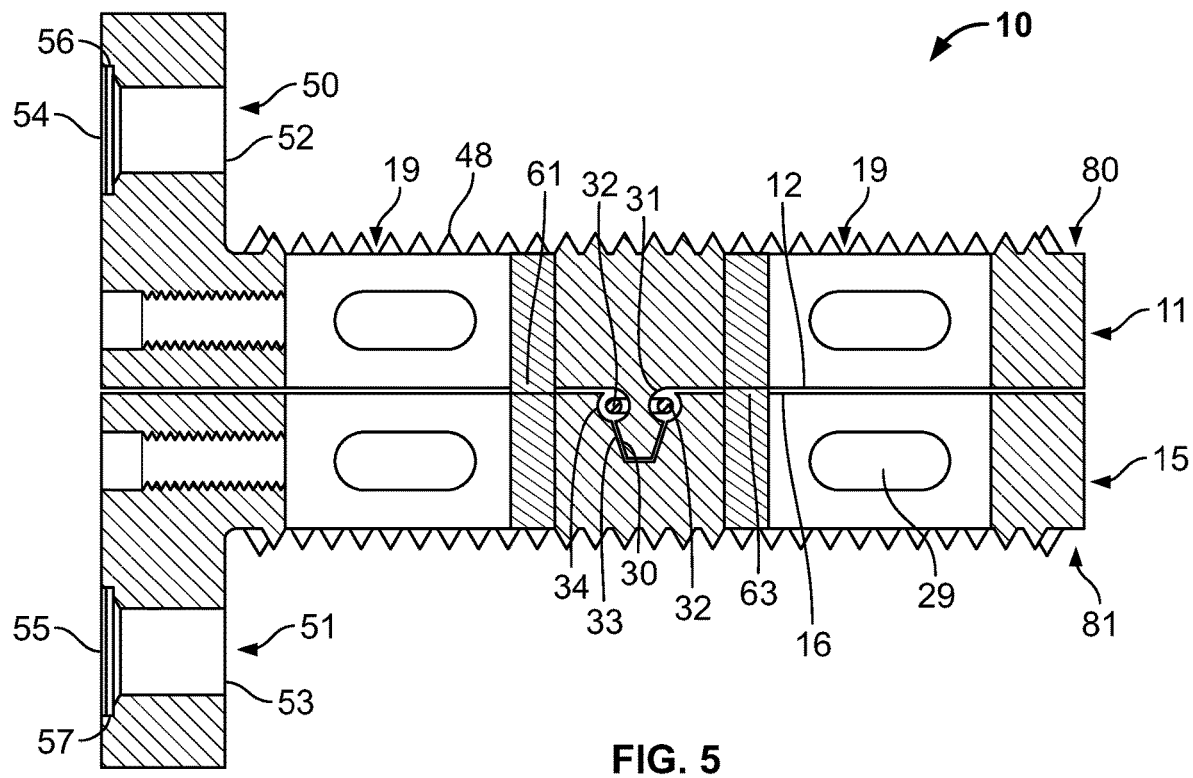
Figure 6:
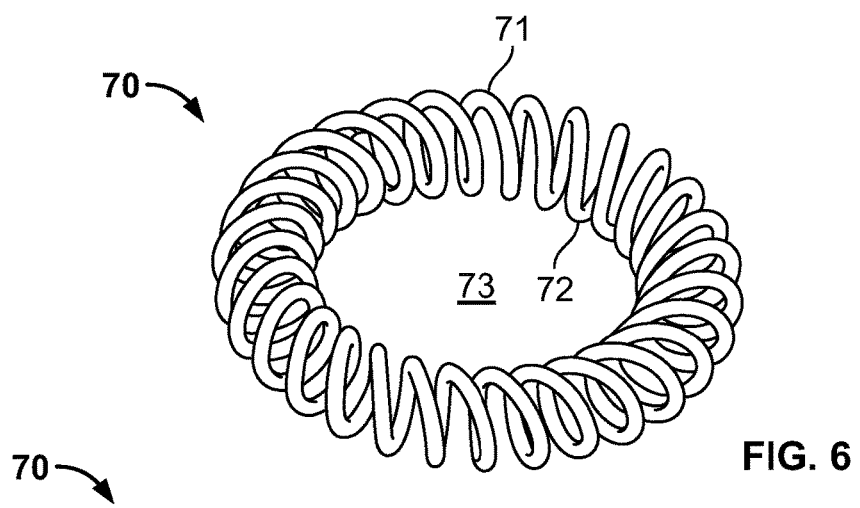
FIGS. 6-7 illustrate details of a mechanism that may be used in spinal implants disclosed in this document to prevent back-out of bone screws.
Figure 7:
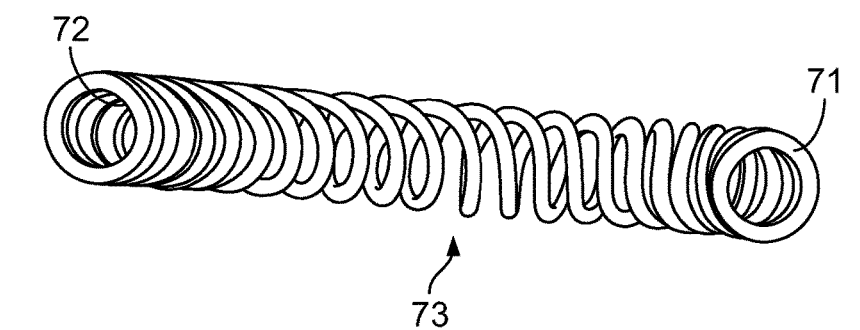

Each of the flange portions 36, 37 includes, in this embodiment, one axial bore or bone screw receiving hole (bore 50 for flange 36 and bore 51 for flange 37) that extends entirely through the respective flange portion 36, 37, from the front or laterally facing side 42, 47 to the medial or back side 41, 46. The central longitudinal axes of the two bores 50, 51 may be generally parallel to the longitudinal horizontal axis 14 of the spinal fusion implant 10, as illustrated in FIGS. 1-5. Alternatively, the central longitudinal axes of the two bores 50, 51 may be angled or in other words form acute or obtuse angles with respect to the longitudinal horizontal axis 14 of the implant 10. In some embodiments, the axes of the bores 50, 51 form an angle, for example between zero and 15° with respect to the implant's longitudinal axis 14. Referring particularly to FIG. 5, a medial or backside opening 52 of the first element's bore 50 has a diameter smaller than that of a front-side or laterally facing opening 54 of the bore 50, and a medial or backing opening 53 of the second element's bore 51 has a diameter smaller than that of a front-side or laterally facing opening 55 of the bore 51, such that the inside of the laterally facing openings 54, 55 each have a circular seat extending around the entire circumference the openings 54, 55 for receiving an enlarged screw head region of a bone screw. During a procedure for implanting the spinal implant 10, an appropriate method may be used for surgically approaching the spine, such as a lateral approach technique, and for securing the flange portions 36, 37 to the first and second vertebrae using bone screws. In particular, after a surgical corridor to the spine is established, the appropriate disc may be removed, and the spinal fusion implant 10 may then be inserted between adjacent vertebrae. Then a first bone screw may be drilled through the upper element's bore 50 and into the first or upper vertebra to secure the upper element's flange portion 36 to the upper vertebra, and a second bone screw may be drilled through the lower element's bore 51 and into the lower vertebra to secure the lower element's flange portion 37 to the lower vertebra. A user may then rotate the first intradiscal element 11 relative to the second intradiscal element 15 (and in an axial or transverse plane) to achieve a desired relative alignment between the upper and lower vertebrae and/or a desired relative alignment between the vertebrae and the normal axial plane of the spine.

A number of anti-backout mechanisms for the bone screws may be provided at or near the laterally facing or front-side end of the bores 50, 51. FIGS. 1, 2, 6 and 7 illustrate an example of a locking element 70 according to one embodiment. The locking element 70 is provided as a generally circular canted coil ring member. Referring to FIG. 5 (locking element 70 omitted for clarity), the bores 50, 51 include locking element recesses 56, 57 located adjacent to the laterally bore's facing or front-side openings 54, 55, respectively. The recesses 56, 57 are each dimensioned to receive and retain one locking element 70. The locking element 70 has an outer diameter 71 and inner diameter 72, and defines an aperture 73 therethrough (see FIGS. 2, 6, and 7). Due to the canted coil nature of the locking element 70, each of the diameters 71, 72 are independently variable. For example, when inserted into the recess 56, 57 of the bore 50, 51, the outer diameter 71 may be reduced due to being forced inwardly by a rigid circumference of the recess 56, 57.

Referring again to FIG. 2, upon insertion of a bone screw through the flange's bore 50 and thus through the aperture 73 of the locking element 70, the inner diameter 72 of the locking element 70 may be forced to expand to accommodate the passage of an enlarged, preferably tapered, head region of the bond screw (e.g., a region of the bone screw having an enlarged diameter relative to that of the threaded shank). For example, a head of the bone screw may include such a ledge region. The expansion of the inner diameter 72 occurs independently from the variation of the outer diameter 71, and thus may occur without any expansion of the outer diameter 71, which is prevented from expanding by the rigid nature of the recesses 56, 57 in which the locking element 70 is retained. Once the enlarged head region of the bone screw passes through the locking element's aperture 73, the inner diameter 72 contracts at least partially back to its original dimension such that at least a portion of the screw head is covered by the locking element 70, thereby retaining the bone screw and preventing it from backing out. The locking element 70 may be formed from any suitable biocompatible material, such as a metal (e.g., titanium, stainless steel, etc).

Accordingly, upon insertion of an appropriately sized bone screw into the bore 50, 51, the bone screw applies an outward force upon the locking element 70, causing the inner diameter 72 of the locking element 70 to expand and thus allow passage of a head portion of the bone screw therethrough. As an enlarged portion of the head passes through the inner diameter 72 of the locking element 70, the outward force applied by the screw head on the locking element 70 decreases, and the inner diameter 72 of the locking element 70 retracts at least partially to its original size. In this position, the locking element 70 covers at least a portion of the bone screw head such that the head is prevented from passing back through the locking element 70 (as it could absent the force, which, for example, could be provided in a revision procedure using an appropriate tool). Thus, the locking element 70 engages a portion of the head of a bone screw to provide an anti-backout mechanism for the bone screw.

The spinal fusion implant 10 in this embodiment further includes anti-migration features designed to increase the friction between the spinal fusion implant 10 and adjacent contact surfaces (e.g., end plates) of the vertebral bodies, thereby minimizing movement or slippage of the implant 10 with respect to the adjacent vertebrae after insertion between the adjacent vertebrae. Referring particularly to FIGS. 3 and 4, anti-migration features include ridges 48 disposed across the outer vertebrae-contacting surfaces 13, 17 of the implant 10. These ridges 48 in this embodiment extend generally perpendicular to the horizontal longitudinal axis 14 of the implant 10. Alternatively, the ridges 48 may extend in another direction relative to the axis 14. In this embodiment, the ridges 48 extending from the upper element's upper surface 13 are bilaterally symmetric to the ridges 48 extending from the lower element's bottom surface 17, as illustrated in FIG. 3. Alternatively, the ridges 48 extending from the upper surface 13 may not be bilaterally symmetric to the ridges 48 extending from the lower surface 17. In some embodiments, the ridges 48 may be biased or ratcheted, such that the ridges 48 substantially prevent slippage in a particular direction.

Still referring to FIGS. 3 and 4, in this embodiment anti-migration features of the implant 10 also include spike elements 49 disposed at various positions across the implant's outer surfaces 13, 17. Here, the implant 10 includes six spike elements 49 disposed along each of the outer surfaces 13, 17. The spike elements 49 may be manufactured from one or more of a variety of suitable materials, including a metal, a ceramic, and a polymer (preferably a material having radiopaque characteristics). In some embodiments, one or more of the spike elements 49 may be located on either of the medial or back-side surfaces 41, 46 of the flange portions 36, 37. In some embodiments, the spike elements 49 may extend from the upper element's bottom surface 12, through the upper element 11 and beyond its upper surface 13, and similarly, from the lower element's upper surface 16, through the lower element 15 and beyond its bottom surface 17. Alternatively, the spike elements 49 may have a shorter depth and extend from a position between the upper element's bottom and upper surfaces 12 and 13 or from a position between the lower element's upper and bottom surfaces 16 and 17. In a general embodiment, the spike elements 49 have radiodense characteristics. Accordingly, the implant 10 is manufactured, at least in part, from a radiolucent material (such as, poly-ether-ether-ketone (PEEK) or poly-ether-ketone-ketone (PEKK)), and the spike elements 49 can be observed using X-ray imaging or fluoroscopy such that a surgeon can track the position of the implant 10 and the degree of rotation of the upper intradiscal element 11 relative to that of the lower intradiscal element 15 during and after implantation.

Referring again to FIG. 1, the intradiscal elements 11, 15 each includes two large fusion apertures 19 extending through the rectangular portions 80, 81 from the lower surface 13 to the upper surface 12 of the upper intradiscal element 11, and from the upper surface 16 to the lower surface 17 of second intradiscal element 15, respectively. The fusion apertures 19 provide regions for carrying bone growth material along with the implant 10, which then assists in the creation of bony fusion between the first and second vertebrae. Furthermore, the intradiscal elements 11, 15 each include four visualization apertures 29, two apertures 29 extending from the anterior sides 18, 25 of the intradiscal elements 11, 15 (one aperture 29 in each side 18, 25) to their respective fusion apertures 19, and two apertures 29 extending from the posterior sides 20, 26 of the intradiscal elements 11, 15 to the respective fusion apertures 19 (and again, one aperture 29 in each side 20, 26). The visualization apertures 29 allow a clinician to observe an extent of boney fusion within the fusion apertures 19 via fluoroscopy or another medical imaging technology, unobscured by the anterior sides 18, 25 or the posterior sides 20, 26 of the intradiscal elements 11, 15.

In some examples, fusion of the first and second vertebrae may be improved by placing various osteoinductive materials in the fusion apertures 19 and/or adjacent to the spinal fusion implant 10. Such osteoinductive materials may be introduced before, during, or after the insertion of the spinal fusion implant 10. Example osteoinductive materials include autologous bone harvested from the patient, a bone allograft, a bone xenograft, non-bone implants (e.g., a ceramic, a metal, or a polymer), bone morphogenic protein, and bioresorbable materials (e.g., poly (D,L-lactide-co-glycolide)-based polymers).

The spinal fusion implant 10 may be provided in a number of appropriate sizes for different sized patients by varying one or more of an implant height, width or length (that is, the combined height, width and length of both intradiscal elements 11, 15 in combination). In some embodiments, the intradiscal elements 11, 15 have a length in the range of 30-60 mm. In some embodiments, the intradiscal elements 11, 15 have a width in the range of 15-25 mm. In some embodiments, the implant 10 has an implant height in the range of 5-20 mm. Such lengths, widths, and implant height ranges are generally appropriate for implantation of the implant 10 into the lumbar region of the spine. In some examples, the implant 10 may be sized for a particular patient. Furthermore, the implant 10 may be alternatively sized for implantation into either of the thoracic spine or the cervical spine.

The spinal fusion implant 10 includes a number of features for engaging insertion and de-rotation instruments. As illustrated in FIG. 1, one engagement feature includes threaded receiving apertures 90, 92 extending from the proximal ends 24, 28 of the first and second intradiscal elements 11, 15. In the FIG. 1 embodiment, the upper intradiscal element 11 has one such aperture 90, and the lower intradiscal element also has one such aperture 92. Associated with the apertures 90, 92 are slots 91, 93 that each extends laterally from both sides of each one of the apertures 90, 92. The apertures 90, 92 and corresponding slots 91, 93 are sized to engage with a distal end of a correspondingly designed insertion and/or rotation instrument. After the implant 10 has been implanted and secured to the vertebrae, with, for example, bone screws, the first and second vertebrae can be de-rotated using, for example, a pair of elongate instruments. For example, a user may engage threaded ends of elongate insertion instruments into the receiving apertures 90, 92 (and optionally distal rails positioned to the sides of the threaded ends into the slots 91, 93). The user can then incrementally rotate the first and second intradiscal elements 11, 15 relative to one another by laterally separating proximal ends of the two insertion instruments. Accordingly, a separation force can be applied in opposing directions that are generally co-planar with the implant's facing surfaces 12, 16 (that is, separating the instruments to the sides, for example, to achieve rotation in an axial plane.

Referring to FIGS. 2 and 5, the first intradiscal element 11 can be rotated in an axial plane with respect to the lower intradiscal element 15 by providing a post element 30 extending from a generally central portion of the medial surface 12 of the first intradiscal element 11 while also providing a corresponding aperture 33 in a generally central portion of the medial surface 16 of the second intradiscal element 15. The post element 30 engages into the aperture 33, and the post element 30 and aperture 33 serve as the axis of the axial rotation between the two intradiscal elements 10, 15. In particular, as illustrated in FIG. 2, the post element 30 projects outwardly and perpendicularly from the medial or bottom surface 12 of the first intradiscal element 11, and projects generally from a center portion of the medial surface 12. The post element 30 includes a bulbous end portion, and proximal of the end portion includes a circumferential groove 31 sized to receive a snap-ring 32 in a biased configuration. The aperture 33 is formed in the medial surface 16 of the second intradiscal element 15, and is formed generally in a center portion of the medial surface 16. The snap-ring 32 is sized to be received and engaged within a circumferential groove 34 formed within the aperture 33. In the example of FIG. 2, the post element 30 and the intradiscal element 11 may be formed as a single component. Alternatively, in some embodiments, the post element 30 may be a separate component that engages an appropriately sized recess in the first intradiscal element 11, for example by providing the post element 30 with a threaded shank sized to fit within a threaded bore in the surface 12 of first intradiscal element 11. In some embodiments, the post element 30 may alternatively be disposed on the medial surface 16 of the second intradiscal element 15, and the aperture 33 may alternatively extend from the medial surface 12 of first intradiscal element 11.

Referring now to FIG. 5, the snap-ring 32 is dimensioned to be received within a circumferential space located between the circumferential groove 31 of the post element 30 and the circumferential grove 34 of the aperture 33. The snap-ring 32 may be made of any appropriate bio-compatible material, such as a metal (e.g., titanium or stainless steel). Furthermore, the snap-ring 32 is sufficiently flexible (i.e., terminal ends of the snap ring 32 can be separated laterally) such that the snap-ring 32 can be forced to snap into the complementary grooves 31, 34 without being permanently deformed.

In the example of FIGS. 1 and 2, the medial surfaces 12, 16 are generally planar. In other embodiments, however, the surfaces 12, 16 may be non-planar. For example, the upper element's medial surface 12 may be concave, and the lower element's medial surface 16 may be convex in a complementary fashion. Alternatively, the upper element's medial surface 12 may form a protruding cone, while the lower element's medial surface 16 may form a complimentary, recessed cone. In some embodiments, the medial surfaces 12, 16 may be frustoconical. In some embodiments, the medial surfaces 12, 16 may be multi-level, or multi-tiered, including several mating surfaces that may be one or more of planar, convex, concave, conical, and frustoconical. The medial surfaces 12, 16 may further include features such as spikes, ridges, posts, rails, or humps that engage complimentary recessed channels, cutouts, chambers, or valleys in the opposing medial surface 12, 16 to provide for incremental rotation in an axial plane of the intradiscal elements 11, 15 relative to one another, or to provide increased stability of the assembled implant 10. In certain embodiments, the upper element's medial surface 12 may include one or more semi-circular projections that slidably engage respective complementary, semi-circular channels in the lower element's medial surface 16.

Referring to FIGS. 2 and 5, the medial surface 12 of the upper intradiscal element 11 includes a circular array of ridges 60 that includes several ridges 61, and that generally encircles the post element 30. Each ridge 61 extends substantially perpendicularly to a longitudinal axis 21 of the post element 30, and in a plane generally parallel with the plane of the medial surface 12. The medial surface 16 of the lower intradiscal element 15 includes a similar array of ridges 62 that includes several ridges 63, and that generally encircles the aperture 33. Each ridge 63 extends substantially perpendicularly to a longitudinal axis 23 of the aperture 33, and in a plane generally parallel with the plane of the medial surface 16. In the example of FIGS. 2 and 5, the ridges 61, 63 are triangular in cross-section, such that each ridge 61 forms a triangular prism or a triangular frustum, wherein the base of each ridge 61, 63 is substantially co-planar with the medial surface 12, 16 from which the ridge 61, 63 extends. In some embodiments, the ridges 61, 63 may be mounted on a surface that is slightly recessed from, but co-planar with, the medial surfaces 12, 16 such that only a portion of the ridges 61, 63 protrudes beyond the respective medial surface 12, 16. Furthermore, the ridges 61, 63 are substantially evenly spaced from one another, such that, in cooperation, the ridges 61, 63 provide for consistent incremental rotation.

In some embodiments, the ridges 61, 63 may be formed such that rotation is biased, or ratcheted, to favor one rotational direction versus the other rotational direction (i.e., clockwise versus counterclockwise) such that when the implant 10 is assembled, rotating the first intradiscal element 11 relative to the second intradiscal element 15 about the post 31 requires substantially more force in one rotational direction (e.g., clockwise) than in the other direction (e.g., counterclockwise). Alternatively, the ridges 61, 63 may be formed such that rotation is possible in only one direction (e.g., clockwise). In addition to the arrays of ridges 60, 62, either or both of the intradiscal elements 11, 15 may be formed at least in part from a magnetic material such that additional resistance to rotation is provided by resulting magnetic attractive forces between the intradiscal elements 11, 15. The magnetic attractive forces may further provide conformity between the medial surfaces 12, 16 after the implant 10 has been implanted.

The snap-ring 33 is sized to allow an appropriate degree of flexibility between the first and second intradiscal elements 11, 15. Furthermore, the arrays of ridges 60, 62 are sized such that when the medial surfaces 12, 16 are brought into contact with one another and the post element 30 is accordingly disposed within the aperture 33, each individual ridge 61 extending from the first intradiscal element 11 is engaged between two individual ridges 63 extending from the second intradiscal element 15. Simultaneously, each individual ridge 63 extending from the second intradiscal element 15 is engaged between two individual ridges 61 extending from the first intradiscal element 11 such that the array of ridges 60 is interdigitated with the array of ridges 62 in several different rotational orientations of the first intradiscal element 11 relative to the second intradiscal element 15. This "stacked poker chip" arrangement allows the user to rotate the first intradiscal element 11 incrementally relative to the second intradiscal element 15 after the implant 10 has been inserted into the intervertebral space and affixed to the adjacent vertebrae by inserting bone screws through the flange portions 36, 37. For example, a pair of ridge arrays with 36 evenly-spaced ridges (36 troughs) allows the first intradiscal element 11 to be rotated in ten degree increments relative to the second intradiscal element 15, while a pair of ridge arrays with 72 evenly-spaced ridges (72 troughs) allows the first intradiscal element 11 to be rotated in five degree increments relative to the second intradiscal element 15.

The arrays of ridges 60, 62 can have different diameters than is shown in FIG. 2. For example, a larger array diameter may accommodate a larger number of ridges and thus provide finer rotational increments, and a smaller array diameter may allow for larger fusion apertures. In some embodiments, the arrays of ridges 60, 62 may have an inner diameter that is larger than the width of the implant 10 (i.e., the distance between the anterior surfaces 18, 25 and posterior surfaces 20, 26) such that the arrays of ridges 60, 62 may form arcuate or semi-circular segments, instead of the circular arrays shown in FIG. 2. Such an alternative embodiment will be discussed in further detail below.

The spinal implant 10 may be made of any suitable bio-compatible material. In some embodiments, the spinal fusion implant 10 may be made of one or more non-bone materials having suitable radiolucent characteristics, including polymer compositions, such as PEEK, PEKK, or any combination of PEEK and PEKK. In certain embodiments, the spinal fusion implant 10 may be made of a biologically inert material, such as any metal that is customarily used for implantable medical devices. Example biologically inert materials include titanium, stainless steel, and polymer and metal combinations. In some embodiments, the spinal fusion implant 10 may be made of a combination of bio-compatible materials. The anchoring mechanism (for example, plates) may be made primarily of a polymer material, and may include extending flanges that may be made of metal. Alternatively, the spinal fusion implant 10 may be made entirely of metal.

In certain embodiments, the intradiscal elements 11, 15 may be made of a magnetic material. The magnetic material can generate an attractive force between the elements 11, 15, such that conformity between complimentary features on inner mating surfaces 12, 16 of the elements 11, 15 is energetically favorable, and/or such that a displacement of the surfaces 12, 16 relative to one another requires a greater separation force than would otherwise be required if the material was non-magnetic. In a general embodiment, both inner mating surfaces 12, 16 of the intradiscal elements 11, 15 are made of a magnetic material, and the surfaces 12, 16 have opposite magnetic polarities.

Figure 9:
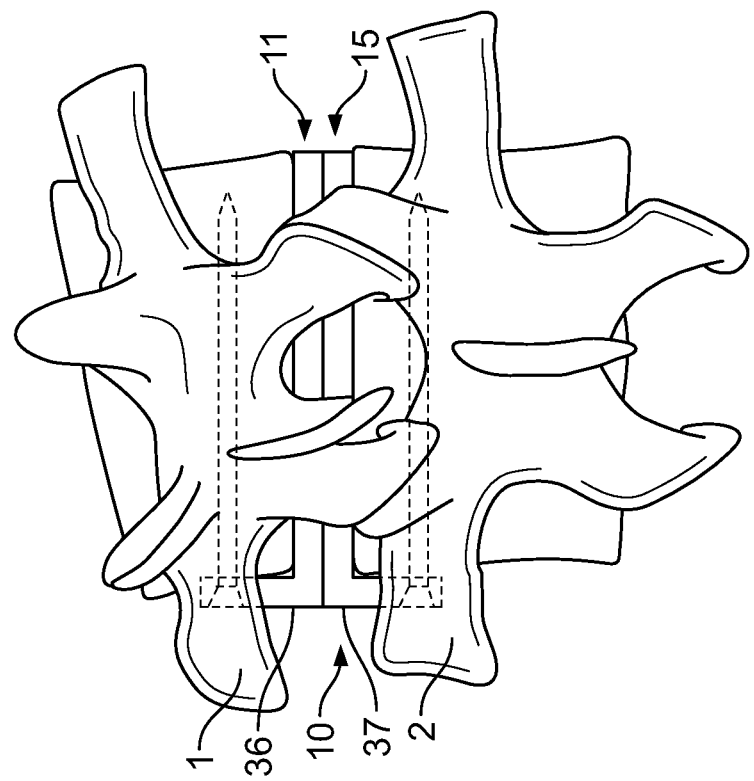
FIGS. 8-10 illustrate a portion of a human spine and an example method in which spinal implants disclosed in this document are used.
Figure 8:
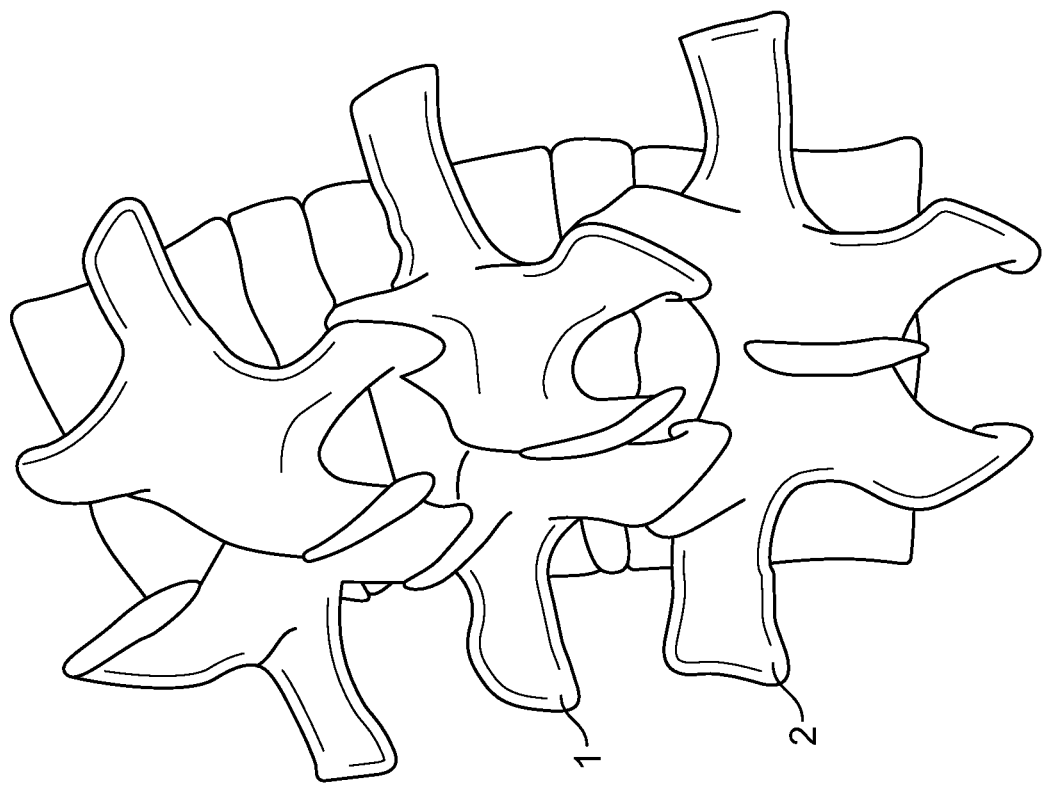
Figure 10:
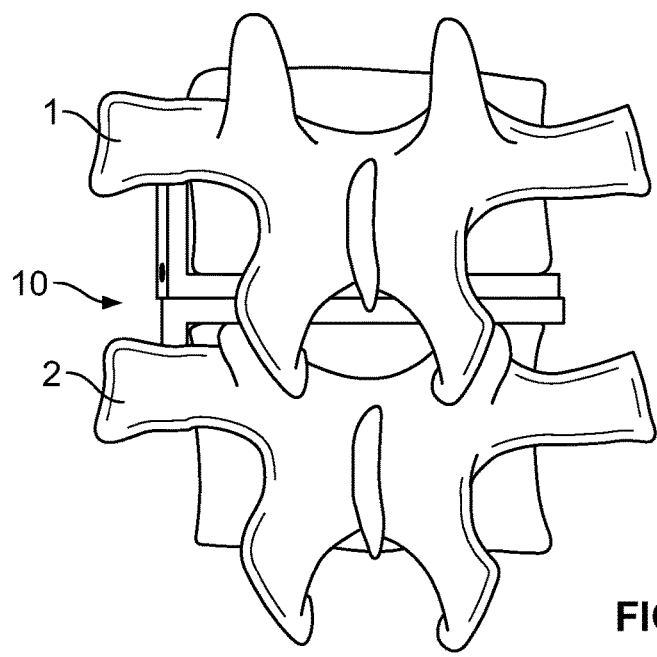

FIGS. 8-10 illustrate a method of using the spinal fusion implant 10. FIG. 8 illustrates a portion of a deformed spine wherein the middle vertebra 1 is rotated abnormally in both of the axial (i.e., transverse) and coronal planes relative to the lower adjacent vertebra 2. In FIG. 9, the intervertebral disc between the middle and lower vertebrae (upper-most vertebra omitted for clarity) has been at least partially removed and replaced with the implant 10. In this example illustration, the spine is approached laterally, and the flange portions 36, 37 are affixed to lateral faces of the vertebrae with, for example, bone screws (shown in hidden lines). In this example illustration, the vertebra-contacting surfaces 13, 17 of the implant 10 are oriented such that planes defined by the vertebra-contacting surfaces 13, 17 converge at a point beyond the distal ends 22, 27 of the intradiscal elements 11, 15, or in other words, the intradiscal elements 11, 15 are tapered, such that the height of the elements 11, 15 linearly reduces from the proximal end to the distal end. With appropriate height between, and angulation of the vertebra-contacting surfaces 13, 17, once inserted and affixed to the vertebrae 1, 2 at an appropriate height and orientation, the implant 10 can restore a correct alignment of the vertebrae 1, 2 in the coronal plane. Next, as illustrated in FIG. 10, the first intradiscal element 11 may be rotated counter-clock wise relative to the second intradiscal element 15 to correct the alignment of the adjacent vertebra 1, 2 in the axial plane (i.e., to "de-rotate" the vertebrae 1, 2). In some embodiments (not shown), the implant 10 may be further configured to modify the angulation between the first and second vertebrae in the sagittal plane (e.g., to restore normal lordosis in the lumbar spine), for example by utilizing an appropriate degree of tapering in the implant, from the anterior side to the posterior side, or vice-versa.

In many cases of spinal deformity, multiple spinal fusion implants 10 may be required to adequately correct the abnormal curvature of the spine. In some examples, the spine may be surgically approached using a lateral approach technique, which involves making an incision in the side of the patient. The discs located within a portion of the spine that has abnormal curvature are then identified and removed using conventionally known techniques in the art. Furthermore, one or more retaining rods can be shaped and prepared by the surgeon to stabilize the re-aligned spine. The retaining rod can be cut to a desired length and bent to a desired shape anticipated for a correct alignment. The retaining rod is secured directly to the vertebrae, for example, to the pedicle region using a bone screw from a posterior or posterior-lateral approach. Alternatively, the retaining rods can be secured to one or more of the implants 10, either supplementing or substituting for direct attachment of the rods to the vertebrae. The retaining rods may be secured to the implant 10, by, for example, using a connector element having a proximal threaded shaft and a distal rod-clamp (e.g., a "tulip connector"), where the threaded shaft is sized to engage the engagement apertures 90, 92, and the rod-clamp is sized to receive a region of the retaining rod. Several rods and connector types are known in the art. In some examples, one or both of rod clamps and cable guides can be secured to the bores 50, 51 and may be attached via the bone screws that pass there-through and into the adjacent vertebrae.

Figure 11:
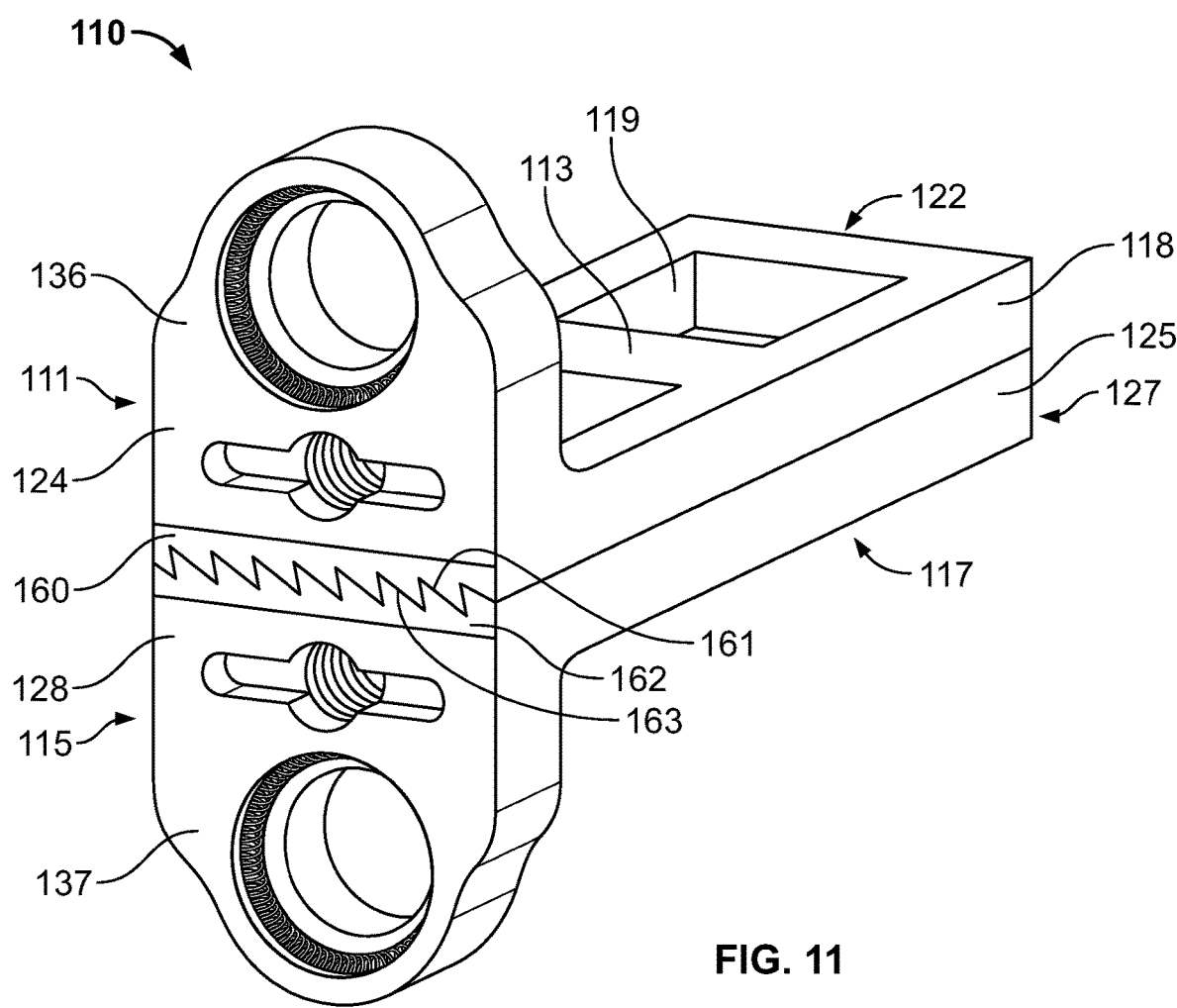
FIGS. 11-12 are various views that illustrate another embodiment of a spinal implant to achieve rotational adjustment of the spine.
Figure 12:
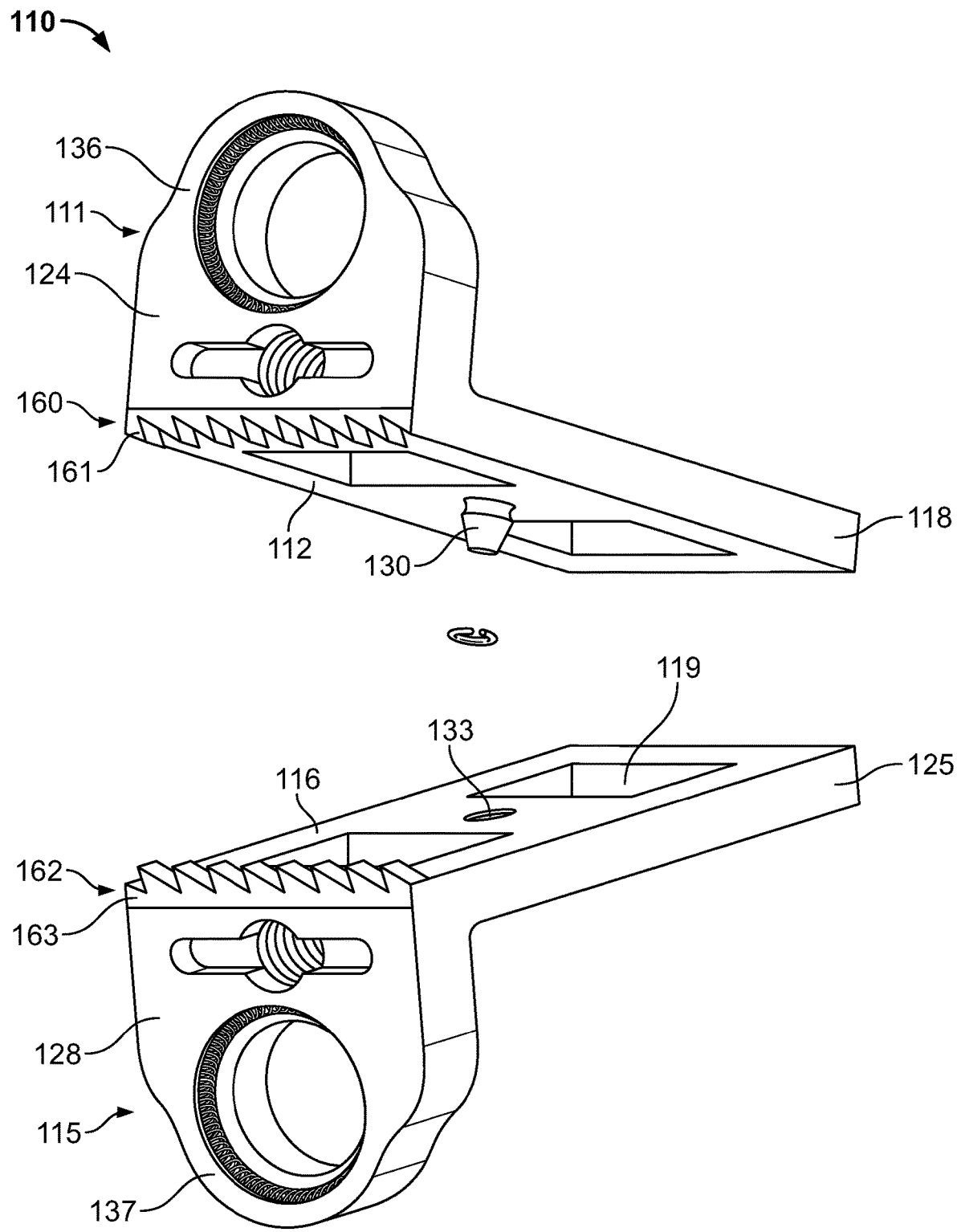
Figure 13:
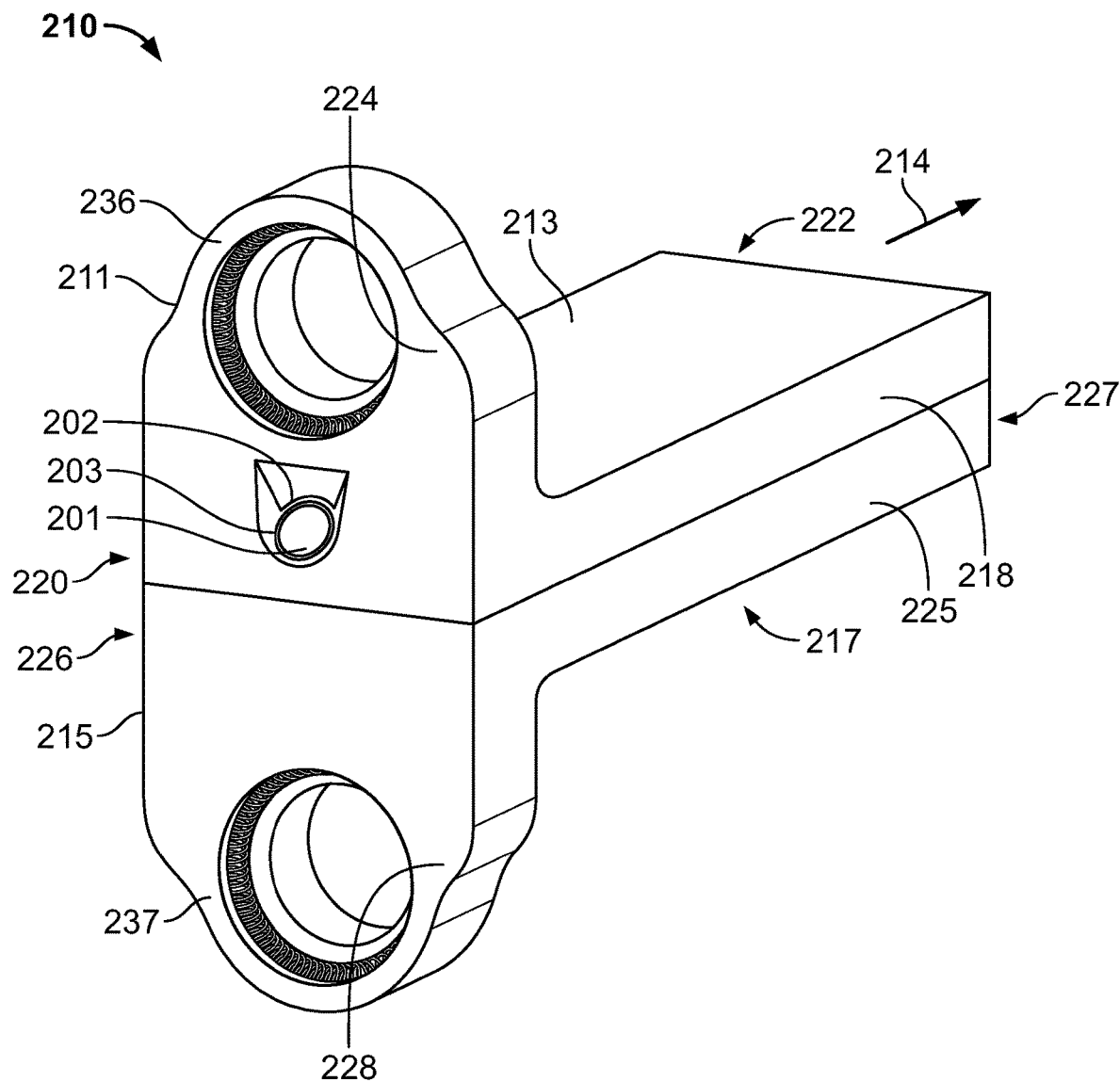
FIGS. 13-16 are various views that illustrate yet another embodiment of a spinal implant to achieve rotational adjustment of the spine.

FIGS. 11-12 illustrate an alternative embodiment of a spinal implant 110 designed to be used in generally the same manner as implant 10, shown and described above. One difference between the implant 10 of FIGS. 1-5 and the implant 110 of FIGS. 11-12 is the location and form of the arrays of ridges 160, 162. In general, the arrays 160, 162 are further away from the post element 130 and aperture 133, and are semi-circular is shape. More particularly, the arrays of ridges 160, 162 are located at proximal edges 124, 128 of the medial surfaces 112, 116, respectively. Accordingly, the arrays of ridges 160, 162 form portions of the proximal edges 124, 128 of the first and second intradiscal elements 111, 115, respectively. As illustrated in FIGS. 11 and 12, one possible advantage of this embodiment is that larger fusion apertures 119 may be provided than in the implant 10 shown in FIGS. 1-5 because the arrays of ridges 160, 162 are not disposed on center portions of the medial surfaces 112, 116, respectively. In some examples, such large fusion apertures 119 may be advantageous for boney fusion in the lumbar region of the spine. The arrays of ridges 160, 162 are present in sufficient number and size to engage one another in several rotational positions (e.g., five-degree increments). In the example embodiment of FIGS. 11 and 12, arrays of ridges 160, 162 are provided as semi-circular segments. Thus, the arrays of ridges 160, 162 of the implant 110 can only interdigitate over a limited range of rotation, for example, 0°-20° (where 0° is defined as the orientation where flange portions 136, 137 are vertically aligned, as illustrated in FIG. 11).

In some embodiments, individual ridges 161, 163 within the arrays of ridges 160, 162 may be biased (in ratcheting fashion) towards one rotational direction, as illustrated in FIGS. 11 and 12. In such cases, the user may rotate the first intradiscal element 111 in one direction (e.g., counterclockwise in the example of FIGS. 11 and 12) relative to the second intradiscal element 115 using substantially less rotational force (i.e., torque) than required to rotate the first intradiscal element 111 in the other direction (e.g., clockwise in the example of FIGS. 11 and 12) relative to the second intradiscal element 115. Furthermore, with a sufficient bias of the ridges 161, 163, the torque required to rotate the first intradiscal element 111 relative to the second intradiscal element 115 in the non-preferred direction may be so great that rotation in one direction (i.e., clockwise in the example of FIGS. 11 and 12) is effectively impossible under physiological spinal loads, thus preventing the intradiscal elements 111, 115 from migrating back to their abnormal alignment in the axial plane once the implant 110 has been inserted, secured to the vertebrae using flange portions 136, 137, and rotated into the desired position by the user. In some examples, one or both of rods and cables (as described above with respect to the implant 10) may also contribute to this rotational stability.

Figure 14:
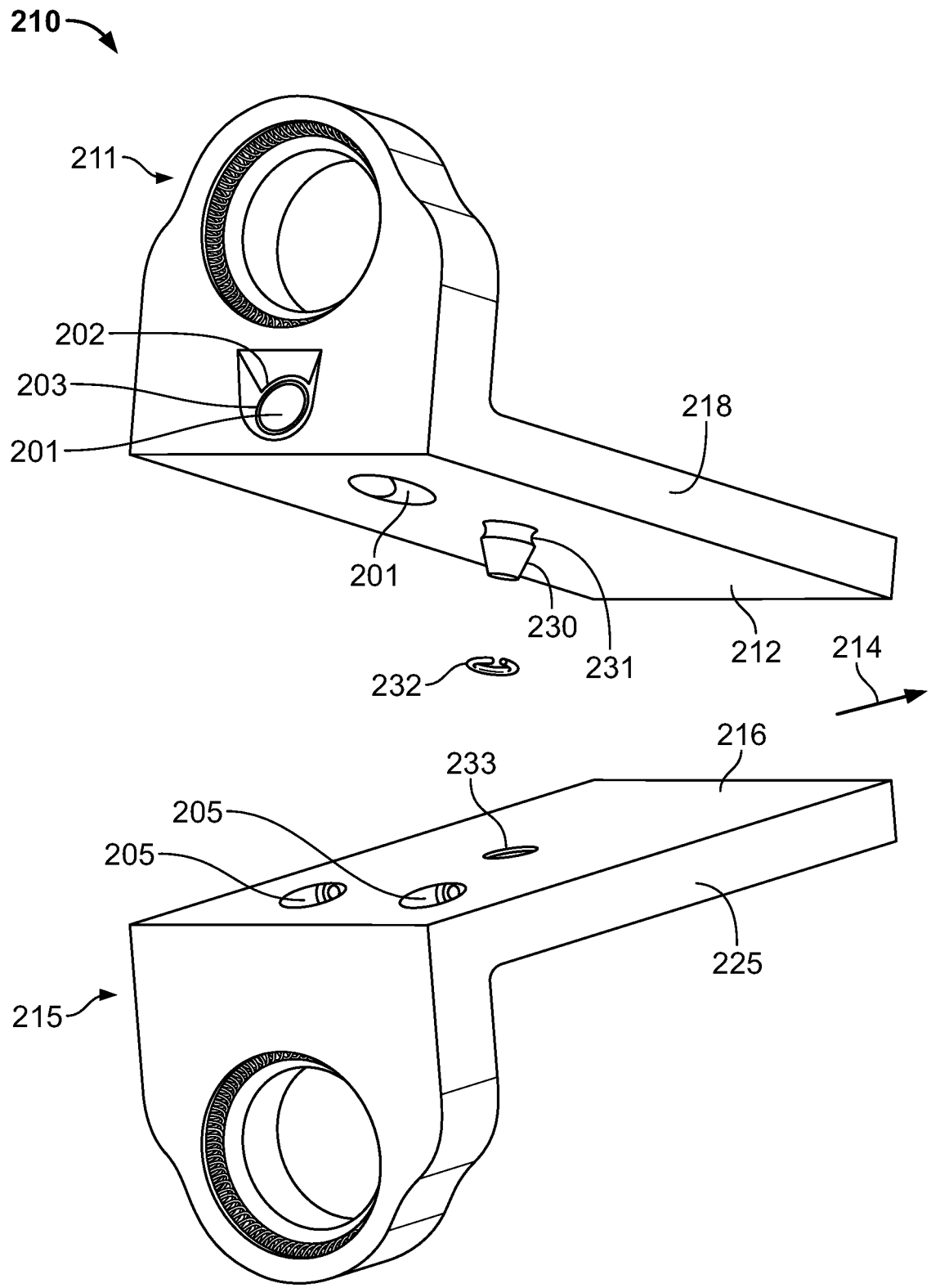

FIGS. 13-16 illustrate another embodiment of a spinal implant 210 in which retention of a rotated position is provided by a mechanism other than cooperating arrays of ridges. In FIGS. 13-16, some features of the implant are omitted for clarity of the different features included in this embodiment. Generally, the implant 210 includes a first (upper) intradiscal element 211 and a second (lower) intradiscal element 215, with the two elements 211, 215 being designed to be rotatably coupled to one another and being designed to be positioned within a disc space as a unit in a generally vertically stacked configuration. In order to set a particular desired rotational position between the two intradiscal elements 211, 215, the implant 210 includes a bore 201 that extends from a proximal surface 224 of the first intradiscal element 211 to a medial surface 212 of the first intradiscal element 211. The bore 201 extends at an angle between 20° and 70° relative to the longitudinal-axis 214 of the implant 210 (at an angle of 45° in the example of FIGS. 13-16). The bore 201 includes a recess 202 located at a proximal end of the bore 201. In some embodiments that will be described below, the first intradiscal element 211 may alternatively include more than one bore 201. In some embodiments also described below, the bore 201 may be replaced by an elongate slot that, like the bore 201, extends from the proximal surface 224 of the first intradiscal element 211 to the medial surface 212 of first intradiscal element 211. Referring particularly to FIG. 14, the recess 202 extends from the proximal surface 224 of the first intradiscal element 211 toward a point short of a distal surface 222 of the first intradiscal element 222. The recess 202 is sized and oriented such that a surface adjacently surrounding the proximal end of the bore 201 forms a plane that is perpendicular to an axis of bore 201. This provides a flat seat for a head of a bolt, a shank of which is sized to fit within the bore 201. In some embodiments, this seat area of the recess 202 may be provided with a locking mechanism, such as a canted-coil 203. The canted-coil 203 may lock the screw in place and/or may signal to the user that the screw has been fully seated. The canted-coil locking mechanism 203 is similar to the canted coil locking mechanism 70 that is described above with respect to the implant 10.

The implant 210 further includes two threaded bores 205 extending from a medial surface 216 of the second intradiscal element 215 to a point short of the opposite surface 217 of the second intradiscal element 215. In some embodiments, one or more of the threaded bores 205 may extend completely from the surface 216 to the surface 217 of the second intradiscal element 215. Threaded bores 205 are sized and oriented such that a bolt may pass through the bore 201 and be screwed into a threaded region of a single bore 205. The two threaded bores 205 allow the user to select one of two possible rotations for the first intradiscal element 211 relative to the second intradiscal element 215. Alternatively, in some embodiments, the second intradiscal element 214 may include a different number of threaded bores 205. At a point where the bore 201 intersects a longitudinal midline of the first intradiscal element 211 and the bores 205 are disposed on opposite sides of the longitudinal midline of the second intradiscal element 215 (as illustrated in FIG. 14), the implant 210 can be used to achieve vertebral de-rotation in either direction (i.e., clockwise or counterclockwise) after being implanted and secured (as illustrated with respect to the implant 10 in FIG. 9).

Figure 15:
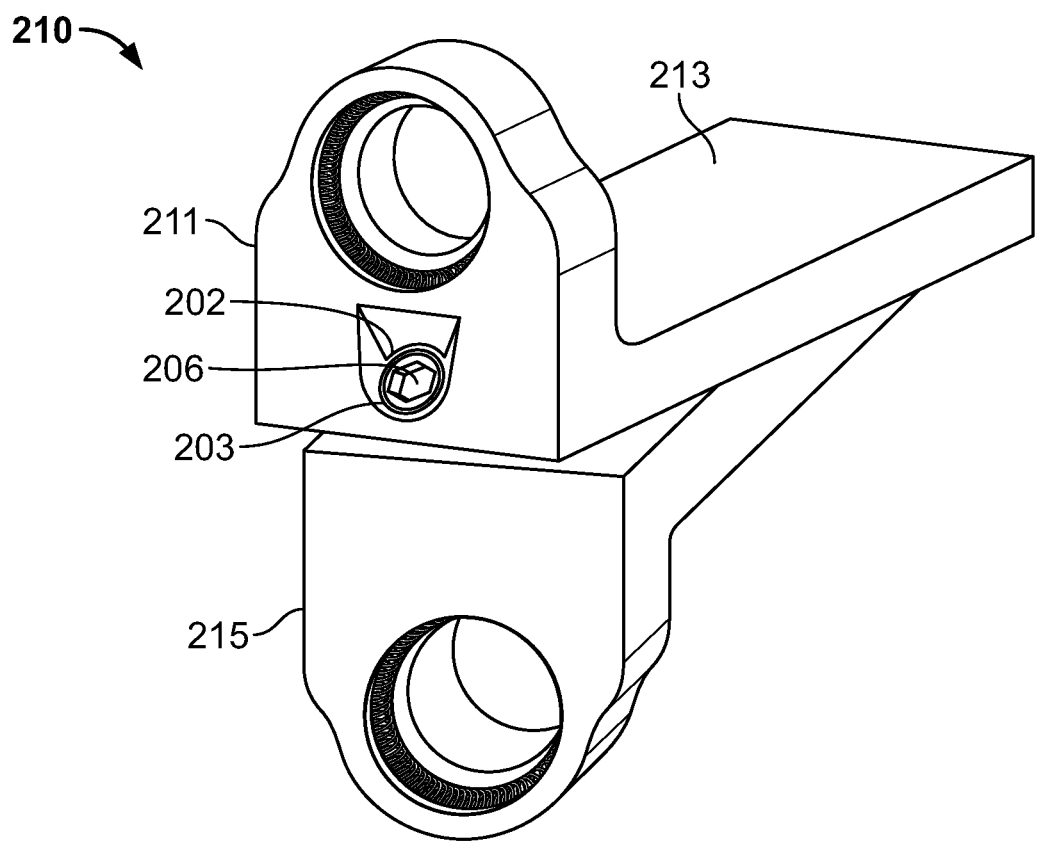
Figure 16:
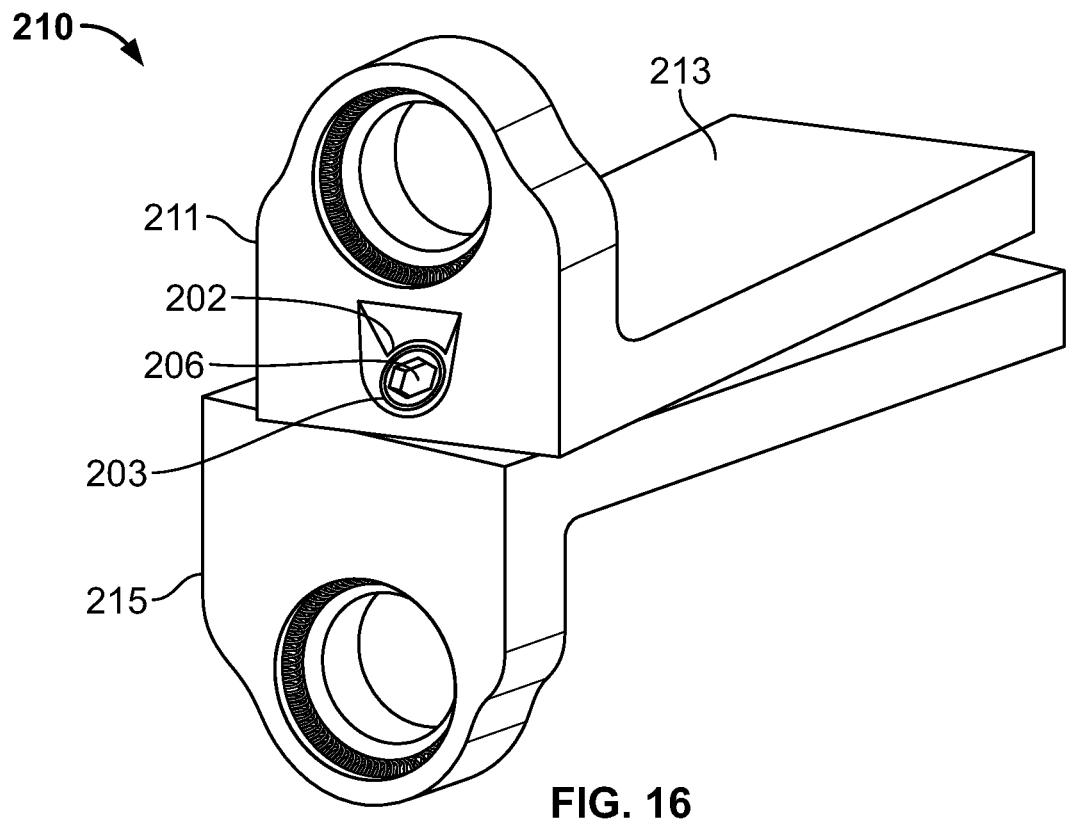

FIG. 15 illustrates the implant 210 following a clockwise rotation of the first intradiscal element 211 relative to the second intradiscal element 215. Conversely, FIG. 16 illustrates the implant 210 following a counterclockwise rotation of the first intradiscal element 211 relative to the second intradiscal element 215. Rotation can be locked using the bolt 206, which includes a hex-drive head and a threaded shank (not shown), where the threaded shank is sized to engage the threaded bore 205. Large scale de-rotations (i.e., rotations of 10° or more) can be achieved using the implant 210 by, for example, inserting and securing the implant 210 within the intervertebral space in the configuration illustrated in FIG. 15 with the screw 206 engaged within the first threaded bore 205, attaching flange portions 236, 237 to adjacent vertebrae with bone screws, and then removing the screw 206 from the first threaded bore 205. The first intradiscal element 211 and the attached upper vertebra are then rotated relative to the second intradiscal element 215 and the attached second vertebra such that the threaded bore 205 is aligned with the second bore 205. The bolt 206 is then reinserted through the bore 201, further engaging the screw 206 with the second threaded bore 205.

FIGS. 17-21 illustrate another embodiment of a spinal fusion implant 310 that does not include proximal flanges as included in previously described embodiments, and thus provides a lower profile design. The spinal fusion implant 310 includes a first (upper) intradiscal element 311 and a second (lower) intradiscal element 315, with the two elements 311, 315 being generally rectangular shaped, designed to be rotatably coupled to one another, and designed to be positioned within a disc space as a unit and in a generally vertically stacked configuration. The first intradiscal element 311 includes a leading or distal end 324, which is the end of intradiscal element 311 that is intended to be inserted into a disc space first. The first intradiscal element 311 further includes a first (upper) surface 313 for engaging a first (upper) vertebra, a second (medial) surface 312 (see FIG. 18) that faces opposite of the upper surface 313 and that is adapted to be rotatably coupled to the second intradiscal element 315, an anterior side 318, a posterior side 320 that faces opposite the anterior side 318, and a proximal end 322 (the anterior and posterior sides being named assuming a lateral approach to the spine from the right side of the patient).

Similarly, the second intradiscal element 315 includes a leading or distal end 328, which is the end of the intradiscal element 315 that is intended to be inserted into a disc space first. The second intradiscal element 315 further includes a first (lower) surface 317 for engaging a second (lower) vertebra, a second (medial) surface 316 (see FIG. 18) that faces opposite the lower surface 317 and that is adapted to be rotatably coupled to the first intradiscal element 311, an anterior side 325, a posterior side 326 that faces opposite the anterior side 325, and a proximal end 327 (the anterior and posterior sides being named assuming a lateral approach to the spine from the left side of the patient).

Figure 17:
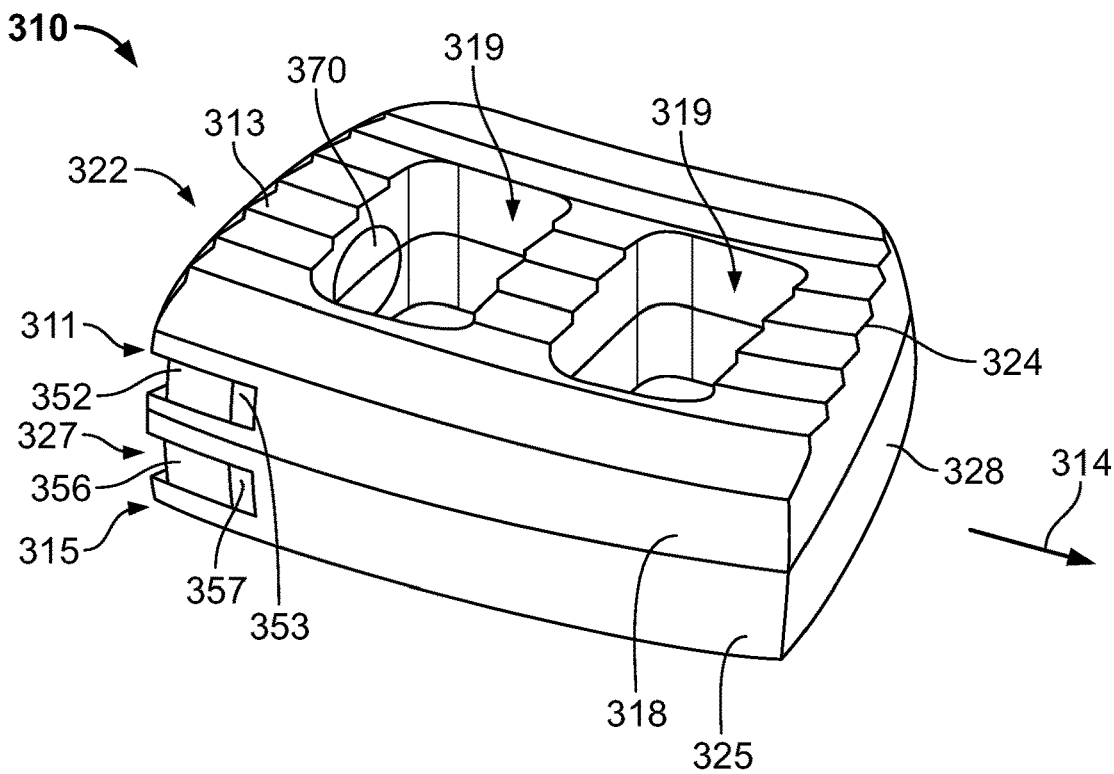
FIGS. 17-21 are various views that illustrate yet another embodiment of a spinal implant to achieve rotational adjustment of the spine.

A proximal portion of the anterior sides 318, 325 (left side portion of the sides 318, 325, as shown in FIG. 17) of the first and second intradiscal elements 311, 315 include engagement grooves 352, 356 opening in the proximal ends 322, 327 of the first and second intradiscal elements 311, 315 and extending distally to a point short of the distal ends 324, 328 of the first and second intradiscal element 311, 315, respectively. The posterior sides 320, 326 of the first and second intradiscal elements 311, 315 include engagement grooves 350, 354 (see FIG. 21) opening in the proximal ends 322, 327 of the first and second intradiscal elements 311, 315 and extending distally to a point short of the distal ends 324, 328 of the first and second intradiscal elements 311, 315, respectively. At distal-most portions of the engagement grooves 352, 356, the grooves 352, 356 extend into the anterior sides 318, 325, forming gripping indents 353, 357, respectively. At the distal-most portions of the engagement grooves 350, 354, the grooves 350, 354 extend into the posterior sides 320, 326, forming gripping indents (not shown). As will be discussed in detail below, the engagement grooves 350, 352, 354, 356 are configured to receive insertion and de-rotation instruments.

Referring particularly to FIG. 17, the first intradiscal element 311 includes two fusion apertures 319 that extend entirely through the first element 311, from its outer or upper surface 313 to its medial or lower surface 312, while the second intradiscal element 315 also includes two correspondingly positioned fusion apertures 319 that extend entirely through the second element 315, from its medial or upper surface 316 to its outer or lower surface 317. The generally D-shaped regions of the apertures 319 maximizes the size of the apertures 319 and thus facilitate bony through-growth; however, the apertures 319 may, in alternative embodiments, be provided in any number of suitable shapes, such as a circle, an oval, or a rectangle. In some embodiments, multiple apertures may be included and separated by one or more support walls.

In some examples, fusion of the first and second vertebrae may be improved by depositing various osteoinductive materials within the fusion apertures 319 and/or adjacent to the spinal fusion implant 310. Such osteoinductive materials may be introduced before, during, or after insertion of the spinal fusion implant 310. Example osteoinductive materials include autologous bone harvested from the patient receiving the spinal fusion implant 310, a bone allograft, a bone xenograft, non-bone implants (e.g., a ceramic, a metal, or a polymer), bone morphogenic protein, and bio-resorbable materials (e.g., poly (D,L-lactic-co-glycolic)-based polymers).

Figure 18:
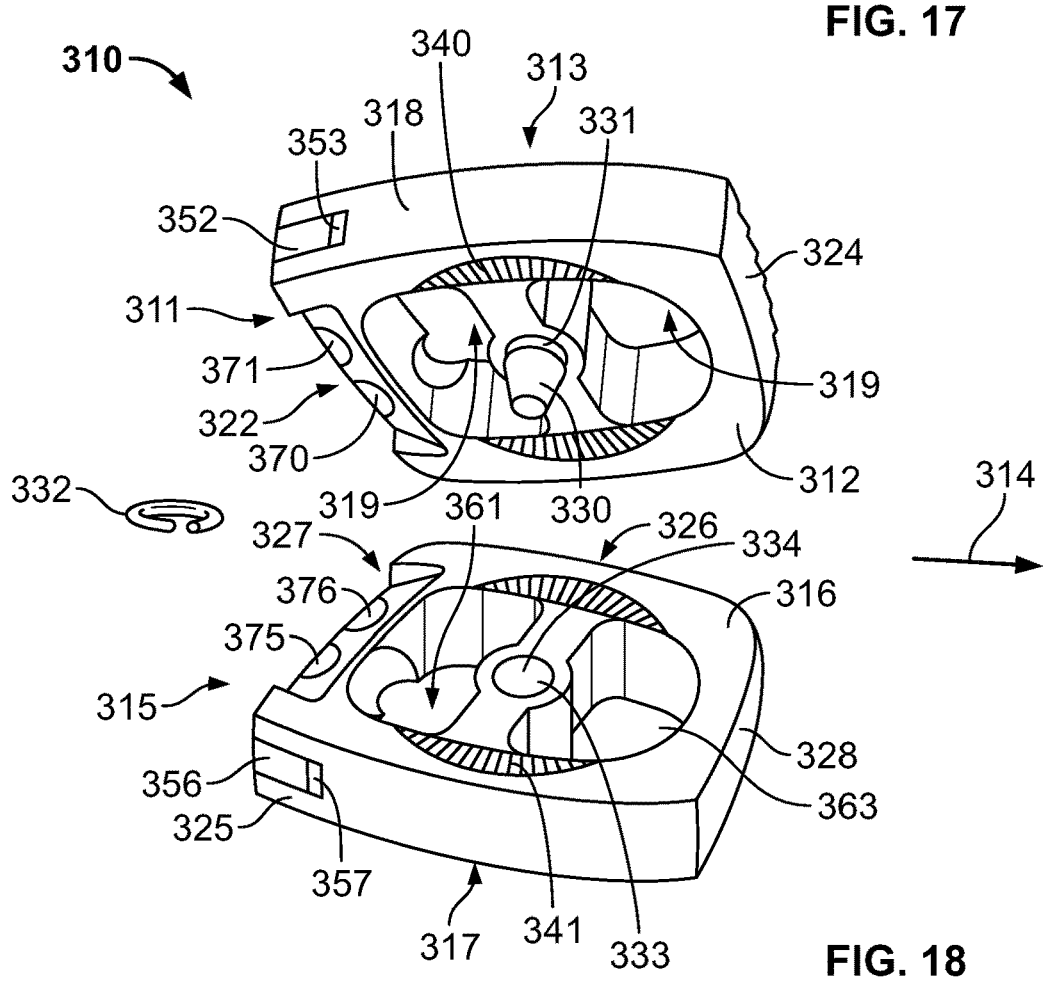

Referring to FIG. 18, central portions of the proximal ends 322, 317 are angled toward the distal ends 324, 328 of the first and second intradiscal elements 311, 315, respectively, such that the proximal surfaces 322, 327 abut their respective medial surfaces 312, 316 at oblong angles and abut their respective outer (upper and lower) surfaces 313, 317 at acute angles, respectively. In the example of FIGS. 17 and 18, the proximal ends 322, 327 form 135° angles with the two facing medial surfaces 312, 316, respectively, and form 45° angles with the upper and lower surfaces 313, 317, respectively. Accordingly, the proximal surfaces 322, 327 are oriented generally perpendicularly to one another when the implant 310 is assembled.

Figure 21:
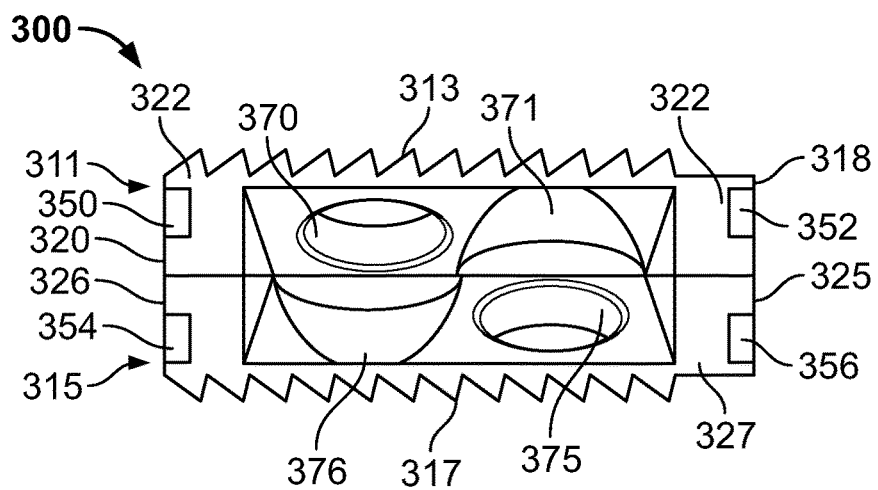

The angled proximal surfaces 322, 327 each includes a recess 371, 376, respectively, and a bore or screw hole 370, 375, respectively, each extending bore 370, 375 from their respective proximal surfaces 322, 327 to their respective upper or lower surfaces 313, 317, respectively. The first and second recesses 371, 376 extend from the angled proximal surfaces 322, 327 toward the distal surfaces 324, 328, respectively. Referring particularly to FIG. 21, the first recess 371 is positioned across from the second bore 375 and increases the accessible surface area circumscribing the second bore 375 on the proximal surface 322 when the implant 310 is assembled. Similarly, the second recess 376 is positioned across from first bore 370 and increases the accessible surface area circumscribing the first bore 370 on the proximal surface 327 when implant the 310 is assembled.

Figure 19:
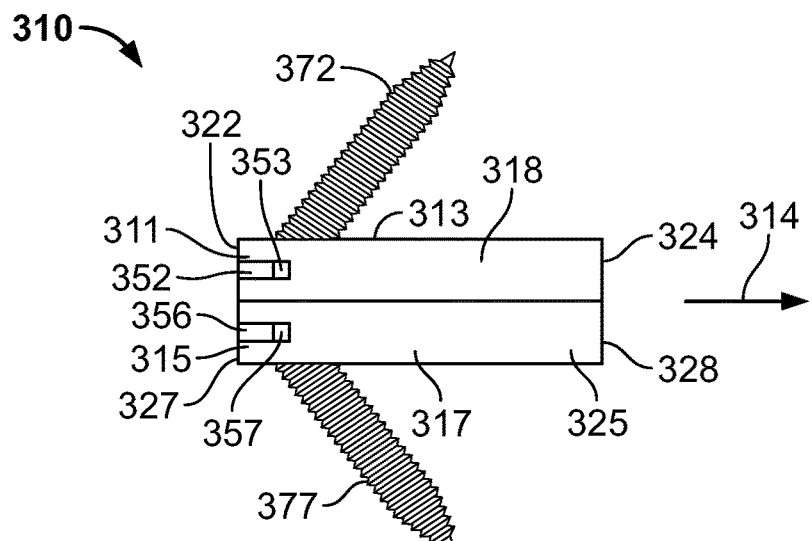
Figure 20:
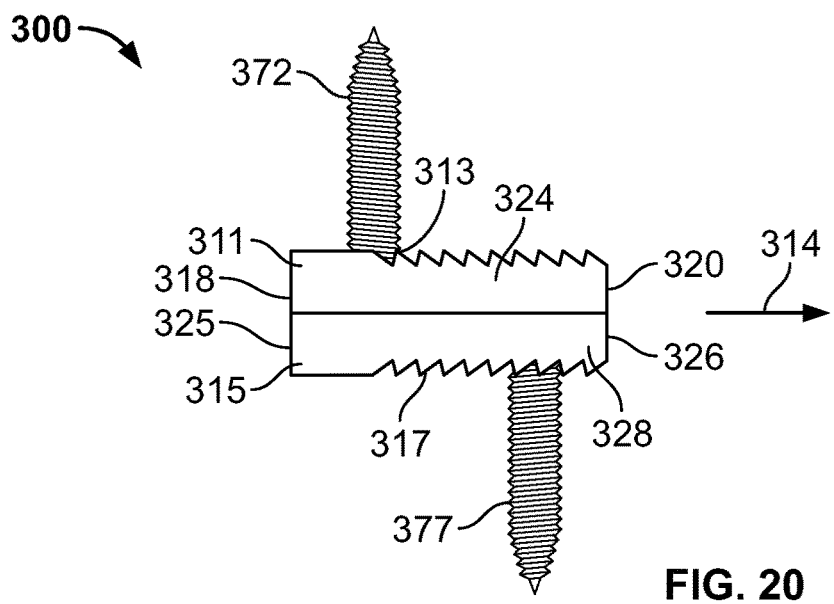

Referring to FIGS. 19 and 21, the first bore 370 extends from the angled proximal surface 322 at an upward angle such that when a first bone screw 372 is inserted into the first bore 370, the bone screw 372 extends from the implant 310 at an angle and can penetrate into the upper vertebral body adjacent the upper surface 313 of the first intradiscal element 311. In the example of FIG. 19, the penetration angle is approximately 45° (relative to a longitudinal axis 314 of the implant 310); however, in other embodiments, the penetration angle may range from 35 to 55°. The second bore 375 extends from the angled proximal surface 327, but is angled downwardly in the direction vertically opposite that of the first bore 370, such that when bone screw 377 is inserted into the second bore 375, the bone screw 377 extends from the implant 310 at an angle and can penetrate the lower vertebral body adjacent the bottom surface 317 of the second intradiscal element 315. In the example of FIG. 19, the penetration angle is approximately 45° (relative to the longitudinal axis 314 of the implant 310); however, in other embodiments, the penetration angle may range from 35° to 55°. As illustrated in FIG. 20, the bores 370, 375 may be inwardly angled such that distal ends of the bone screws 372, 377 converge towards the longitudinal axis 314 of the implant 310. Alternatively, in some embodiments, the bores 370, 375 may diverge away from the longitudinal axis 314 of the implant 310. In some examples, the bores 370, 375 may be oriented such that the bone screws 372, 377 are angled medially at 10°. In other embodiments, the bores 370, 375 may be oriented such that the bone screws 372, 377 are angled medially at other angles, for example between 5 and 15°.

Referring again to FIG. 18, the first intradiscal element 311 can be rotated relative to the second intradiscal element 315 via a post element 330, an aperture 333, and a snap ring 332. The post element 330 extends from an approximate center of the lower surface 312 of the first intradiscal element 311. The post element 330 includes bulbous portion at its distal end, and proximal of that bulbous portion includes a circumferential groove 331 sized to receive the snap-ring 332 in a biased configuration. The aperture 333 is formed in an approximate center of the medial or upper surface 316 of the second intradiscal element 315, and the snap-ring 332 is sized to fit within a circumferential groove 334 formed within the aperture 333. In the example of FIG. 18, the post element 330 and the first intradiscal element 311 are formed as a single component. However, in some embodiments, a post element and an intradiscal element may be provided as separate components, in which case the post element may be locked into a recess of the first intradiscal element. In such a case, a distal end of the post element may be formed as a threaded shank sized to fit within a threaded aperture in the first intradiscal element, and a hex-drive recess may be included within a proximal end of the post for securing the post within the threaded aperture (not shown).

The lower or medial surface 312 of the first intradiscal element 311 includes an array of ridges 340, wherein individual ridges extend radially with respect to the post element 330. Similarly, the upper or medial surface 316 of the second intradiscal element 315 includes a cooperatively positioned array of ridges 341, wherein individual ridges extend radially with respect to the aperture 333. In the example of FIG. 18, the ridges 340, 341 cover only a portion of the surfaces 312, 316. The individual ridges 340, 341 may be biased in one rotational direction (clockwise or counterclockwise) such that rotating the first intradiscal element 311 relative to the second intradiscal element 315 about the post 330 requires substantially more force in one rotational direction (e.g., clockwise) than that is required in the other rotational direction (e.g., counterclockwise), or such that rotation is only possible in one direction. The ridges 340, 341 are evenly spaced about the post 330 and sized such that when the surfaces 312, 316 are brought into contact with one another and the post element 330 is disposed within the aperture 333, the upper ridges 340 will substantially interdigitate the lower ridges 341. This "stacked poker chip" arrangement allows the first intradiscal element 311 to be rotated incrementally relative to the second intradiscal element 315.

In some examples, an insertion instrument (not shown) may be provided to insert the implant 310 into a disc space between adjacent first and second vertebrae. In one example, the insertion instrument includes an elongate shaft, a proximal end, and a distal end. The distal end includes a pair of lateral gripping arms. The gripping arms are sized to fit within the implant's engagement grooves 350, 352 and the gripping indents 353 (one of the indents next to groove 350 not being shown) of the first and second intradiscal elements 311, 315. The proximal ends of the insertion instrument may include a means for adjusting the distance between the gripping arms, which can be adjusted to fit snugly within the engagement grooves 350, 352 and the gripping indents 353 to insert the implant 310. Once the gripping arms of the insertion instrument are adjusted, the insertion instrument may be inserted into the engagement grooves 350, 352. The implant 310 may then be inserted between the first and second vertebrae using the insertion instrument. The gripping arms may then be removed from the implant 310, thereby releasing the insertion instrument from the implant 310 to allow for fixation of the implant 310 to the first and second vertebrae.

In order to rotate the first intradiscal element 311 relative to the second intradiscal element 315, two separate insertion instruments may be used. The second insertion instrument may be substantially similar in construction to the previously described insertion instrument and accordingly may include a pair of lateral gripping arms that are sized to fit within the engagement lower element's grooves 354, 356 and the gripping indents 357 (again, the indent next to groove 354 not being shown in the figures). Once the gripping arms of the first and second insertion instruments are adjusted, the first and second insertion instruments may be inserted into the engagement grooves 350, 352 and 354, 356, respectively. By adjusting the lateral distance between proximal ends of the first and second insertion instruments, the user can rotate the first intradiscal element 311 relative to the second intradiscal element 315. The gripping arms of the first and second insertion instruments can then be removed from the implant 310, thereby releasing the insertion instruments from the implant 310.

Figure 22:
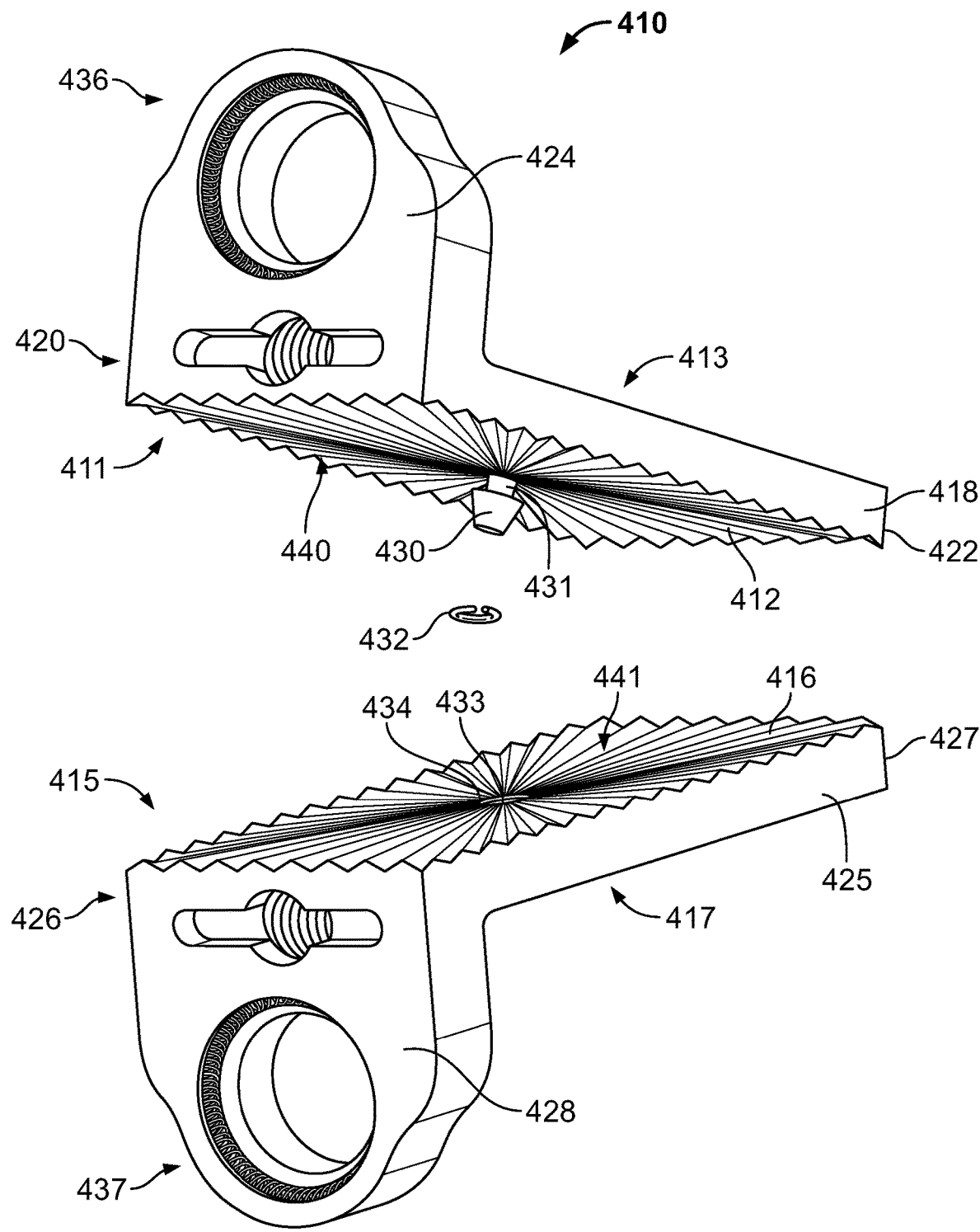
FIG. 22 illustrates yet another embodiment of a spinal implant to achieve rotational adjustment of the spine.

FIG. 22 illustrates an alternative embodiment of a spinal implant 410, wherein ridges are disposed across the entire mating (medial) surfaces of the intradiscal elements. Here again, the implant 410 includes a first (upper) intradiscal element 411 and a second (lower) intradiscal element 415, with the two elements 411, 415 being designed to be rotatably coupled to one another and being designed to be positioned within a disc space as a unit in a generally vertically stacked configuration. The bottom or medial surface 412 of the upper intradiscal element 411 includes several ridges 440 extending radially from the post element 431 to edges of the medial surface 412. Similarly, the upper or medial surface 16 of the lower intradiscal element 415 includes several similarly designed ridges 441 extending radially from the aperture 433 to edges of the medial surface 416. The cooperating ridges 440, 441 are present in sufficient number and size such that they provide several rotational positions (i.e., 72 evenly-spaced ridges provide five-degree rotational increments). The ridges 440, 441 may be biased in one rotational direction such that rotating the first intradiscal element 411 in one rotational direction (e.g., counterclockwise) relative to the second intradiscal element 415 requires substantially more rotational force (torque) than does rotating the first intradiscal element 411 in the other direction (e.g., clockwise) relative to the second intradiscal element 415.

Figure 23:
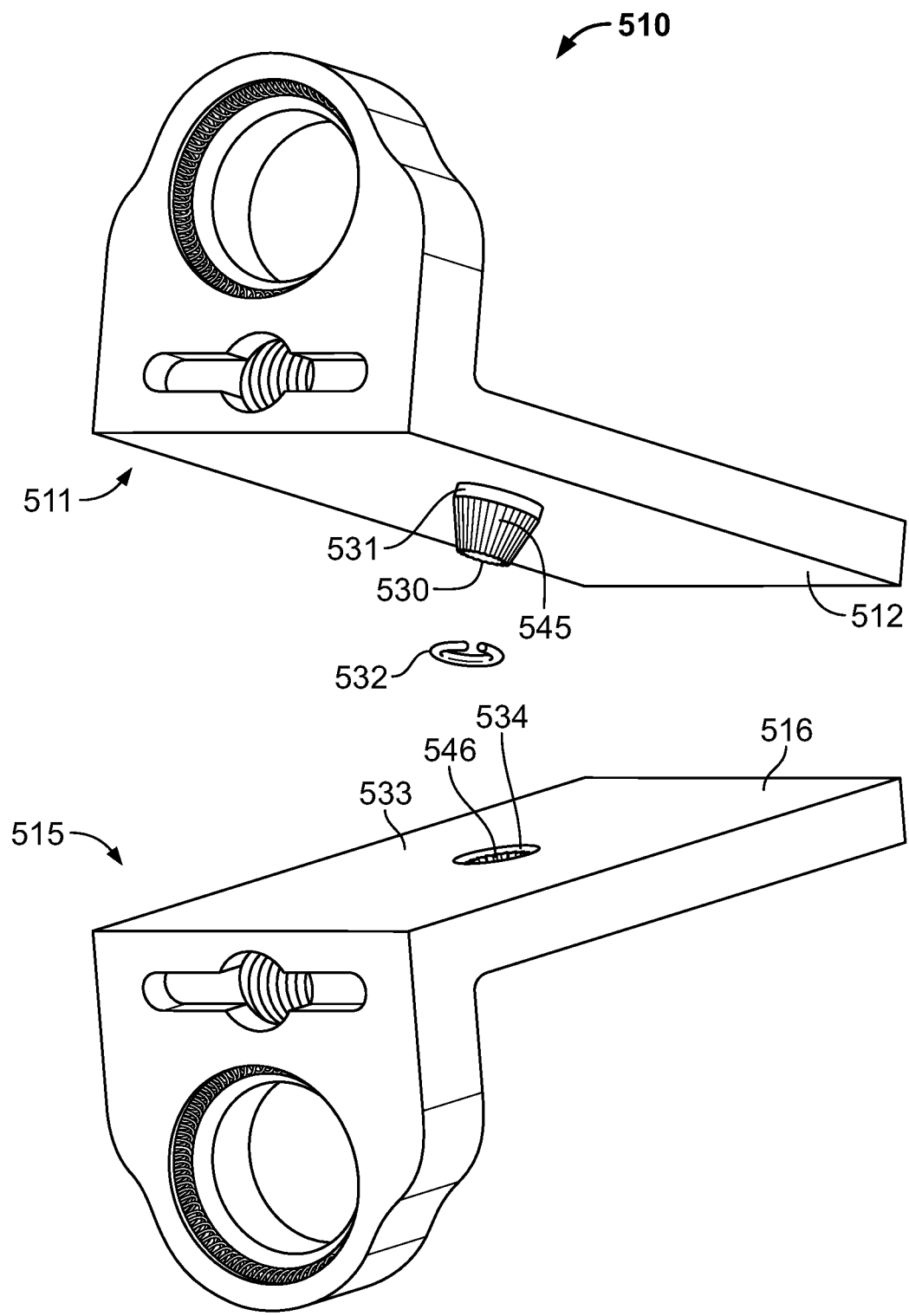
FIG. 23 illustrates yet another embodiment of a spinal implant to achieve rotational adjustment of the spine.

FIG. 23 illustrates another embodiment of a spinal implant 510, wherein instead of being disposed on the medial surfaces of the intradiscal elements, the rotational incrementing and retention elements (ridges) are disposed on the post element and in the cooperating recess into which the post element is engaged. Again in this embodiment, the spinal implant 510 includes a first (upper) intradiscal element 511 and a second (lower) intradiscal element 515, with the two elements 511, 515 being designed to be rotatably coupled to one another and being designed to be positioned within a disc space as a unit in a generally vertically stacked configuration. The first intradiscal element 511 includes a post element 530 upon which several longitudinal ridges 545 are disposed, and the second intradiscal element 515 includes an aperture 533 having a surface from which several longitudinal ridges 546 extend. The ridges 545, 546 are present in sufficient number such that the first and second intradiscal elements 511, 515 can be oriented in several relative rotational positions (e.g., five-degree increments) about a longitudinal axis of the post element 530. In some embodiments, the ridges 545, 546 may be biased in one rotational direction (i.e., counterclockwise or clockwise). In various embodiments, the post element 530 and the aperture 533 may be of different sizes. For example, a larger post element 530 and aperture 533 may be desired to provide for greater stability and/or to provide for more ridges on the post element 530 and/or aperture 533 for greater granularity in the degree of individual increments in the incremental rotation.

Figure 24:
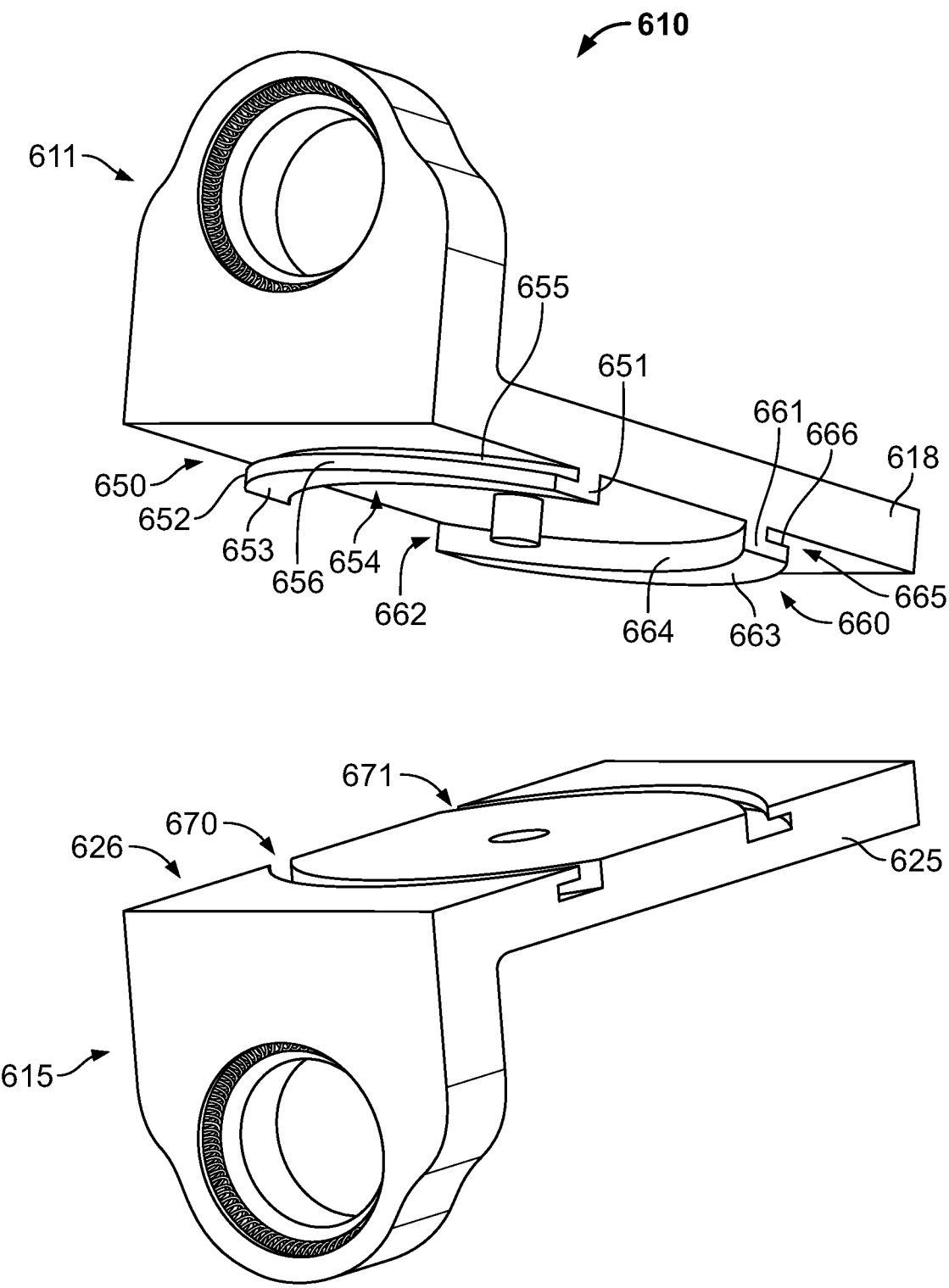
FIG. 24 illustrates yet another embodiment of a spinal implant to achieve rotational adjustment of the spine.

FIG. 24 illustrates another embodiment of a spinal implant 610, wherein one or more projections or rails extending from a first intradiscal element slidably engage within channels included within the second intradiscal element. Here again, the implant 610 includes a first (upper) intradiscal element 611 and a second (lower) intradiscal element 615, with the two elements 611, 615 being designed to be rotatably coupled to one another and being designed to be positioned within a disc space as a unit in a generally vertically stacked configuration. Two semi-circular projections or rails 650, 660 extend from a lower or medial surface 612 of the first intradiscal element 611 and slidably engage within corresponding semi-circular channels 670, 671 included within the upper or medial surface 616 of the second intradiscal element 615. The two rails 650, 660 include respective lower surfaces 653, 663, anterior ends 651, 661, posterior ends 652, 662, medial surfaces 654, 664 that face the post element, and distal surfaces 655, 665 that face opposite the medial surfaces 654, 664. In the example of FIG. 24, the two rails 650, 651 and two corresponding channels 670, 671 extend entirely between the anterior surfaces 618, 625 and the posterior surfaces 620, 627 of the first and second intradiscal elements 611, 615, respectively. However, in some embodiments, the two rails 650, 651 and two corresponding channels 670, 671 may only extend partially between the anterior surfaces 618, 625 and the posterior surfaces 620, 627 of the first and second intradiscal elements 611, 615, respectively. The channels 670, 671 and the projections 650, 660 are semi-circular or arcuate with respect to the surfaces 612, 616 such that the projections 650, 660 slidably engage within the channels 670, 671 as the first intradiscal element 611 rotates with respect to the second intradiscal element 615 about the post element 630.

As designed, the upper and lower intradiscal elements 611, 615 of the FIG. 24 implant 610 are designed to be assembled, and once assembled, the cooperating rails 650, 660 and corresponding channel structures 670, 671 prevent the elements 611, 615 from separating from one another within a particular range of relative rotational movement. Assembly of the intradiscal elements 611, 615 will be described later in connection with FIGS. 31A-F.

Figure 25:
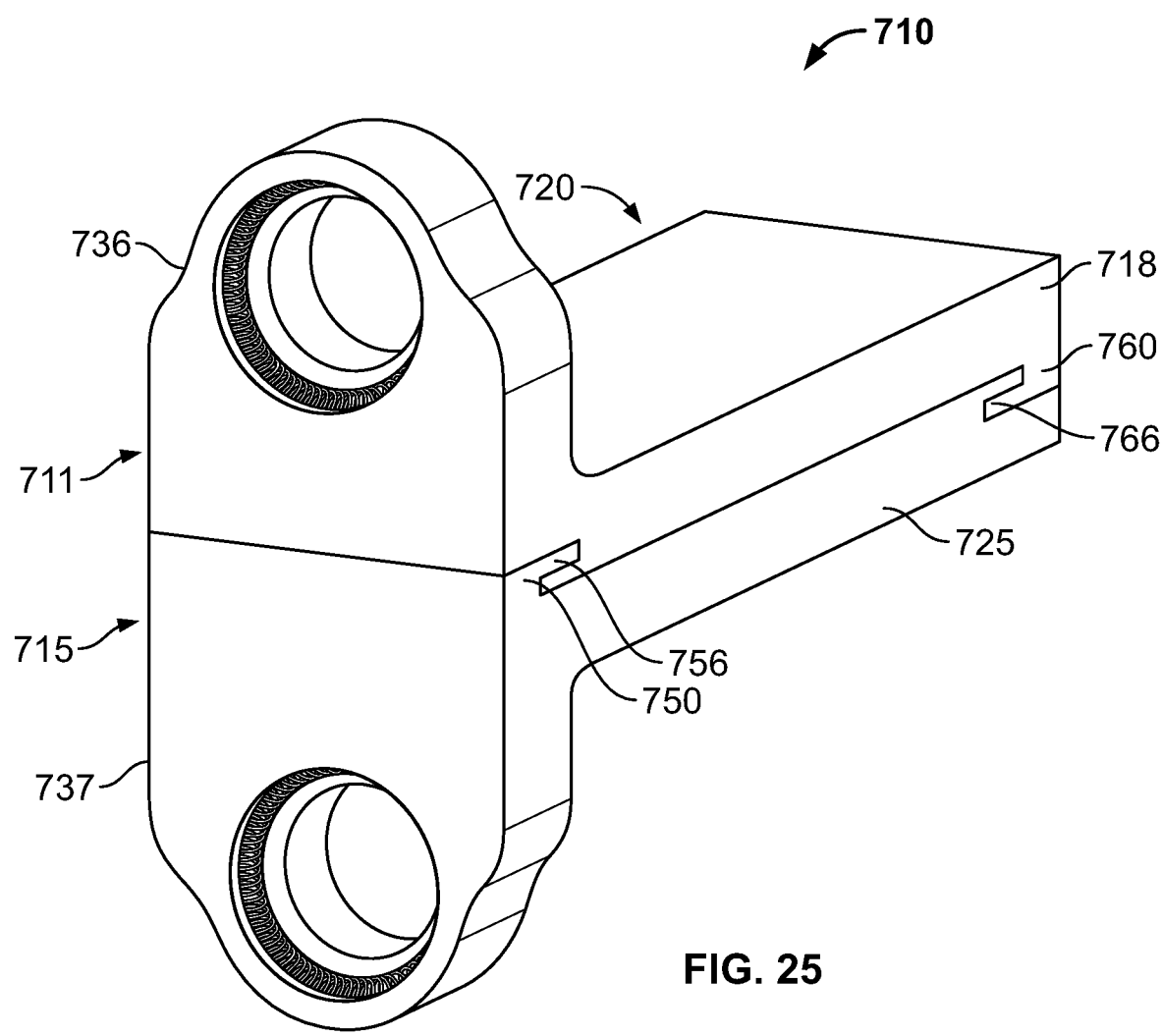
FIGS. 25-26 are various views that illustrate yet another embodiment of a spinal implant to achieve rotational adjustment of the spine.
Figure 26:
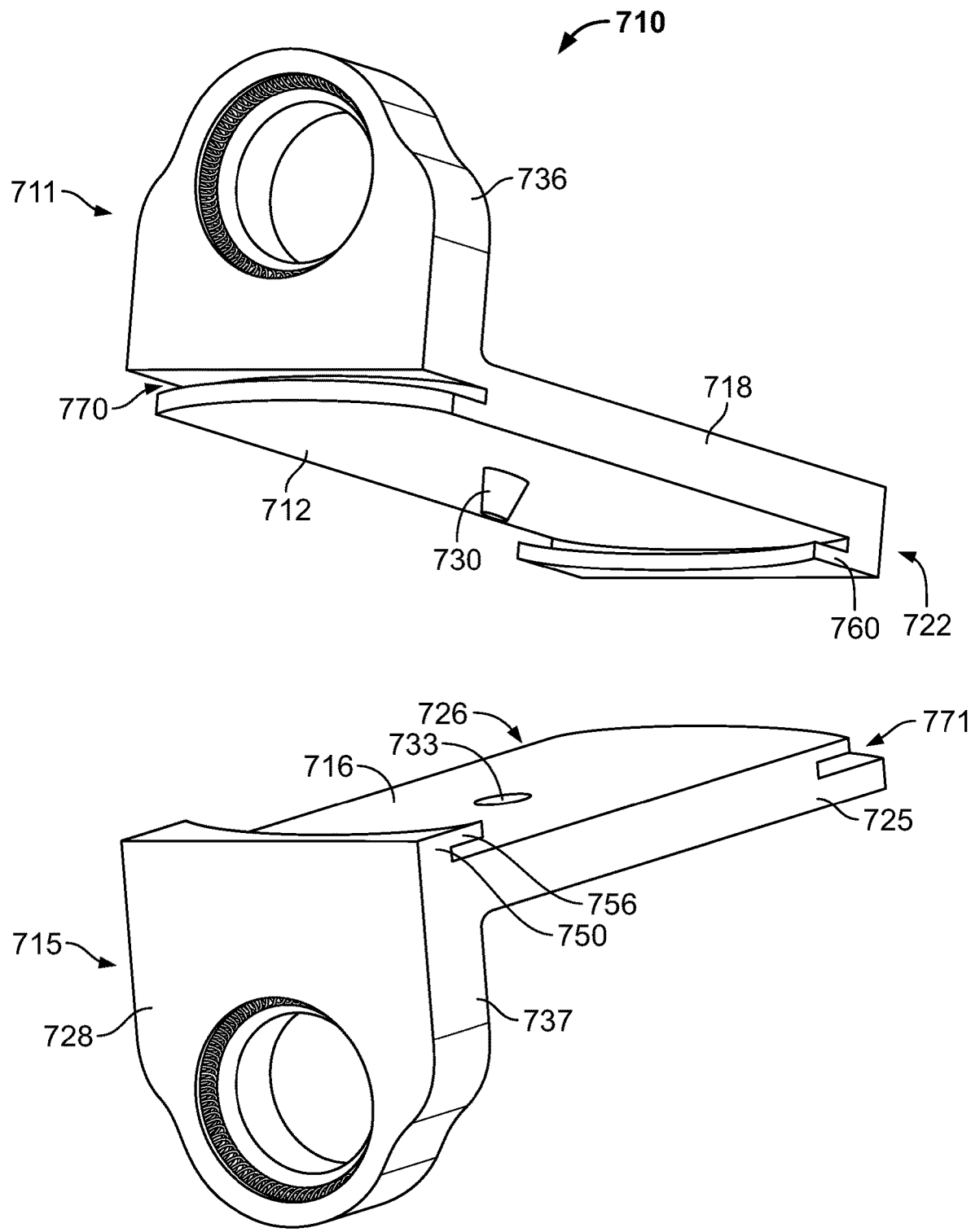

FIGS. 25-26 illustrate an embodiment of a spinal implant 710 similar to the implant 610 shown in FIG. 24, except that the implant 710 of FIGS. 24-25 has an alternative design of the engagement structure that prevents the two intradiscal elements from separating after assembly within a range of relative rotational positions. In FIGS. 25-26, some features of the implant are omitted for clarity of the different features included in this embodiment. In particular with respect to the engagement structure, as shown in FIGS. 25 and 26, a first projection or rail 750 extends from a proximal end 728 of the lower intradiscal element 715, and along the entire width of the lower intradiscal element 715. The first rail 750 includes a perpendicularly projecting ridge 756 that extends distally from a medial (inner) surface of the first rail 750, thus forming a slot between the ridge 756 and the medial surface 716 of the lower element 715. A similarly designed second projection or rail 760 extends from a distal end 722 of the upper intradiscal element 711, and along the entire width of the upper intradiscal element 715. The second rail 760 similarly includes a ridge 766 that extends proximally from a medial surface of the second rail 760, thus forming a slot between the ridge 766 and the medial surface 712 of the upper intradiscal element 711.

Corresponding to the first and second rails 750, 760 and ridges 756, 766 are channels 770, 771 included within the first and second intradiscal elements 711, 715, respectively. The channels 770, 771 are semi-circular or arcuate within a plane of the medial surfaces 712, 716 of the first and second intradiscal elements 711, 715, respectively, and are sized to slidably accept the complementary shaped rails 750, 760 and form I-shaped' recesses in anterior and posterior surfaces 718, 720, and 725, 726 where each projection 750, 760 includes a single ridge 756, 766, respectively, to form an 'L-shape.' In some embodiments, however, the projections 750, 760 may alternatively include ridges that extend horizontally beyond medial surfaces 754,7 64 such that the ridges extend toward a center of the first intradiscal element 11, with respective channels being dimensioned to accept such projections. When the implant 710 is assembled, post element 730 is disposed within aperture 733, and surfaces 712, 716 are locked in substantial conformity at desired rotational positions.

Figure 27:
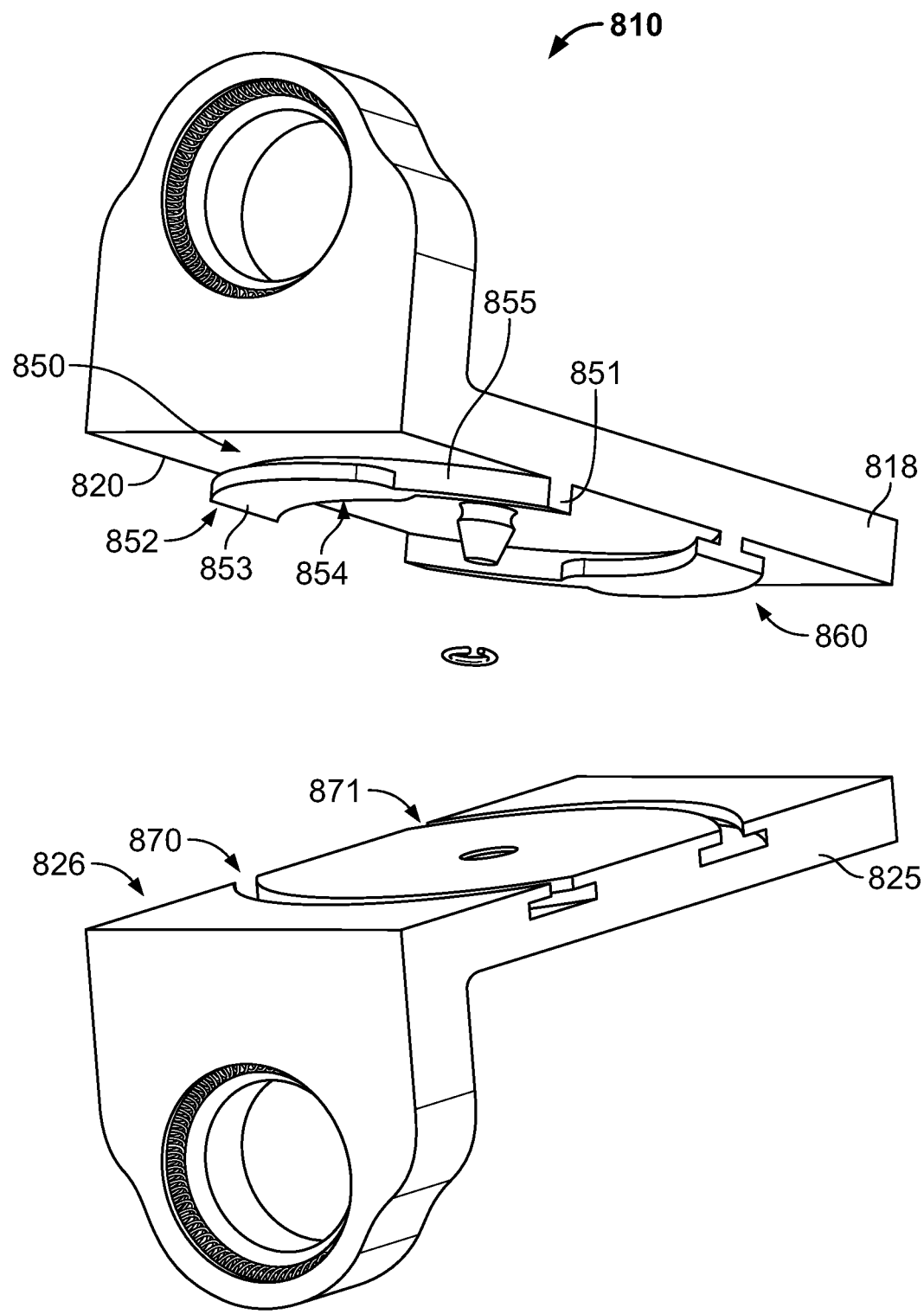
FIGS. 27-28 illustrate yet another embodiment of a spinal implant to achieve rotational adjustment of the spine.
Figure 28:
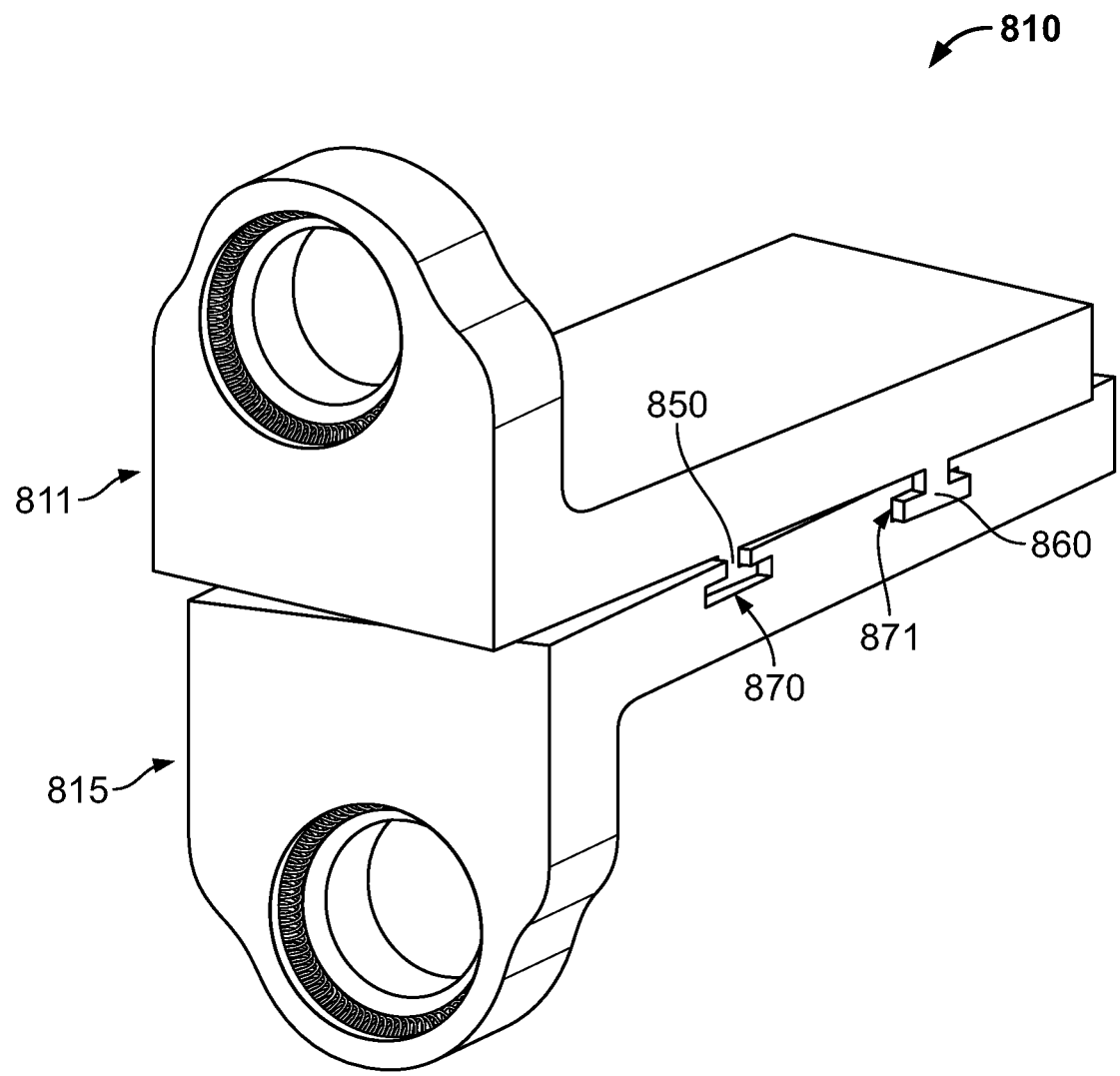

FIGS. 27-28 illustrates an alternative embodiment of a spinal implant 810 similar to the FIG. 24 embodiment, except that instead of having only one ridge on the semi-circular rails, there are two ridges, with one on each side. In FIGS. 27-28, some features of the implant are omitted for clarity of the different features included in this embodiment. In particular with respect to the design shown in FIGS. 27-28, two semi-circular T-shaped projections or rails 850, 860 extend from a medial surface of the first intradiscal element 811. Each of the rails 850, 860 includes a stem portion and a pair of oppositely extending ridges from an end portion of the stem, thus forming the "T-shaped" projection. The first ridge extends proximally from a proximal surface of the stem, and a second ridge extends distally from a distal surface of the stem. Corresponding to the two T-shaped rails 850, 860 are two T-shaped channels 870, 871 included within a medial surface 816 of the second intradiscal element 815. The channels 870, 871 are sized to slidably accept the T-shaped rails 850, 860, thereby forming upside-down 'T-shaped' recesses in surfaces that extend from an anterior surface 825 to a posterior surface 826 of the second intradiscal element 815.

Generally, linkable projections such as those shown in FIG. 24-28 may, instead of initially projecting perpendicularly (at least initially) from the intradiscal elements medial surface, may alternatively extend at a non-right angle from the medial surface of an intradiscal element. An example of such an alternative is shown in FIGS. 29-30.

Figure 29:
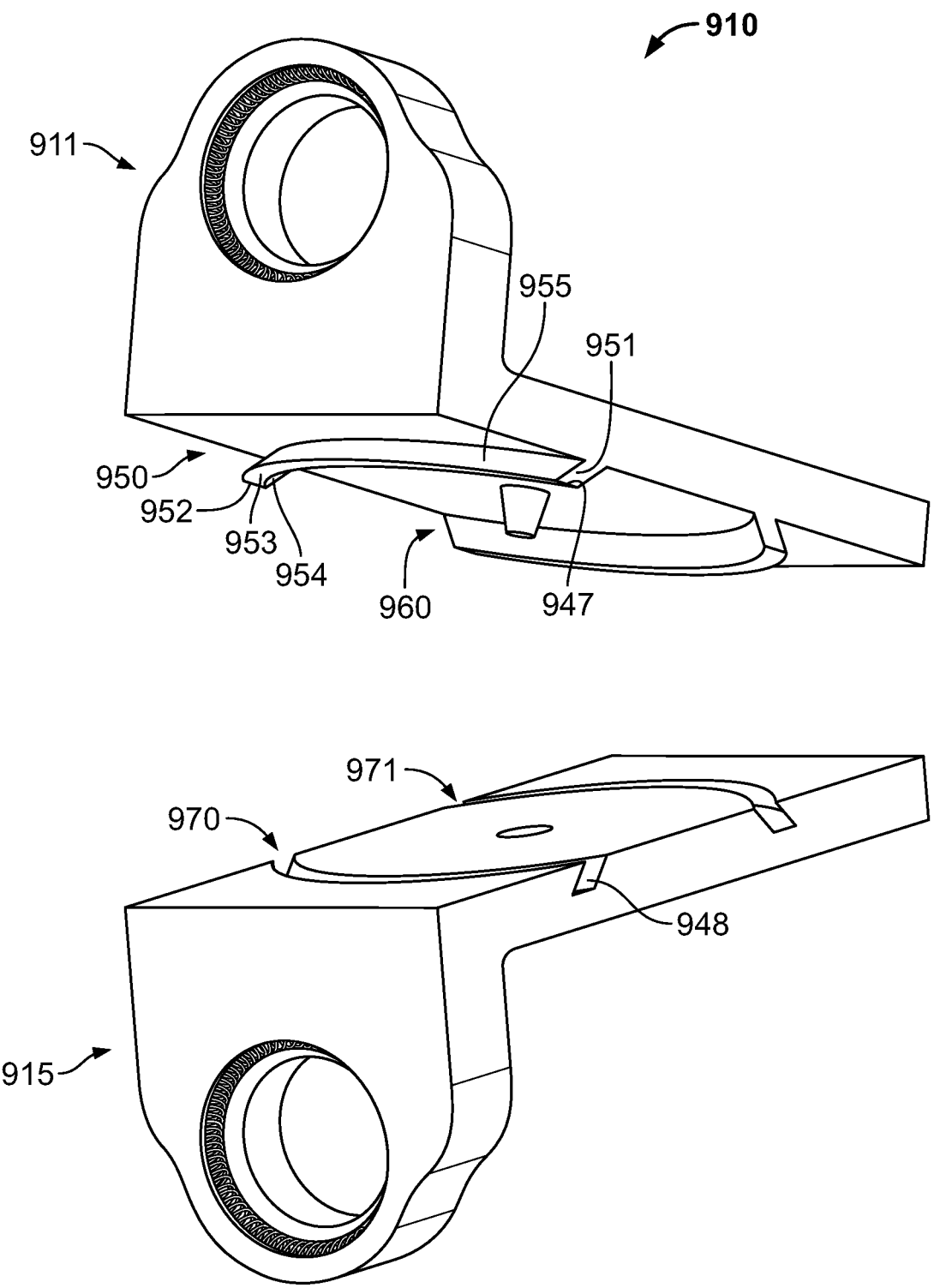
FIGS. 29-30 are various views that illustrate yet another embodiment of a spinal implant to achieve rotational adjustment of the spine.
Figure 30:
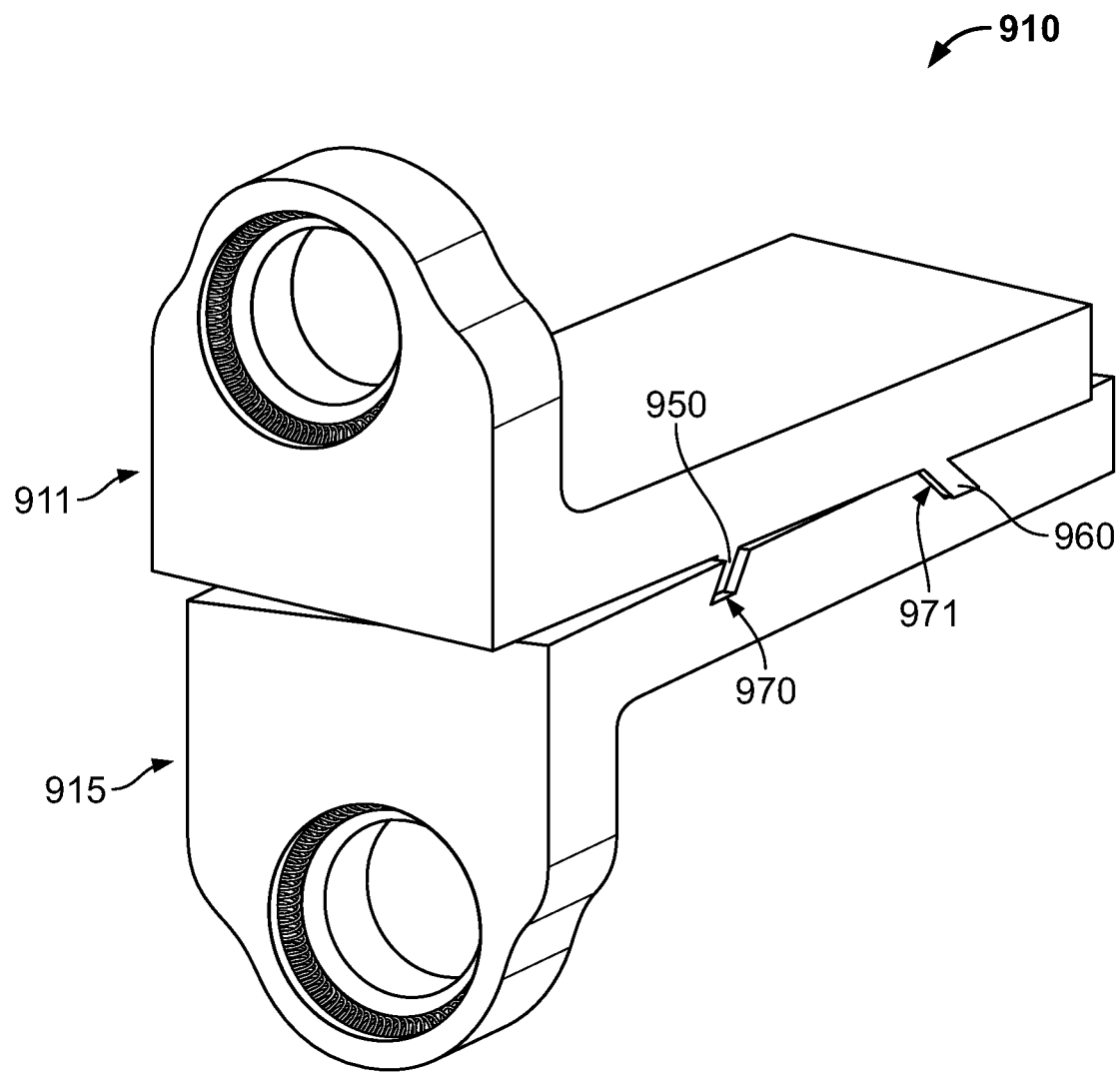

FIGS. 29-30 illustrate another embodiment of a spinal implant 910, wherein semi-circular rails extend from a medial surface of a first intradiscal element a non-right angle and, along with a corresponding groove in a medial surface in a second intradiscal element, provide engagement between the two intradiscal elements over a range of rotational movement. Generally, the implant 910 includes a first (upper) intradiscal element 911 and a second (lower) intradiscal element 915, with the two elements 911, 915 being designed to be rotatably coupled to one another and being designed to be positioned within a disc space as a unit in a generally vertically stacked configuration. Two semi-circular projections or rails 950, 960 extend from a lower surface 912 of an upper intradiscal element 911 at an angle of approximately 45° relative to a longitudinal axis of the post element 930, oriented in this embodiment away from the post element 930. In other embodiments, the angled rails 950, 960 may extend from the medial surface 912 at an angle other than 45°, for example in a range of 20 to 70°. In the example of FIGS. 29-30, corresponding channels 970, 971 in the lower intradiscal element 915 are recessed at an angle that accommodates seating of the angled rails 950, 960 and are sized to slidably accept the angled rails 950, 960. Several ridges 947 are disposed on a lower surface 953 the angled rail 950 and are sized to engage corresponding ridges 48 disposed on a bottom surface of the channel 970. The ridges complementary 947, 948 are adapted to limit rotation of the intradiscal elements 911, 915 to discrete incremental positions, and in some cases, can bias the rotation in one direction or substantially prevent rotation in one direction.

Figure 31A:
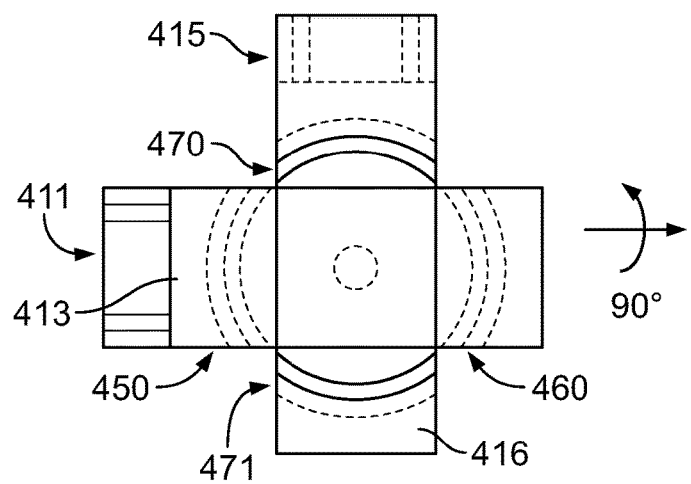
FIGS. 31A-31F are various views that illustrate pre-assembly of the spinal implant shown in FIG. 24.
Figure 31B:
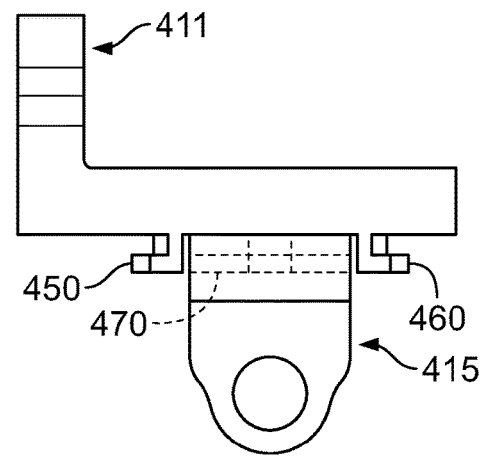
Figure 31C:
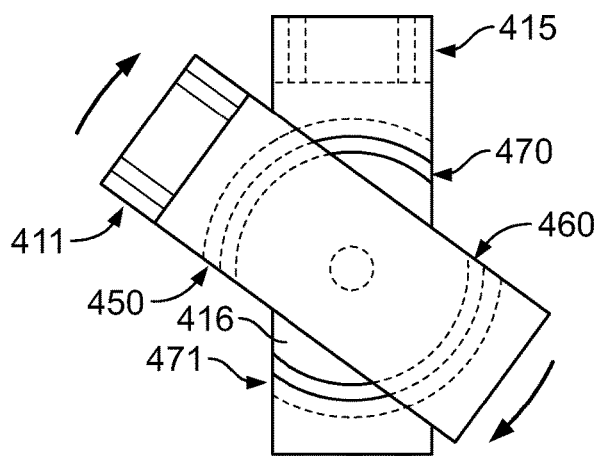
Figure 31D:
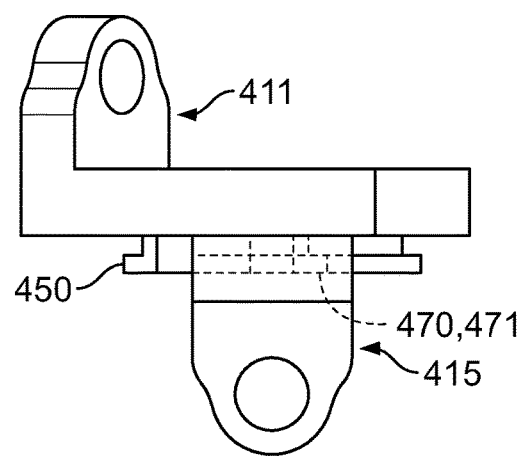
Figure 31E:
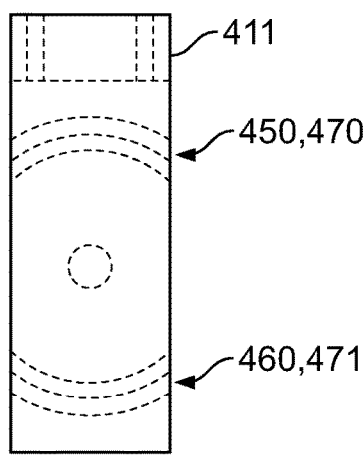
Figure 31F:
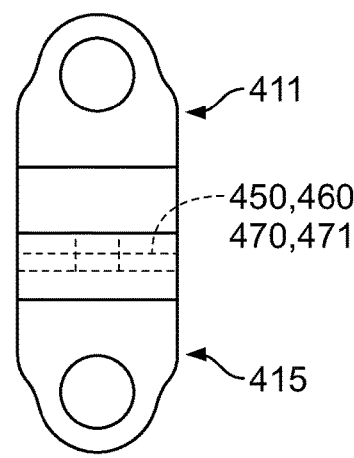

With reference to the FIG. 24 embodiment, a description is provided, with the use of FIGS. 31A-31F, of a method for assembling two intradiscal elements that include engagement mechanisms that prevent separation of the two intradiscal elements over a range of relative rotational orientations. The method involves the assembly of the first intradiscal element 411 having L-shaped engagement rails 450, 460 with the second intradiscal element 415 having corresponding L-shaped engagement channels 470, 471, to form implant 410. Referring particularly to FIGS. 31A and 31B, initially, the first (upper) intradiscal element 411 is held apart from and oriented perpendicularly to the second intradiscal element 415, with the medial surface 412 of the first intradiscal element 411 facing the medial surface 416 of the second intradiscal element 416. Next, the two intradiscal elements 411, 415 are brought into proximity of one another such that the post element 430 extending from the medial surface 412 can be inserted into the aperture 433 included within the second intradiscal element 415. In some examples, the post element 430 may be inserted additionally through a snap-ring 432 (not shown in FIG. 31). Next, the medial surfaces 412, 416 are brought into direct contact. In the cases where the snap-ring is used, a sufficient force must be applied between the intradiscal elements 411, 415 such that the snap ring 432 seats in both the groove 431 disposed on the post element 430 and the groove 434 included within a surface of the aperture 433. Referring particularly to FIGS. 31C and 31D, the first intradiscal element 411 may then be rotated while the second intradiscal element 415 is held fixed. Referring particularly to FIGS. 31E and 31F, as the first intradiscal element 411 is rotated relative to the second intradiscal element 415, the rails 450, 460 and corresponding channels 470, 471 are brought into contact, and the rails 450, 460 slidably engage within the channels 470, 471.

Cross-sections of the channels 470, 471 may be sized slightly larger than cross-sections of the rails 450, 460 to reduce a sliding friction between the rails 450, 460 and the channels 470, 471, and thus reduce binding between the intradiscal elements 411, 415 while the first intradiscal element 411 is rotated relative to the second intradiscal element 415. In a general embodiment, the channels 470, 471 may be chamfered or otherwise enlarged near anterior and posterior surfaces of the intradiscal elements and/or the projections 450, 460 may be tapered or otherwise reduced in size near the anterior and posterior surfaces of the intradiscal elements 411, 415 to facilitate assembly of the intradiscal elements 411, 415 and reduce binding of the rails 450, 460 with the anterior and posterior surfaces of the second intradiscal element 415 while the rails 450, 460 are engaged with the channels 470, 471.

In some examples, when the rails are engaged with the channels, the first intradiscal element cannot be deflected from the second intradiscal element over a certain range of rotational positions (e.g., from −30 to +30°). Because the rails secure the inner surfaces of the intradiscal elements in substantial conformity when engaged with the channels 470, 471, a snap-ring may be unnecessary to provide conformity between the inner surfaces, especially for embodiments having two or more rails 450, 451 and two or more respective channels 470, 471 that slidably engage the rails. In such embodiments, the snap-ring and grooves may be not be included within the implant (as is the case in the examples of FIGS. 24 and 29), and the pivotal relationship between the intradiscal elements may be provided by a post member and an aperture sized to accommodate and allow rotation of the post element.

Figure 32:
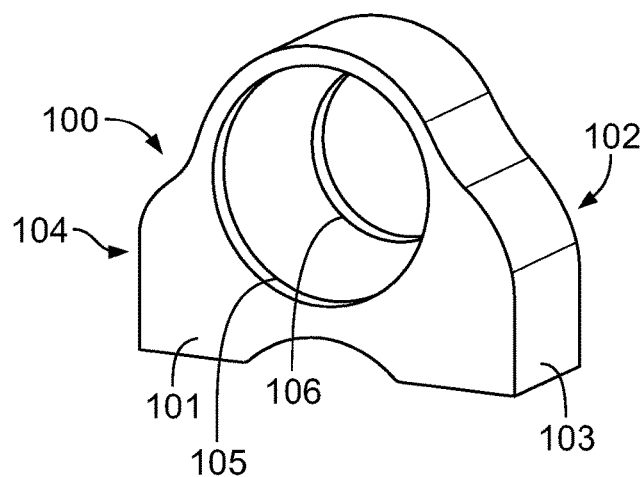
FIGS. 32-34 illustrate a mechanism that may be used in connection with various embodiments of spinal implants, such as the implant shown in FIGS. 1-5, to achieve rotational adjustments in a coronal plane.
Figure 33:
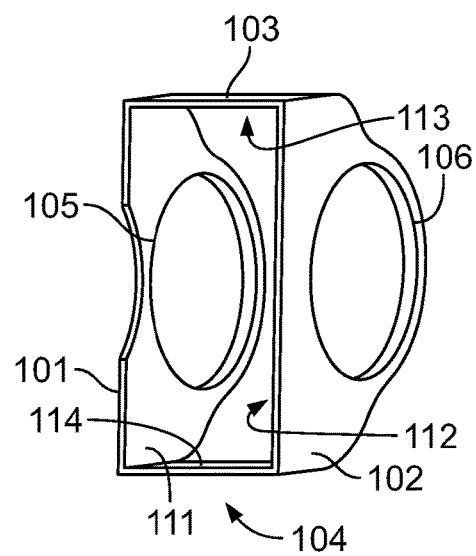
Figure 34:
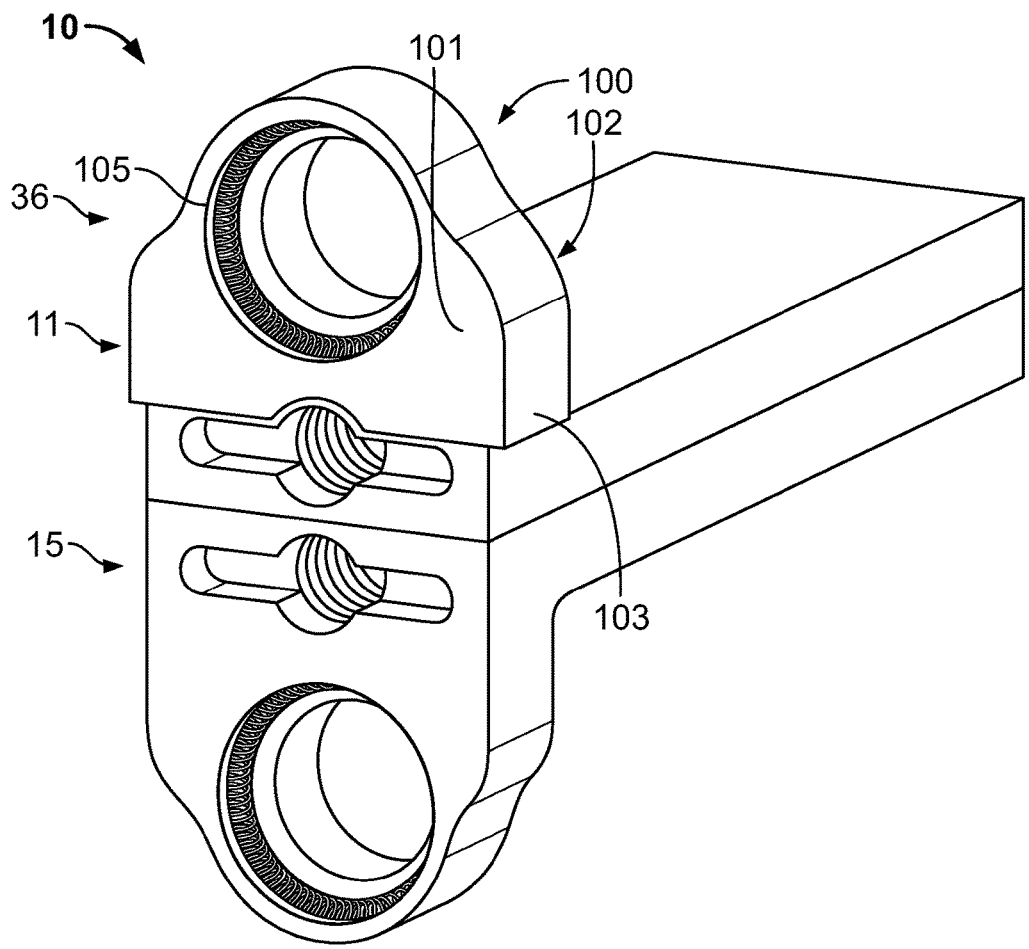

FIGS. 32-34 illustrate a cap member that is designed to be used in conjunction with a flange portion of a spinal implant described herein, wherein the cap member serves to achieve rotation of one vertebra relative to another in a coronal plane (assuming lateral implantation of the spinal implant). Referring particularly to FIGS. 32 and 33, a cap member 100 includes an outer proximal surface 101, an outer distal surface 102, an outer anterior surface 103, an outer posterior surface 104, an inner proximal surface 111, an inner distal surface 112, an inner anterior surface 113, and an inner posterior surface 114. The proximal surfaces 101, 111 include a cylindrical bore 105 therethrough. The distal surfaces 102, 112 similarly include a cylindrical bore 106 therethrough. Referring particularly to FIG. 33, the cap member 100 is sized to slidably and snugly fit over the flange portion 36 of the first intradiscal element 11 of the implant 10. When the cap member 100 is fully engaged with flange portion 36, the inner proximal surface 111 of the cap member 100 conforms to the proximal surface 24 of the flange portion 36, and the inner distal surface 112 of the cap member 100 conforms to the medial surface 41 of the flange portion 36, the inner anterior surface 103 conforms to the anterior surface 18 of the flange portion 36, the inner posterior surface 104 conforms to the posterior surface 20 of the flange portion 36, and the bores 105, 106 are substantially aligned with the outermost bore 50 of the flange portion 36. The cap 100 may be made of any bio-compatible material, such as a metal or a plastic.

The cap member 100 can be constructed to have a variable distance separating the outer distal surface 102 from the inner distal surface 112, while still being sized to slidably engage and snugly fit over the flange portion 36. For example, the cap 100 may have a variable thickness such that the dimensions of the inner cap surfaces 111, 112, 113, 114 are unchanged, but the dimensions of the outer cap surfaces 101, 102, 103, 104, as well as the length of the bores 105, 106 are increased. Alternatively, in some embodiments, the thickness of the material defining the surfaces 102, 112 and the bore 106 may be varied, while the inner dimensions of the cap member 100 (defined by the inner surfaces 111, 112, 113, and 114) remain unchanged. When the cap member 100 is fully engaged with flange portion 36, the surface 102 of the cap member 100 will engage the first vertebrae. In cases where the flange portions 36, 37 have similar dimensions, the presence of cap member 100 on the flange portion 36 will allow the user to translate the first vertebra a distance D (where D is the distance separating the surface 112 from the surface 102 along the bore 106) relative to the second vertebra. For example, if the implant 10 is inserted through a lateral working channel (as known to those skilled in the art of implanting spinal fusion implants) and flange portions 36, 37 are secured to lateral bodies of the vertebrae, the presence of the cap member 100 on the flange portion 36 will translate the first vertebra relative to the second vertebra in the coronal plane. Such translation may be advantageous for correcting spinal deformities such as scoliosis, especially in light of the increasingly precise estimates of abnormal vertebral translation and rotation provided by modern software.

Figure 35:
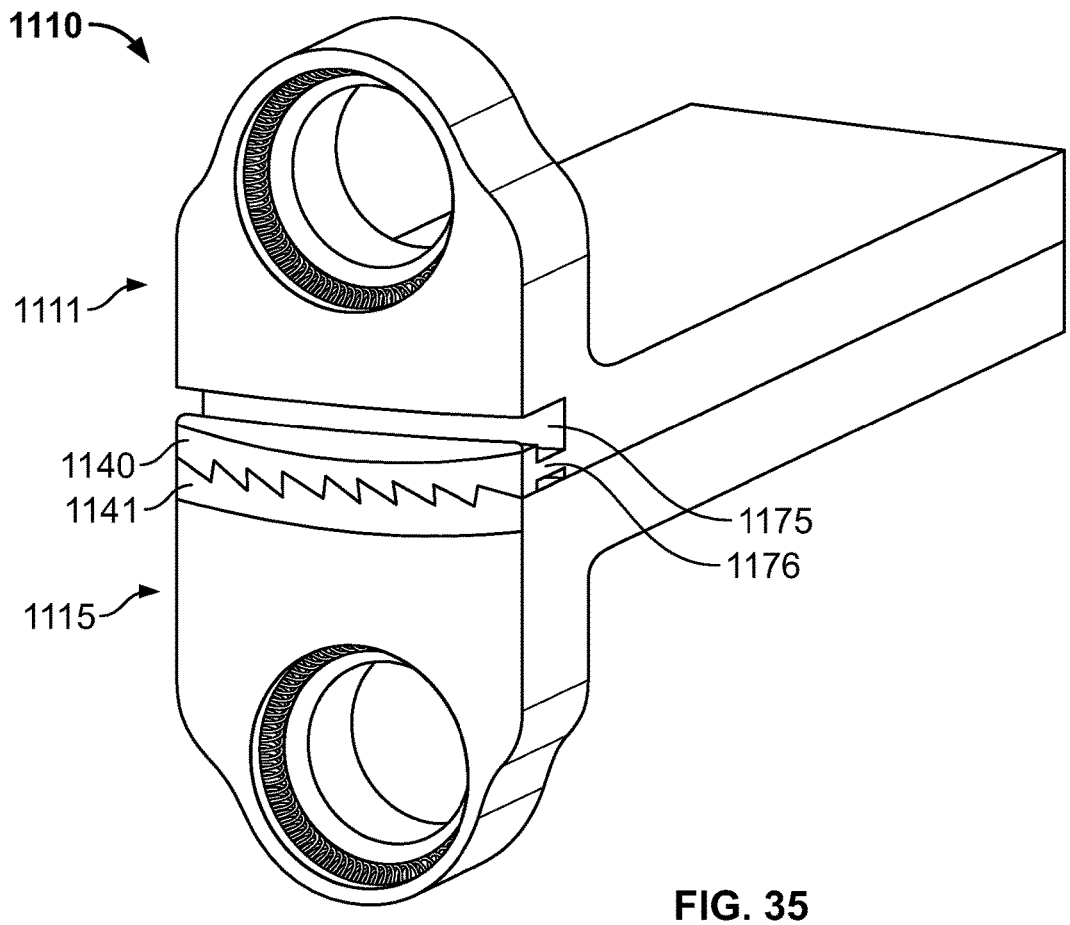
FIGS. 35-36 are various views that illustrate yet another embodiment of a spinal implant to achieve rotational adjustment of the spine.
Figure 36:
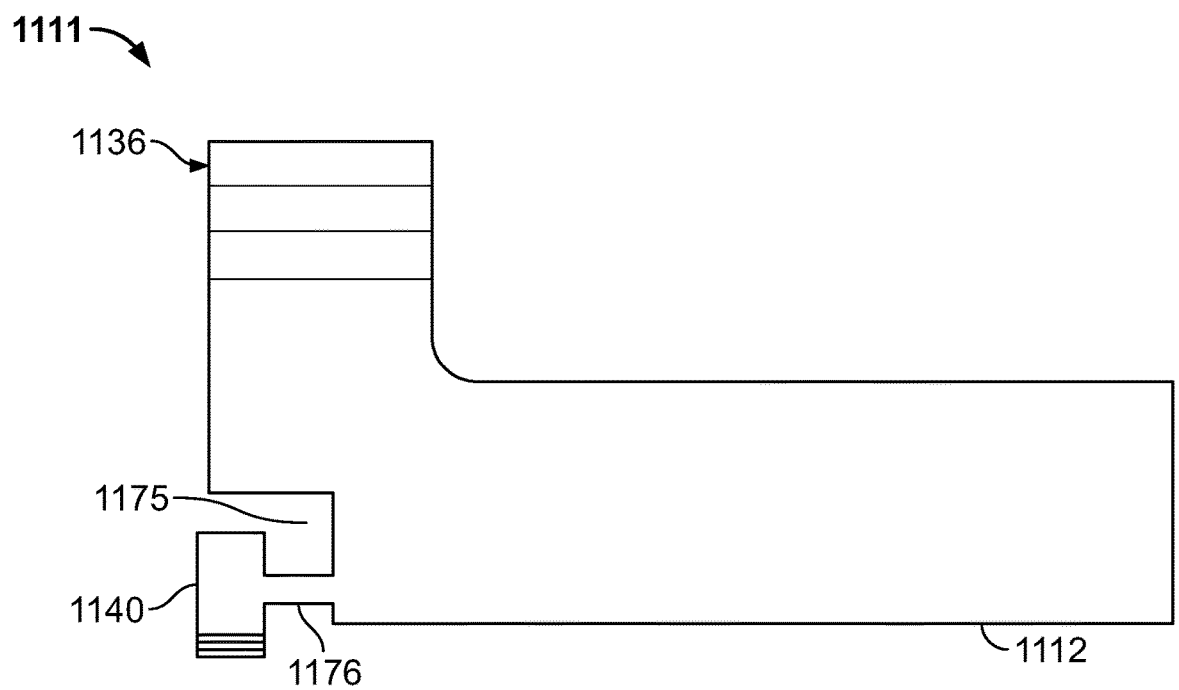

FIGS. 35-36 illustrate an alternative embodiment of a spinal implant 1110. Again, the spinal implant 1110 includes a first (upper) intradiscal element 1111 and a second (lower) intradiscal element 1115, with the two elements 1111, 1115 being designed to be rotatably coupled to one another and being designed to be positioned within a disc space as a unit in a generally vertically stacked configuration. The upper intradiscal element 1111 includes a recess 1175 that extends horizontally from a proximal surface 1124 of the first intradiscal element 11 to a point short of a distal surface 1122 of the first intradiscal element 1111 and also extends from an anterior surface 1118 to a posterior surface 1120 of the first intradiscal element 1111. Several ridges 1140 are flexibly coupled to the first intradiscal element 1111 by a flexible strip 1176. In a general embodiment, the flexible strip 1176 may extend the entire width of the proximal end of the implant 1110 from the anterior surface 1118 to the posterior surface 1120 of the first intradiscal element 1111 as in FIGS. 35-36, or may only extend along a portion of the distance between the anterior and posterior surfaces 1118, 1120. The flexible strip 1176 may be made of any biocompatible material, such as titanium, stainless steel, or plastic. The flexible strip 1176 allows the ridges 1140 to deflect in a direction perpendicular to a lower surface 1112 of the first intradiscal element 1111 and away from ridges 1141, generally in the direction of the flange portion 36. Thus, the flexible strip 1176 allows the first intradiscal element 1111 to rotate relative to the intradiscal element 1115 without requiring any break in the conformity between the surfaces 1112, 1116. In some embodiments, both intradiscal elements 1111, 1115 may each be provided with a recess having a flexible strip such that the ridges 1140, 1141 are flexible relative to the surfaces 1112, 1116.

In some examples, a collection of several first and second intradiscal elements and caps may be provided as a spinal fusion implant system. The first and second intradiscal elements may have various heights and formed with various angulations of the surfaces. The caps may have various distances (D) between the inner and outer distal surfaces. The user may then select and combine a particular first intradiscal element with a particular second intradiscal element and optionally with a particular cap to form an implant having the desired combination of height, sagittal angulation, and coronal angulation, and the capability to translate and/or rotate a first vertebra relative to a second vertebra. The first intradiscal elements are secured to the second intradiscal elements by means of a snap ring in cooperation with grooves and/or by means of one or more projections in cooperation with one or more channels.

The user of the above described system may approach the spine from a lateral aspect for fixation of flange portions to a lateral surface of first and second vertebrae by means of bone screws. The system includes several first intradiscal elements having similar heights, and each first intradiscal element having different angles defined by upper and lower surfaces to restore the natural curvature of the spine (e.g., in the case of lumbar lordosis) in the sagittal plane, as is often necessary to treat spinal deformities such as scoliosis. To accomplish this, the anterior side of the first intradiscal element may be have a height greater than that of the posterior side such that the upper and lower surfaces converge toward one another at a posterior side of the first intradiscal element.

The system further includes several second intradiscal elements having similar heights, and each second intradiscal element having different angles defined by upper and lower to correct spinal deformity in the coronal plane, as is often necessary to treat spinal deformities such as scoliosis. To accomplish this, the distal end may have a height less than that of the proximal end, such that the upper and lower surfaces converge toward one another at the distal end. One advantage of this system is that the user can select and combine a number X of uniquely sized first intradiscal elements capable of correcting spinal deformity in the sagittal plane with a number Y of uniquely sized second intradiscal elements capable of correcting spinal deformity in the coronal plane to potentially select from a number Z of potential implants, where $Z=(X)(Y)$. For example, if the system includes 10 first intradiscal elements, 10 second intradiscal elements, and 10 caps, then the user could then potentially assemble any of 1,000 implants each having a desired height and a unique combination of a sagittal correction angle, coronal correction angles, and translational correction in the coronal plane. Furthermore, if each implant can be rotated into five 5 positions (e.g., 0°, 2°, 4°, 6°, 10°), the user would be able to select from among 5,000 unique manipulations of the first vertebra relative to the second vertebra, using a modestly sized kit of 30 subcomponents.

Figure 37:
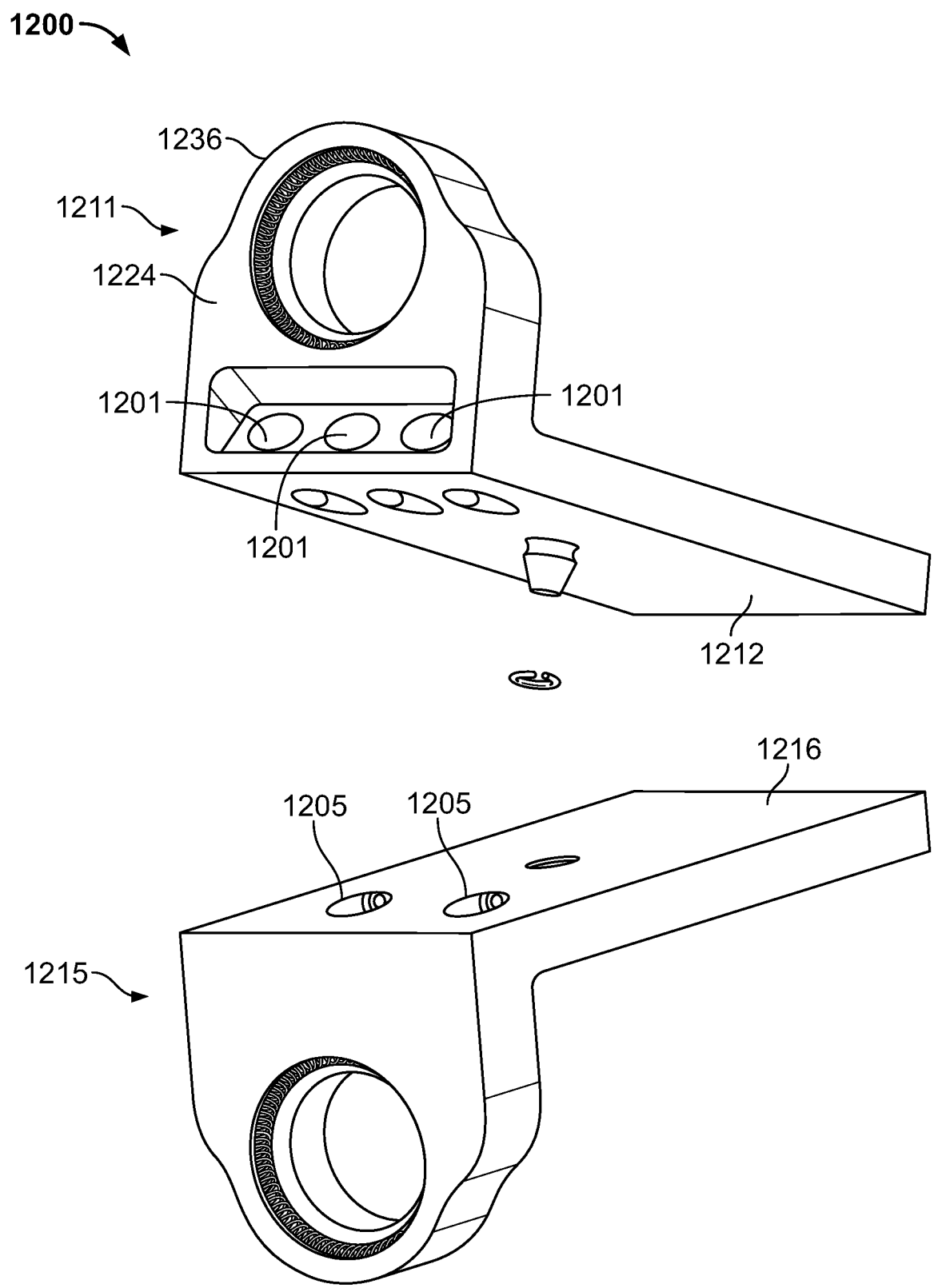
FIG. 37 illustrates yet another embodiment of a spinal implant to achieve rotational adjustment of the spine.

FIG. 37 illustrates an alternative embodiment of a spinal fusion implant 1210 similar to the embodiment of FIGS. 13-16, except that the FIG. 37 embodiment provides additional bores that provide multiple rotational positions for the intradiscal elements. The implant 1210 includes a first (upper) intradiscal element 1211 and a second (lower) intradiscal element 1215, with the two elements 1211, 1215 being designed to be rotatably coupled to one another and being designed to be positioned within a disc space as a unit in a generally vertically stacked configuration. The first intradiscal element 1211 includes three bores 1201 that extend from a proximal surface 1224 of a flange portion 1236, and the intradiscal element 1215 includes two threaded bores 1205 extending from an upper surface 1216 of the second intradiscal element 1215. Any one of the three bores 1201 within the first intradiscal element can be aligned with either of the two bores 1205 within the first intradiscal element 1211, providing six distinct and stably-locked rotational positions.

Figure 38:
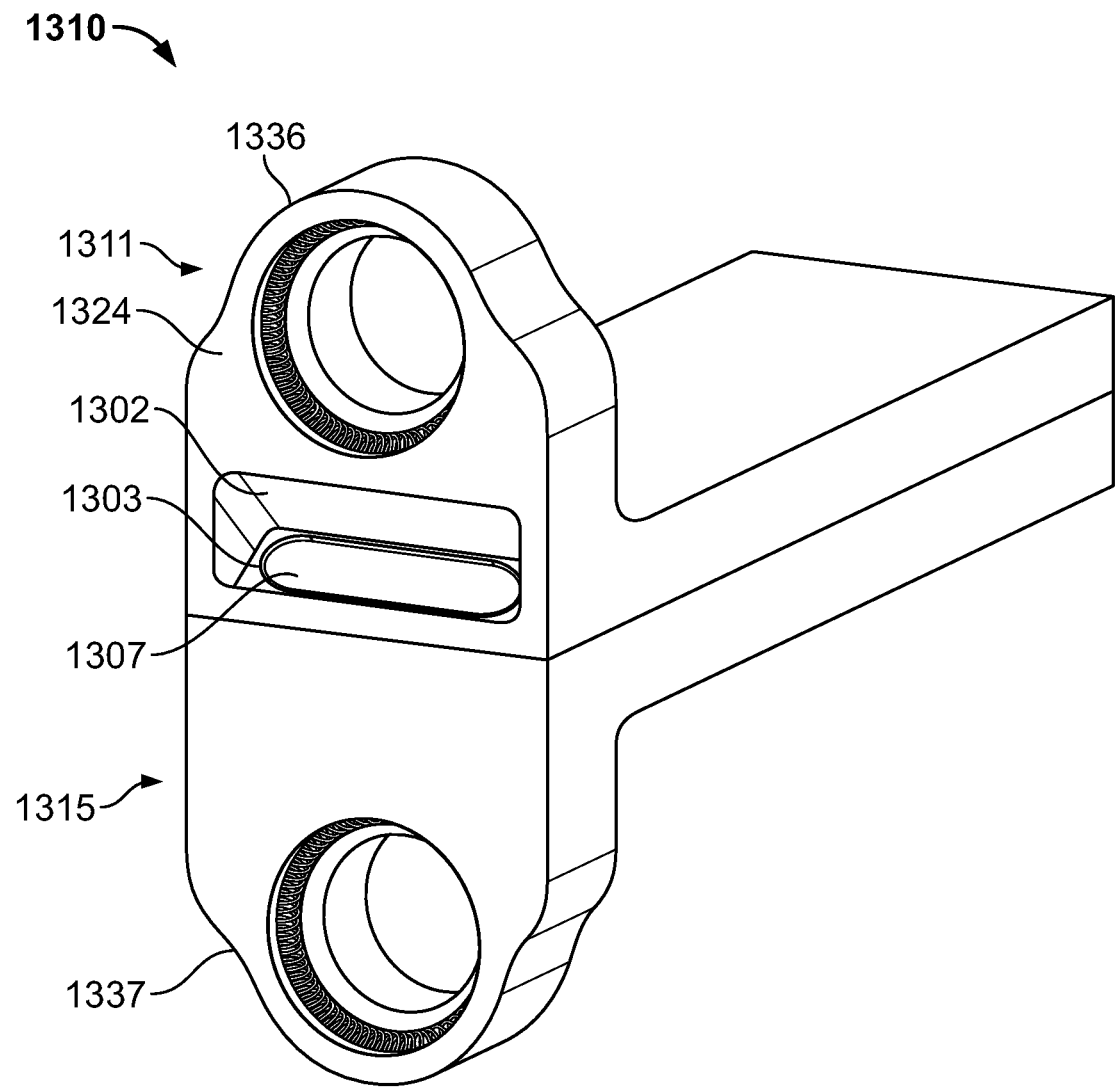
FIGS. 38-40 are various views that illustrate yet another embodiment of a spinal implant to achieve rotational adjustment of the spine.
Figure 39:
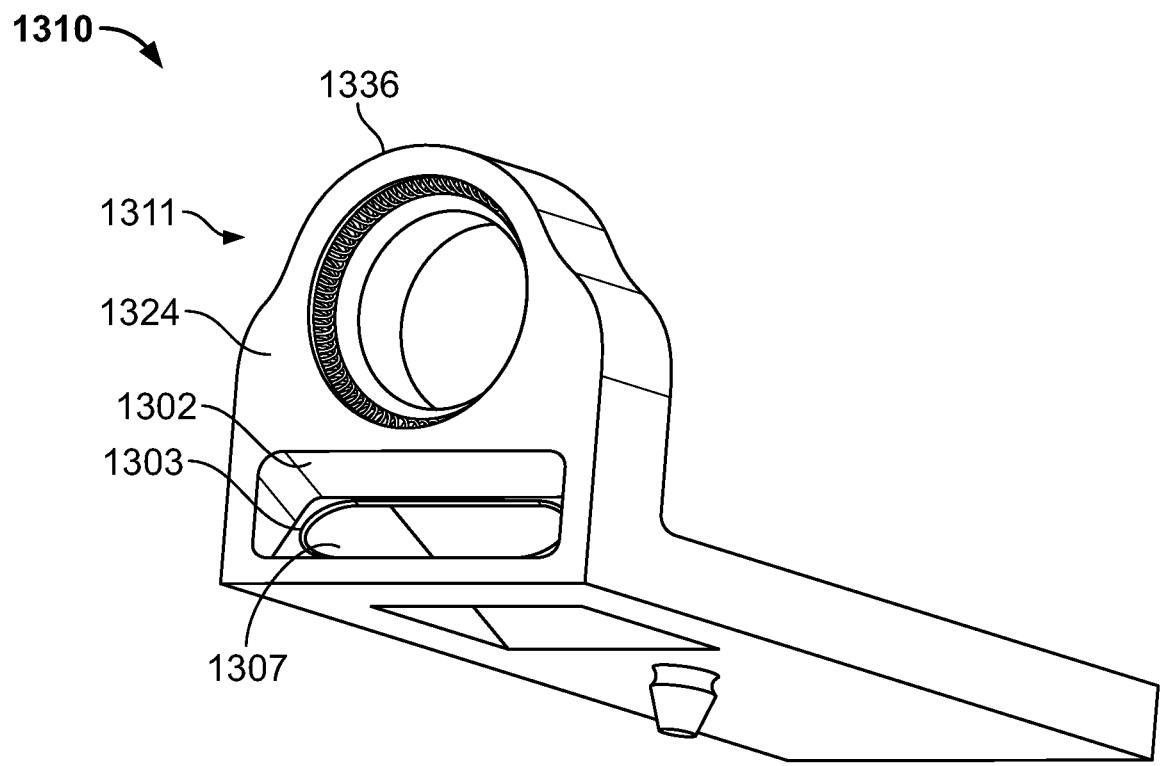
Figure 39:
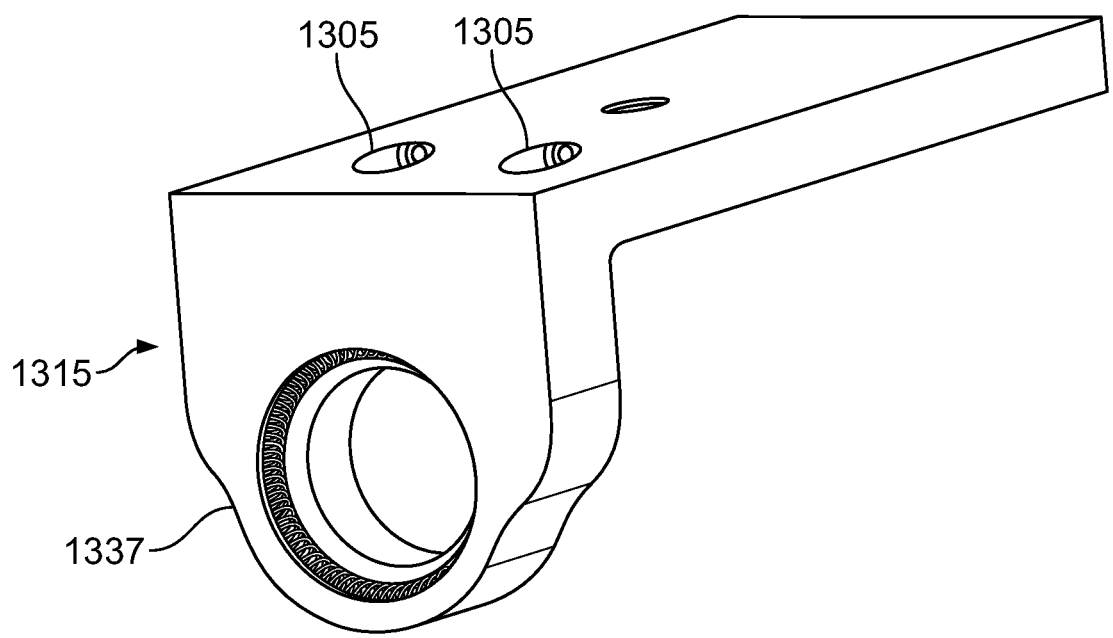
Figure 40:
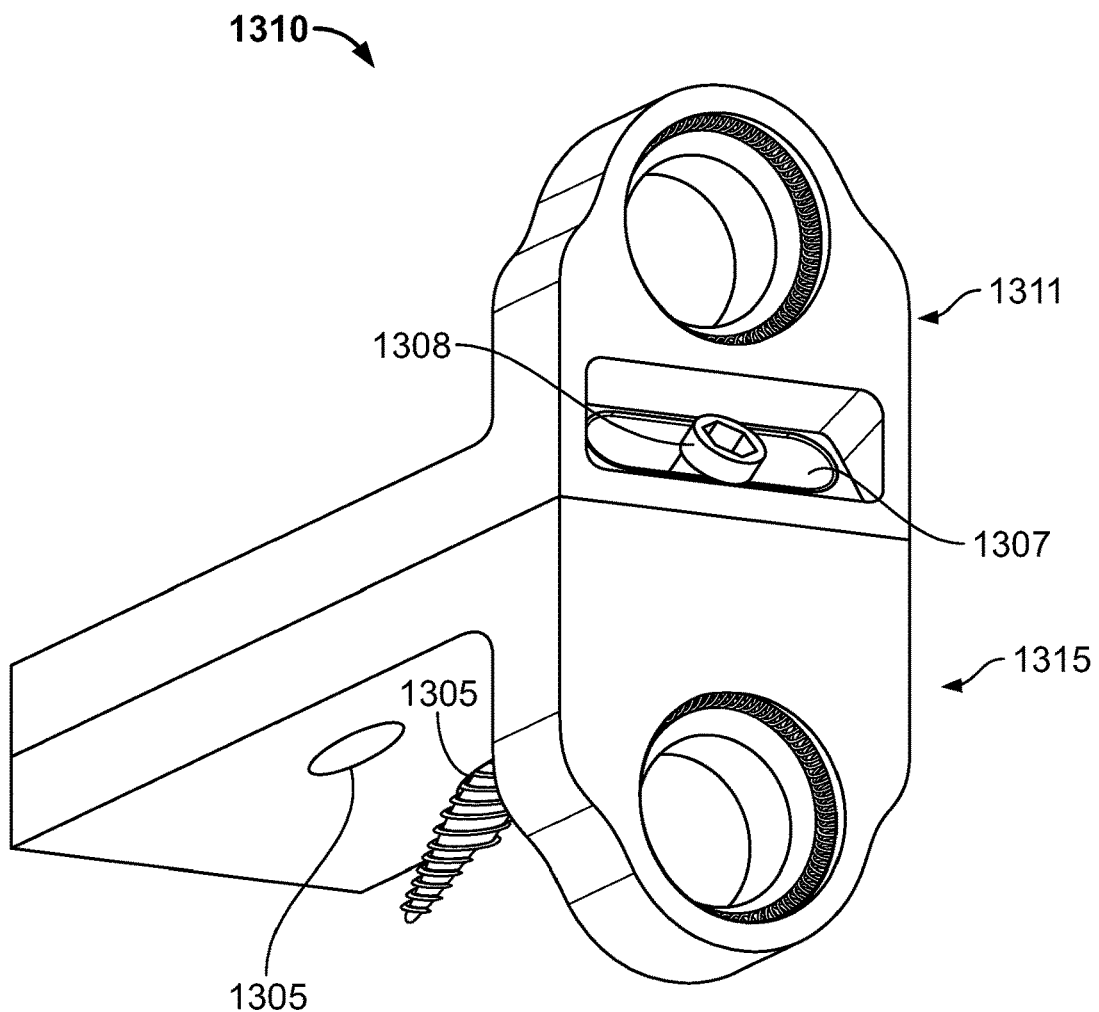

FIGS. 38-40 illustrate another embodiment of a spinal fusion implant 1310 similar to the embodiment of FIG. 37, except that the bores are replaced by an elongate slot to provide a range of rotational positions for the intradiscal elements. The implant 1310 includes a first (upper) intradiscal element 1311 and a second (lower) intradiscal element 1315, with the two elements 1311, 1315 being designed to be rotatably coupled to one another and being designed to be positioned within a disc space as a unit in a generally vertically stacked configuration. The first intradiscal element 1311 includes an elongate slot 1307 that extends from a recess 1302 on a proximal surface 1324 of a flange portion 1336 to a medial surface 1312 of the first intradiscal element 1311. The second intradiscal element 1315 includes two threaded bores 1305 that extend from an upper surface 1316 of the second intradiscal element. The slot 1307 is sized such that a bolt can pass through the slot 1307 and thus thread into the bores 1305. A bolt-locking means, such as a canted-coil, may be provided on a seat 1303 surrounding the slot 1307. In the example of FIGS. 38-40, the implant 1310 can be locked into a range of several rotational positions. For example, the first intradiscal element 1311 can be locked into either of a clockwise or counterclockwise rotational position within a range of approximately −20° to +20° relative to the second intradiscal element 1315 (wherein vertically aligned flange portions 1336, 1337 define the 0° point).

The threaded bore 1305 in the second intradiscal element 1315 extends from the surface 1316 to a surface 1317 of the second intradiscal element 1315. A bolt 1308 is sufficiently long that, when a head on a proximal end of the bolt 1308 is seated against a recess 1302, a distal end of the bolt 1308 extends past the surface 1317 and into the body of the second vertebra. The second vertebra has already been bolted to the second intradiscal element 1315 through the bore 1337 when the bolt 1308 is inserted, such that bolt 1308 further stabilizes the interaction between the surface 1317 of the second intradiscal element 1315 and the second vertebra.

Figure 41:
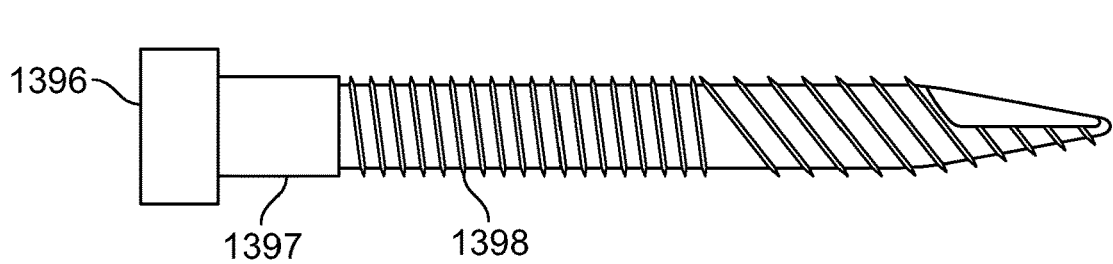
FIGS. 41-43 illustrate details of a bone screw that may be used in spinal implants disclosed in this document, such as the spinal implant shown in FIGS. 38-40.
Figure 42:
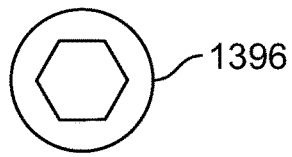
Figure 43:
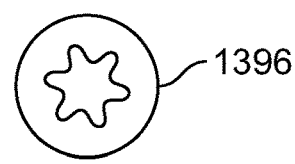

Referring to FIGS. 41-43, the bolt 1308 includes a bolt head 1396, a shank 1397, and a threaded shank 1398, all sharing a common longitudinal axis, and each having successively smaller cross-sectional diameters. In a general embodiment, the bolt head 1396 may include any of a number of driving-means, such as a hex-drive (see FIG. 42), a hex-lobe drive, or a torx-drive (see FIG. 43).

Figure 44:
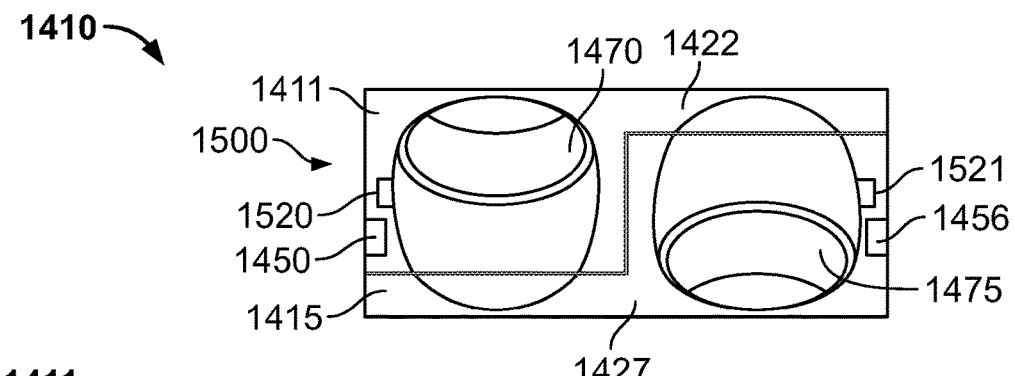
FIGS. 44-46 are various views that illustrate yet another embodiment of a spinal implant to achieve rotational adjustment of the spine.
Figure 45:
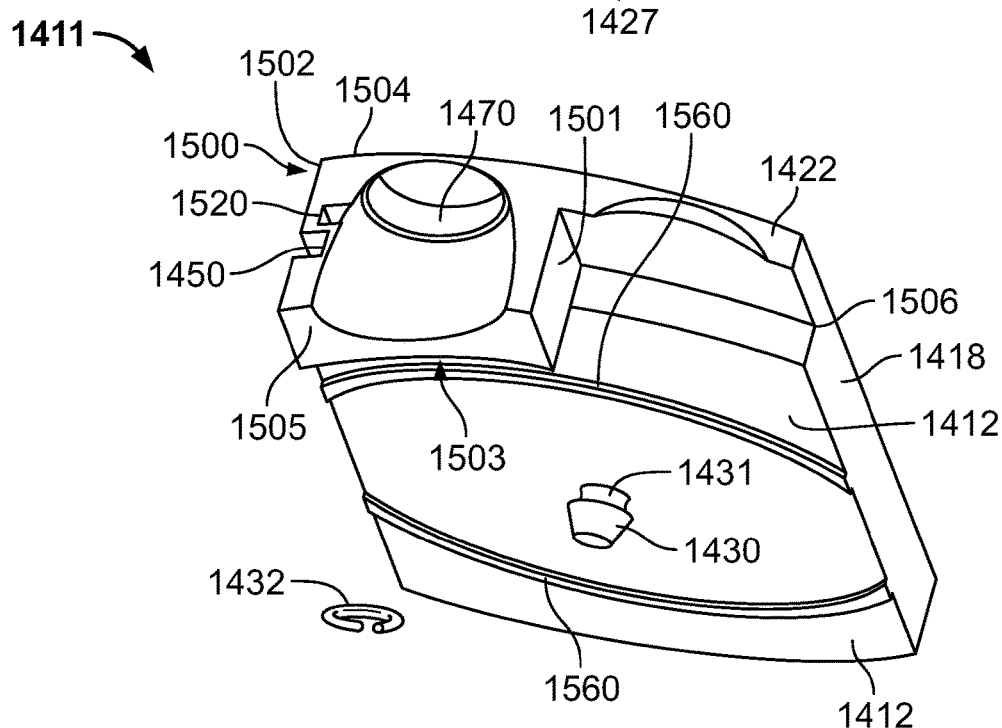
Figure 46:
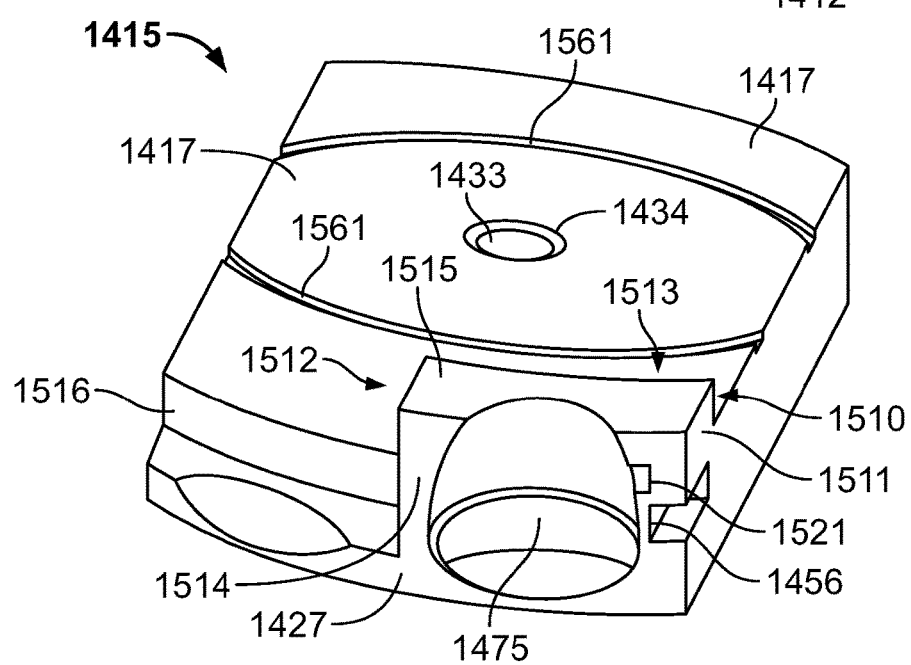

FIGS. 44-46 illustrate another low-profile embodiment of a spinal fusion implant 1410 that is designed for anterior or antero-lateral insertion into the disc space, as opposed to being designed for insertion using a lateral approach to the spine. Specifically, FIG. 44 is a proximal (trailing end) view of the assembled implant 1410, while FIG. 45 provides a perspective view of the first intradiscal element 1410 and FIG. 46 provides a perspective view of the second intradiscal element 1415. The implant 1410 includes the first (upper) intradiscal element 1411 and the second (lower) intradiscal element 1415, with the two elements 1411, 1415 being designed to be rotatably coupled to one another and being designed to be positioned within a disc space as a unit in a generally vertically stacked configuration. The first intradiscal element 1411 includes a generally rectangular first borehole structure 1500 that substantially surrounds the first bore 1470 and that extends below, and perpendicularly to, a lower surface 1412 of the first intradiscal element 1411. The borehole structure 1500 includes an anterior surface 1501, a posterior surface 1502, a distal surface 1503, a proximal surface 1504, and a medial surface 1505. The first intradiscal element 1411 further includes, adjacent the borehole structure 500, a first recess 1506 that opens in a lateral or proximal surface 1422 of the first intradiscal element 1411 and extends from an anterior surface 1418 of the first intradiscal element 1411 to a plane defined by an anterior surface 1501 of the borehole structure 1500. The second intradiscal element 1415 includes a second borehole structure 1510 that substantially surrounds a second bore 1475, and that extends below, and perpendicularly to, an upper surface 1417 of the second intradiscal element 1415. The borehole structure 1510 includes an anterior surface 1511, a posterior surface 1512, a distal surface 1513, a proximal surface 1514, and a medial surface 1515. The second intradiscal element 1515 further includes, adjacent the borehole structure 1510, a second recess 1516 that opens in a lateral or proximal surface 1427 of the second intradiscal element 1415 and extends from a posterior surface 1426 to the posterior surface 1512 of the borehole structure 1510. The first borehole structure 1500 is sized to fit within the second recess 1516 when the medial surfaces 1412, 1417 are brought into contact with one another. Similarly, the second borehole structure 1510 is sized to fit within the first recess 1506 when the medial surfaces 1412, 1417 are brought into contact with one another.

Cross sections of the distal surfaces 1503, 1513 of the two borehole structures 1500, 1510 are arcuate or semi-circular within a plane of the medial surfaces 1412, 1417. The recesses 1506, 1516 are similarly arcuate or semi-circular within a plane of the medial surfaces 1412, 1417 and sized to accept the borehole structures 1500, 1510. Thus, when the medial surfaces 1412, 1417 are brought into contact with one another, the first intradiscal element 1411 can be rotated relative to the second intradiscal element 1415, and the borehole structures 1500, 1510 slide into the corresponding recesses 1506, 1516. For example, as the first intradiscal element 1411 is rotated relative to the second intradiscal element 1415 about a post element 1430, the borehole structure 1500 slides laterally into the recess 1516, and the borehole structure 1510 slides laterally into the recess 1506 from the opposite direction. In some embodiments, arrays of biased ridges 1560, 1561 may be included as shown, to provide incremental and/or biased rotation. Two insertion instrument engagement grooves 1450, 1456 may be provided for engagement with an insertion instrument to insert the implant into a patient's disc space.

To accomplish relative rotation of the two elements 1411, 1415 after the implant 1410 has been placed within a disc space, two rotation instrument engagement grooves 1520, 1521 are provided. The engagement groove 1520 extends from the bore 1470 to a point anterior to the posterior surface 1502 of the borehole structure 1500. The engagement groove 1521 extends from the bore 1475 to a point posterior to the anterior surface 1511 of the borehole structure 1510. The engagement grooves 1520, 1521 within the bores 1470, 1475 are sized to accept laterally separating spreader arms. For example, a spreader tool including a pair of spreading arms that fit within the grooves 1520, 1521 may be provided. Once the implant 1410 is inserted and affixed to the first and second vertebrae, the distance between the bores 1470, 1475 can be adjusted to effect de-rotation of the first vertebra relative to the second vertebra. In some examples, this can be achieved by applying a separation force to either the bores 1470, 1475 or to the engagement grooves 1520, 1521.

Figure 47:
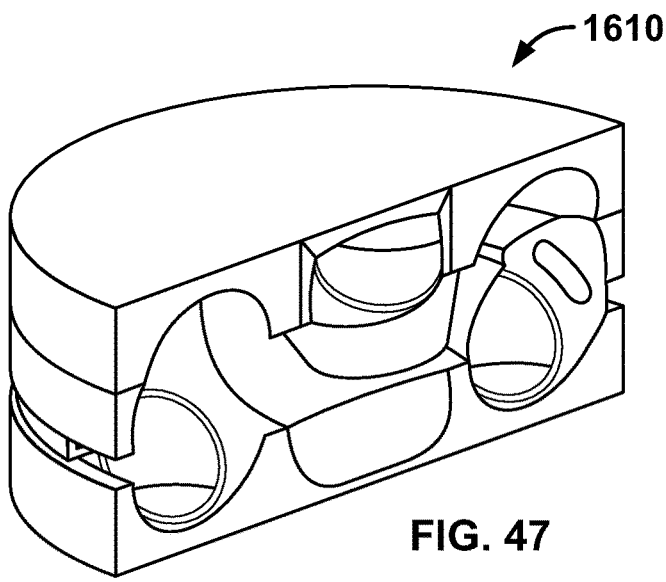
FIGS. 47-49 are various views that illustrate yet another embodiment of a spinal implant to achieve rotational adjustment of the spine.
Figure 48:
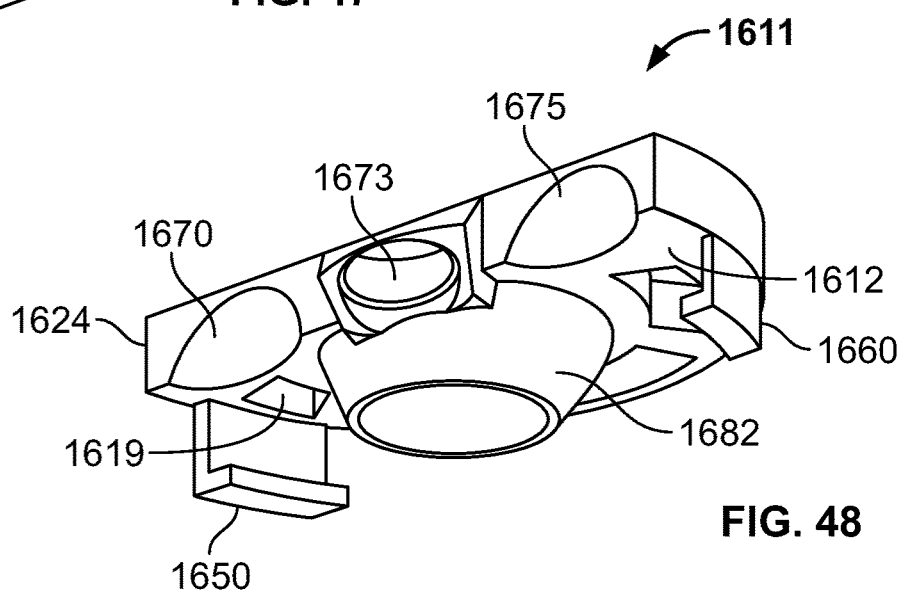
Figure 49:
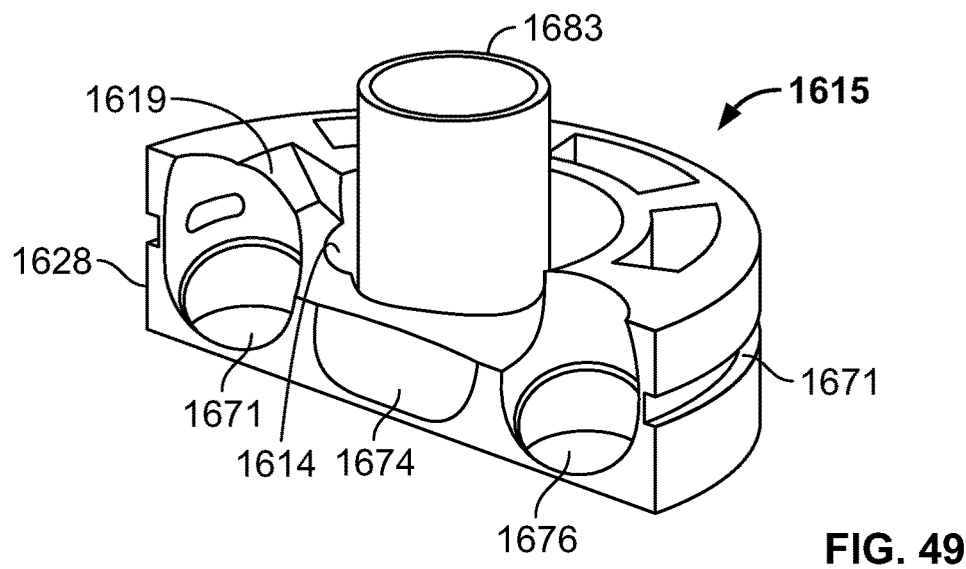

FIGS. 47-49 illustrate an alternative embodiment of a low-profile spinal fusion implant 1610 that allows for insertion of three screws and includes a cylindrical post member 1683 and respective cap member 1682 extending from inner surfaces of the intradiscal elements. As with the embodiment of FIGS. 44-46, this implant 1610 is designed to be implanted into a disc space using an anterior or antero-lateral approach to the spine. Generally, the implant 1610 includes a first (upper) intradiscal element 1611 and a second (lower) intradiscal element 1615, with the two elements 1611, 1615 being designed to be rotatably coupled to one another and being designed to be positioned within a disc space as a unit in a generally vertically stacked configuration. The first intradiscal element 1611 includes one bore 1673 and two cut-outs 1670, 1675 provided in a proximal end 1624 of the first intradiscal element 1611, and the second intradiscal element 1615 includes two threaded bores 1671, 1676 and one cut-out 1674 provided in a proximal end 1628 of the second intradiscal element 1615. When the elements 1610, 1615 are assembled, cut-out 1670 corresponds with bore 1671, cut-out 1674 corresponds with bore 1673, and cut-out 1675 corresponds with bore 1676. The first intradiscal element 1611 further includes a substantially cylindrical cap 1682 extending from an approximate center of the lower surface 1612 of the first intradiscal element. The second intradiscal element 1615 further includes a cylindrical post 1683 extending an approximate center of an upper surface 1614 of the second intradiscal element. The first intradiscal element 1611 further includes L-shape rails 1650, 1660 extending from anterior and posterior edges of the first intradiscal element. Accordingly, the second intradiscal element 1615 includes corresponding L-shaped channels 1670, 1671 along anterior and posterior edges of the second intradiscal element that are sized and formed to be engaged with the ridges 1650, 1660 when the implant 1610 is assembled. An inner diameter of the cap 1682 is sized such that the cap 1682 can fit over the post 1683, allowing rotation of the first intradiscal element 1611 relative to the second intradiscal element 1615. The spinal fusion implant 1611 further includes apertures 1619 in which osteoinductive materials can be deposited to improve boney fusion between first and second vertebrae that are in contact with the spinal fusion implant 1610.

A number of embodiments of the invention have been described. Nevertheless, it will be understood that various modifications may be made without departing from the spirit and scope of the invention. Accordingly, other embodiments are within the scope of the following claims.

What is claimed is:

1. A spinal implant adapted to be positioned within a disc space between adjacent vertebrae, the implant comprising:
    a first intradiscal element comprising a first outer surface adapted to be positioned adjacent an endplate of a first one of the adjacent vertebrae and comprising a first medial surface that is opposite the first outer surface, wherein the first intradiscal element comprises a first proximal flange portion that extends generally perpendicularly to a longitudinal axis of the first intradiscal element, and a first borehole extending through the first proximal flange portion, wherein the first proximal flange portion is configured to be positioned against a side aspect of a first vertebra for receipt of a bone screw through the first borehole in a trajectory that is generally parallel with the longitudinal axis of the first intradiscal element, and wherein the first intradiscal element comprises a cap configured to be placed on the first proximal flange portion, the cap comprising holes formed in each side of the cap that align with the first borehole when the cap is placed on the first proximal flange portion, the cap having a thickness in a medial portion selected to provide rotational pressure on a side of the vertebra to which the first proximal flange portion is affixed;
    a second intradiscal element comprising a second outer surface adapted to be positioned adjacent an endplate of a second one of the adjacent vertebrae and comprising a second medial surface that is opposite the second outer surface and adapted to generally face the first medial surface upon assembly of the first intradiscal element with the second intradiscal element;
    a coupling mechanism that is associated with the first and second medial surfaces and that is adapted to provide relative rotational movement between the first and second intradiscal elements in a plane generally parallel with the first and second medial surfaces and about an axis at a center portion of the first and second medial surfaces; and
    a rotational movement resistance mechanism adapted to resist rotational movement from a plurality of incremented relative rotational positions of the first intradiscal element in relation to the second intradiscal element.

2. The spinal implant of claim 1, wherein the coupling mechanism comprises a post element extending from the center portion of one of the first and second medial surfaces and an aperture provided in the center portion of the other of the first and second medial surfaces, the post element and aperture adapted to be coupled together.

3. The spinal implant of claim 2, wherein the post element comprises a bulbous distal end, and the aperture comprises an enlarged lower portion that receives the bulbous distal end of the post element.

4. The spinal implant of claim 3, wherein the coupling mechanism further comprises a snap ring adapted to be positioned about a neck of the post element proximal of the bulbous distal end, and the aperture further comprises a circumferential chamber into which the snap ring is able to be engaged.

5. The spinal implant of claim 1, wherein the second intradiscal element has formed therein at least one borehole adapted to receive a second bone screw for affixing the second intradiscal implant to the first one or the second one of the adjacent vertebrae.

6. The spinal implant of claim 1, wherein the first and second outer surfaces are ridged for secure engagement with the endplates of the adjacent vertebrae.

7. The spinal implant of claim 1, wherein the first and second outer surfaces comprise spike elements for secure engagement with the endplates of the adjacent vertebrae.

8. The spinal implant of claim 1, wherein the first intradiscal element comprises a first engagement mechanism adapted to be engaged by a distal tip of a first hand-held instrument, and the second intradiscal element comprises a second engagement mechanism adapted to be engaged by a distal tip of a second hand-held instrument, the first and second engagement mechanisms being configured to provide the relative rotational movement when acted upon by the first and second hand-held instrument in opposite directions.

9. The spinal implant of claim 1, wherein at least one of the first and second intradiscal elements is tapered from a proximal end to a distal end.

10. The spinal implant of claim 1, wherein at least one of the first and second intradiscal elements is tapered from a first side to a second side.

11. The spinal implant of claim 1, wherein the first and second intradiscal elements each have formed therein at least one fusion aperture extending from their respective outer surfaces to their respective medial surfaces, the at least one aperture in each of the first and second implants adapted to permit bone growth through the implant for spinal fusion.

12. The spinal implant of claim 11, wherein at least one of the first and second intradiscal elements have at least one viewing aperture extending from a side surface of the intradiscal element to one of the at least one fusion aperture, the at least one viewing aperture being configured to provide a view of bone growth through the fusion aperture through use of an imaging machine.

13. The spinal implant of claim 1, wherein the spinal implant is generally rectangular.

14. The spinal implant of claim 13, wherein the spinal implant is sized and configured to extend laterally across a disc space, from one lateral aspect of the disc space to the opposite lateral aspect of the disc space.

* * * * *